(12) United States Patent
Nir et al.

(10) Patent No.: US 11,583,530 B2
(45) Date of Patent: Feb. 21, 2023

(54) COMPOUNDS FOR THE PREVENTION AND TREATMENT OF MEDICAL DISORDERS AND USES THEREOF

(71) Applicant: Galectin Sciences, LLC, Norcross, GA (US)

(72) Inventors: Raphael Nir, Needham, MA (US); Eliezer Zomer, Canton, MA (US); Peter G. Traber, Gladwyne, PA (US); Joseph M. Johnson, Arlington, MA (US); Ryan George, Framingham, MA (US); Sharon Shechter, Andover, MA (US)

(73) Assignee: GALECTIN SCIENCES, LLC, Norcross, GA (US)

( * ) Notice: Subject to any disclaimer, the term of this patent is extended or adjusted under 35 U.S.C. 154(b) by 0 days.

(21) Appl. No.: 16/629,373

(22) PCT Filed: Aug. 3, 2018

(86) PCT No.: PCT/US2018/045175
§ 371 (c)(1),
(2) Date: Jan. 8, 2020

(87) PCT Pub. No.: WO2019/028357
PCT Pub. Date: Feb. 7, 2019

(65) Prior Publication Data
US 2020/0147088 A1 May 14, 2020

Related U.S. Application Data

(60) Provisional application No. 62/540,860, filed on Aug. 3, 2017.

(51) Int. Cl.
C07D 487/04 (2006.01)
A61K 31/519 (2006.01)
A61K 45/06 (2006.01)
A61P 3/10 (2006.01)

(52) U.S. Cl.
CPC ......... A61K 31/519 (2013.01); A61K 45/06 (2013.01); A61P 3/10 (2018.01); C07D 487/04 (2013.01)

(58) Field of Classification Search
CPC ....... A61K 31/519; A61K 45/06; A61P 11/06; A61P 1/16; A61P 29/00; A61P 35/00; A61P 37/00; A61P 3/10; A61P 9/00; C07D 401/10; C07D 471/04; C07D 471/14; C07D 487/04; C07D 495/04; C07D 495/14
See application file for complete search history.

(56) References Cited

U.S. PATENT DOCUMENTS

| 4,428,952 A | 1/1984 | Gianfederico et al. |
| 4,579,847 A | 4/1986 | Gianfederico et al. |
| 9,062,061 B2 | 6/2015 | Honda et al. |
| 2005/0009852 A1 | 1/2005 | Aissaoui et al. |
| 2006/0084669 A1 | 4/2006 | Moormann et al. |

FOREIGN PATENT DOCUMENTS

| CN | 105272986 A | 1/2016 |
| CN | 106220631 A | 12/2016 |
| WO | 2002057284 A1 | 7/2002 |
| WO | 2012158913 A2 | 11/2012 |
| WO | 2016004093 A1 | 1/2016 |
| WO | 2016120403 A1 | 8/2016 |

OTHER PUBLICATIONS

Sutherell, et al, On the Synthesis and Reactivity of 2,3-Dihydropyrrolo[1,2-a]quinazolin-5(1H)-ones, Synthesis, 49(1), 135-144 (2017). (Year: 2017).*
Elmuradov, et al., "Novel alpha-Methyl(Benzyl)Deoxyvasicinones", Chemistry of Natural Compounds, vol. 40, No. 5, 2004 [retrieved on Sep. 11, 2018]. Retrieved from the Internet: <URL: https://link.springer.com/article/10.1007%2Fs10600-005-0019-9> pp. 496-498.
International Search Report in International Application No. PCT/US2018/045175 dated Oct. 2, 2018.
Mangla et al., "Structure Activity Relationship of Arylidene Pyrrolo and Pyrido [2,1-n] Quinazolones as Cytotoxic Agents: Synthesis, SAR Studies, Biological Evaluation and Docking Studies", Medicinal Chemistry, vol. 9, No. 5, pp. 642-650, Jun. 1, 2013.
Pan et al., "Design, Synthesis and Evaluation of Isaindigotone Derivatives as Acetylcholinesterase and Butyrylcholinesterase Inhibitors", Bioorganic & Medicinal Chemistry Letters, Pergamon, Amsterdam, NL, vol. 18, No. 13, pp. 3790-3793, Jul. 1, 2008.
Shakhidoyatov et al., "Quinazolines XI. Condensation of Deoxyvasicinone with Aldehydes", Chemistry of Natural Compounds, vol. 13, pp. 461-463, Jan. 1, 1977.
Sutherell et al., "On the Synthesis and Reactivity of 2,3-Dihydropyrrolo[1,2-a]1uinazolin-5(1H)-ones", Synthesis, vol. 49, No. 1, pp. 135-144, Dec. 19, 2016.
Wang et al., "Design, Synthesis, and Evaluation of New Selective NM23-H2 Binders as c-MYC Transcription Inhibitors via Disruption of the NM23-H2/G-Quadruplex Interaction", Journal of Medicinal Chemistry, vol. 60, No. 16, pp. 6924-6941, Jul. 17, 2017.
Extended European Search Report in European Patent Application No. 18841404.9 dated Nov. 3, 2020.

* cited by examiner

Primary Examiner — Erich A Leeser
(74) Attorney, Agent, or Firm — Greenberg Traurig, LLP

(57) ABSTRACT

Aspects of the invention relate to compounds, pharmaceutical compositions, methods for the manufacturing of compounds and methods for treatment of various disorders mediated at least in part by one or more galectins.

29 Claims, 38 Drawing Sheets

AGS-0028

TD-139

Figure 5A
Figure 5B
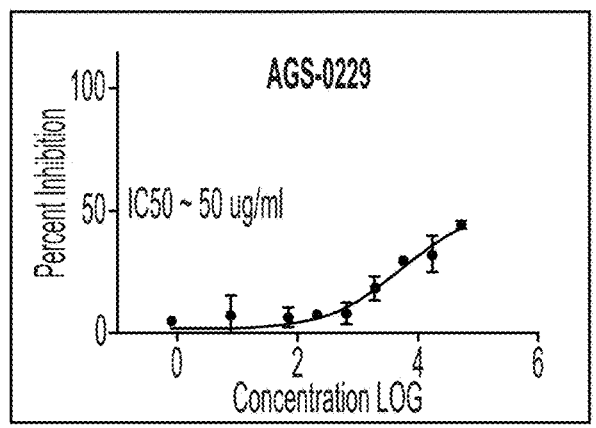
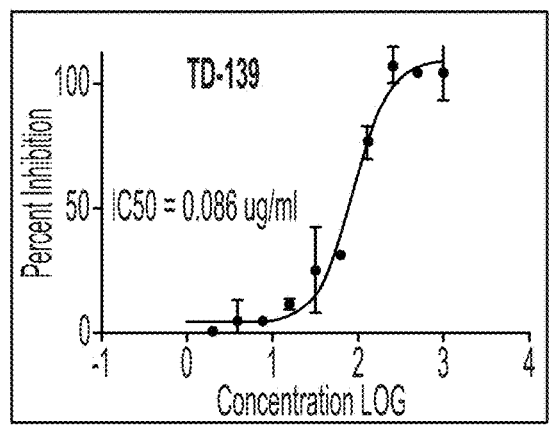

Analysis of Galectin-3 binding by a pair of specific antibodies.

Analysis of Galectin-3 binding by a protein ligand (integrin) and specific FITC tagged antibody.

S-face          F-face

TO FIG. 12B-2

| Chemical structure Formula III-IV | No | Inhibition of Gal-3 & Integrin-aMβ2 interaction | IC50 (μg/mL) |
|---|---|---|---|
|  | AGS-0150 |  | 7.9 |
|  | AGS-0149 |  | 1.2 |
|  | AGS-0155 |  | 1.08 |
|  | AGS-0143 |  | 2.3 |

| Chemical structure Formula III-IV | No | Inhibition of Gal-3 & Galectin-3 Binding Protein Interaction | IC50 (µg/mL) |
|---|---|---|---|
|  | AGS-0150 |  | 6.9 |
|  | AGS-0149 |  | 1.34 |
|  | AGS-0155 |  | 2.7 |
|  | AGS-0143 |  | -[10] |

| Chemical structure Formula III-IV | No | Inhibition of Gal-3 & TGF-beta Receptor Interaction | IC50 (μg/mL) |
|---|---|---|---|
|  | AGS-0150 |  | -[4.2] |
|  | AGS-0149 |  | 1.8 |
|  | AGS-0155 |  | 4.2 |
|  | AGS-0143 |  | >20 |
|  | AGS-164 |  | 5.1 |

| Chemical structure Formula III-IV | No | Inhibition of Gal-3 & TGF-beta Receptor-1 Interaction | IC50 (µg/mL) |
|---|---|---|---|
|  | AGS-0229 |  | 6.1 |
|  | AGS-0144 |  | 1.6 |

| Chemical structure Formula III-IV | No | Inhibition of Gal-3 & Insulin Receptor Interaction | IC50 (μg/mL) |
|---|---|---|---|
|  | AGS-O149 |  | 5.0 |
|  | AGS-O155 |  | 3.7 |
|  | AGS-O143 |  | 46.0 |
|  | AGS-O164 |  | 4.3 |
|  | AGS-O150 |  | -[3.1] |

COMPOUNDS FOR THE PREVENTION AND TREATMENT OF MEDICAL DISORDERS AND USES THEREOF

RELATED APPLICATIONS

This application is a U.S. national phase application under 35 U.S.C. 371 of PCT International Application No. PCT/US2018/045175, filed on Aug. 3, 2018, which claims the benefit of and priority to U.S. Provisional Application Ser. No. 62/540,860, filed Aug. 3, 2017, the entire disclosures of each of which are incorporated herein by reference in their entireties.

FIELD OF THE INVENTION

Aspects of the invention relate to compounds, pharmaceutical compositions, methods for the manufacturing of compounds and methods for treatment of various disorders mediated at least in part by one or more galectins. In particular, the invention relates to compounds that inhibit Gal-3 biological activities.

BACKGROUND OF THE INVENTION

Galectins are a family of S-type lectins that bind beta-galactose oligosaccharides containing glycoproteins. To date, fifteen mammalian galectins have been identified. Galectins have been associated multiple biological processes such as cell adhesion, regulation of growth, apoptosis, tumor development and other pathways in normal and pathological events. Galectin-3 (Gal-3), in particular, has been shown to be involved in inflammation, fibrosis formation, metastatic cancer including infiltration, angiogenesis, adhesion, proliferation and immunosuppression as well as systemic insulin resistance and obesity.

SUMMARY OF THE INVENTION

Aspects of the invention relate to compounds or compositions comprising a compound in an acceptable pharmaceutical carrier for parenteral or enteral administration, for use in therapeutic formulations. In some embodiments, the composition can be administered parenterally via an intravenous, subcutaneous, or oral route.

Aspects of the invention relate to compounds and method of manufacturing compounds having selective pharmacological properties to bind and specifically attenuate the Gal-3 pathological and metabolic activities. In some aspects of the invention, the compounds have reduced side effects due to non-specific interaction. In some aspects, the compounds of the invention have reduced side effects due to the attenuation of other galectins metabolic activities.

Aspects of the invention relate to compounds having an inhibitory Gal-3 biological activity. In some aspects, the compounds comprise an aryl substituent linked to a core pyrroloquinazoline-ketone specifically designed to allosterically interact and modulate and/or temper with Gal-3 interaction with glycoproteins ligands, thus directly inhibiting Gal-3 biological and pathological activities. In some aspects of the invention, the compounds can temper with pharmacodynamics properties.

Some aspects of the invention relate to compounds or pharmaceutical composition comprising a therapeutically effective dosage of allosteric interactive compounds.

Some aspects of the invention relate to methods for the manufacturing and formulating the compounds as therapeutic substances and methods for treatment of various medical disorders mediated at least in part by Gal-3 or other galectins.

In some aspects, the compounds are directed to a novel class of non-carbohydrate composite compounds that attenuate the Carbohydrate Binding Site (CRD) of human Galectin-3 (Gal-3) through an allosteric shift that modifies the carbohydrate binding site functionality.

Some aspects of the invention relate to a compound of Formula I or a pharmaceutically acceptable salt or solvate thereof or a pharmaceutical composition comprising a compound of Formula I or a pharmaceutically acceptable salt or solvate thereof

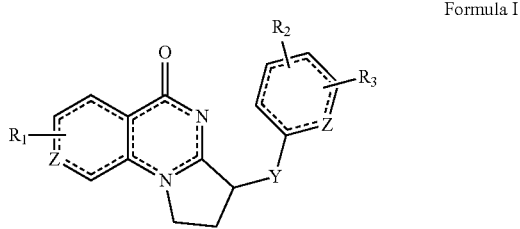

Formula I wherein (Y) linkage is (—CH═) or (—CH2-) or —CH2-X— wherein X is nitrogen, oxygen, sulfur or selenium;

wherein Z is a carbon, or a heteroatom, wherein the heteroatom is nitrogen, oxygen, sulphur, or selenium;

wherein R1 is hydrogen, oxygen, amine, carboxyl, C1-C6 alkyl, C1-C4 alkoxy, aryl, halogen, trifluoromethyl, dinitromethyl or a combination of the foregoing;

wherein R2 and R3 are independently selected from the group consisting of hydrogen, hydroxyl, amine, carboxyl, C1-C6 alkyl, C1-C4 alkoxy, and halogen.

In some embodiments, the Y linkage is —CH2-X wherein the —CH2 is linked to the pyrrolo[1,2-a]quinazolin-5-one.

In some embodiments, R2, R3 or R2 and R3 are aryl group with one or more substitutions, wherein the one or more substitution is hydroxyl, amine, C1-C6 alkyl, C1-C4 alkoxy, halogen, benzene or combinations thereof.

In some embodiments, wherein R2, R3 or R2 and R3 are fluoromethyl.

In some embodiments, the Y linkage is (—CH═).

In some embodiments, the compound is

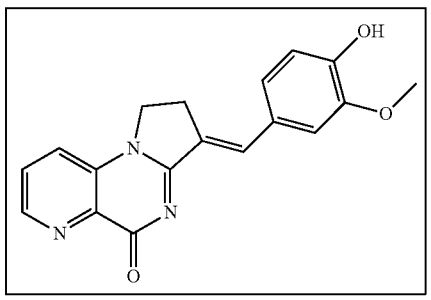 [SMILES: COc1cc(/C=C2\CCn3c2nc(=O)c2ncccc23)ccc1O]

or a pharmaceutically acceptable salt or solvate thereof.

Some aspects of the invention relate to a compound of Formula II or a pharmaceutically acceptable salt or solvate thereof or a pharmaceutical composition comprising a compound of Formula II or a pharmaceutically acceptable salt or solvate thereof

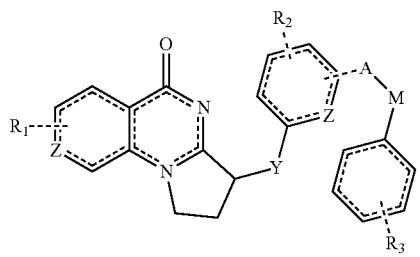

Formula II

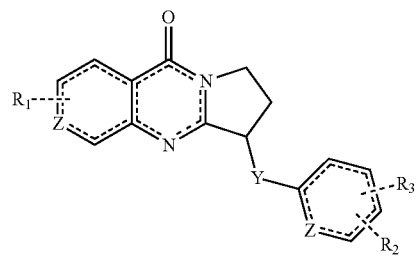

Formula III wherein A-M is a 2 atoms linkage having the structure of an amide —N(—Ra)—C(=O)—, sulfonamide —N(—H)—S(=O)—, a methylether —C(—H2)-O— methylester —C(=O)—O—, carbosulfon —C(—H2)-S(=O)(=O)—, phosphate —O—P(=O)(—OH)—, diphosphate —O—P(=O)(—O)—O—P(=O)(—O)—, Hydrazide —N(—H)—N(—H)—, selanomethylene, methoxyl, ethyl, or glycol and/or an amino acid, wherein linkage (Y) is (—CH=) or (—CH2-) or —CH2-X— wherein X is nitrogen, oxygen, sulfur or selenium;

wherein Z is a carbon, or a heteroatom wherein the heteroatom is nitrogen, oxygen sulphur, or selenium;

wherein R1 is hydrogen, oxygen, amine, carboxyl, C1-C6 alkyl, C1-C4 alkoxy, aryl, halogen, trifluoromethyl, dinitromethyl or a combination of the foregoing;

wherein R2 and R3 are independently selected from the group consisting of hydrogen, hydroxyl, amine, C1-C6 alkyl, C1-C4 alkoxy, and halogen.

In some embodiments, the Y linkage is —CH2-X wherein the —CH2 is linked to the pyrrolo[1,2-a]quinazolin-5-one.

In some embodiments, R2, R3 or R2 and R3 are aryl group with one or more substitutions, wherein the one or more substitution is hydroxyl, amine, C1-C6 alkyl, C1-C4 alkoxy, halogen, benzene or combinations thereof.

In some embodiments, wherein R2, R3 or R2 and R3 are fluoromethyl.

In some embodiments, the Y linkage is (—CH=).

In some embodiments, the compound is

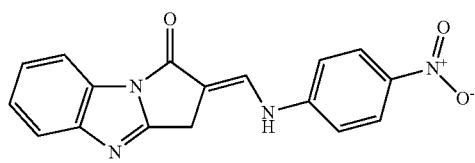 [SMILES: O=C1/C(=C/Nc2ccc([N+](=O)[O-])cc2)Cc2nc3ccccc3n21]

or a pharmaceutically acceptable salt or solvate thereof.

Some aspects of the invention relate to a compound of Formula III or a pharmaceutically acceptable salt or solvate thereof or a pharmaceutical composition comprising a compound of Formula III or a pharmaceutically acceptable salt or solvate thereof wherein Z is a carbon, or a heteroatom wherein the heteroatom is nitrogen, oxygen, sulphur or selenium;

wherein R1 is hydrogen, oxygen, amine, carboxyl, C1-C6 alkyl, C1-C4 alkoxy, aryl, halogen, trifluoromethyl, dinitromethyl or a combination of the foregoing;

wherein R2 and R3 are independently selected from the group consisting of hydrogen, hydroxyl, amine, C1-C6 alkyl, C1-C4 alkoxy, halogen, aryl group with substitutions such hydrogen, hydroxyl, amine, C1-C6 alkyl, C1-C4 alkoxy, halogen or combinations thereof; and wherein linkage (Y) is (—CH=) or (—CH2-)—) or —CH2-X—, wherein X is nitrogen, oxygen, sulfur or selenium.

In some embodiments, the Y linkage is (—CH=).

In some embodiments, the Y linkage is —CH2-X wherein the —CH2 is linked to the pyrrolo[1,2-a]quinazolin-5-one.

Some aspects of the invention relate to a compound of Formula IV or a pharmaceutically acceptable salt or solvate thereof or a pharmaceutical composition comprising a compound of Formula IV or a pharmaceutically acceptable salt or solvate thereof

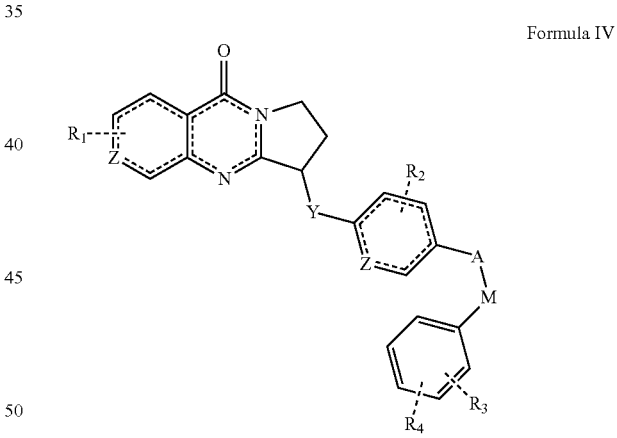

Formula IV wherein Z is a carbon, or a heteroatom wherein the heteroatom is nitrogen, oxygen Sulphur, or selenium;

wherein R1, R2, R3 and R4 are independently selected from the group consisting of CO, SO2, SO, PO2, PO, CH, Hydrogen, hydrophobic linear and cyclic hydrocarbons including heterocyclic substitutions of molecular weight of about 10-200 D;

wherein linkage (Y) is methylidene (—CH=) or methylene (—CH2-)—) or —CH2-X—, wherein X is nitrogen, oxygen, sulfur or selenium;

wherein the A-M linkage being at least 2 atoms linkage having the structure of. amide —N(—Ra)—C(=O)—, sulfonamide —N(—H)—S(=O2)-, a methylether —C(—H2)-O— methylester —C(=O)—O—, carbosulfon —C(—H2)-S(=O)(=O)—, phosphate —O—P (=O)(—OH)—, diphosphate —O—P(=O)(—O)—O—P(=O)(—O)—, Hydrazide —N(—H)—N(—H)—, selanomethylene, methoxyl, ethyl, glycol; and/or an amino acid.

In some embodiments, the Y linkage is —CH2-X wherein the —CH2 is linked to the pyrrolo[1,2-a]quinazolin-5-one.

In some embodiments, the Y linkage is (—CH=).

In some embodiments, the compound is shown below or a pharmaceutically acceptable salt or solvate thereof

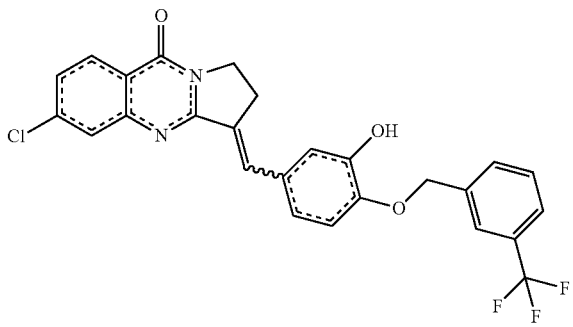

In some embodiments, the wherein the hydrophobic linear and cyclic hydrocarbons comprise one of:

a) an alkyl group of at least 4 carbons, an alkenyl group of at least 4 carbons, an alkyl group of at least 4 carbons substituted with a carboxy group, an alkenyl group of at least 4 carbons substituted with a carboxy group, an alkyl group of at least 4 carbons substituted with an amino group, an alkenyl group of at least 4 carbons substituted with an amino group, an alkyl group of at least 4 carbons substituted with both an amino and a carboxy group, an alkenyl group of at least 4 carbons substituted with both an amino and a carboxy group, and an alkyl group substituted with one or more halogens, b) a phenyl group, or a phenyl group substituted with at least one carboxy group, a phenyl group substituted with at least one halogen, a phenyl group substituted with at least one alkoxy group, a phenyl group substituted with at least one nitro group, a phenyl group substituted with at least one sulfo group, a phenyl group substituted with at least one amino group, a phenyl group substituted with at least one alkylamino group, a phenyl group substituted with at least one dialkylamino group, a phenyl group substituted with at least one hydroxy group, a phenyl group substituted with at least one carbonyl group and a phenyl group substituted with at least one substituted carbonyl group.

c) a naphthyl group, or a naphthyl group substituted with at least one carboxy group, a naphthyl group substituted with at least one halogen, a naphthyl group substituted with at least one alkoxy group, a naphthyl group substituted with at least one nitro group, a naphthyl group substituted with at least one sulfo group, a naphthyl group substituted with at least one amino group, a naphthyl group substituted with at least one alkylamino group, a naphthyl group substituted with at least one dialkylamino group, a naphthyl group substituted with at least one hydroxy group, a naphthyl group substituted with at least one carbonyl group and a naphthyl group substituted with at least one substituted carbonyl group.

d) a heteroaryl group, or a heteroaryl group substituted with at least one carboxy group, a heteroaryl group substituted with at least one halogen, a heteroaryl group substituted with at least one alkoxy group, a heteroaryl group substituted with at least one nitro group, a heteroaryl group substituted with at least one sulfo group, a heteroaryl group substituted with at least one amino group, a heteroaryl group substituted with at least one alkylamino group, a heteroaryl group substituted with at least one dialkylamino group, a heteroaryl group substituted with at least one hydroxy group, a heteroaryl group substituted with at least one carbonyl group and/a heteroaryl group substituted with at least one substituted carbonyl group, or a combination thereof.

In some embodiments, the compound is a compound of Table 1 or a pharmaceutically acceptable salt or solvate thereof

TABLE 1

Example 1A:
Y = methylidene
AGS-0028
E and Z isomers

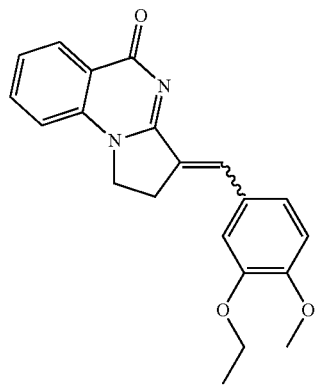 [SMILES: CCOc1cc(C=C2CCn3c2nc(=O)c2ccccc23)ccc1OC]

3-[(4-ethoxy-3-methoxyphenyl)methylidene]-1H,2H,3H,5H-pyrrolo[1,2-a]quinazolin-5-one Example 1B:
Y = methylidene
AGS-0028 - E isomer

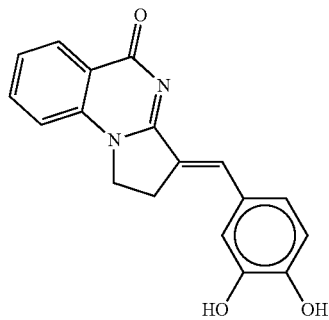

(3E)-3-(3,4-dihydroxybenzylidene)-2,3-dihydropyrrolo[1,2-a]quinazolin-5(1H)-one

Example 1C:
Y = methylidene
AGS-0028 - Z isomer

TABLE 1-continued

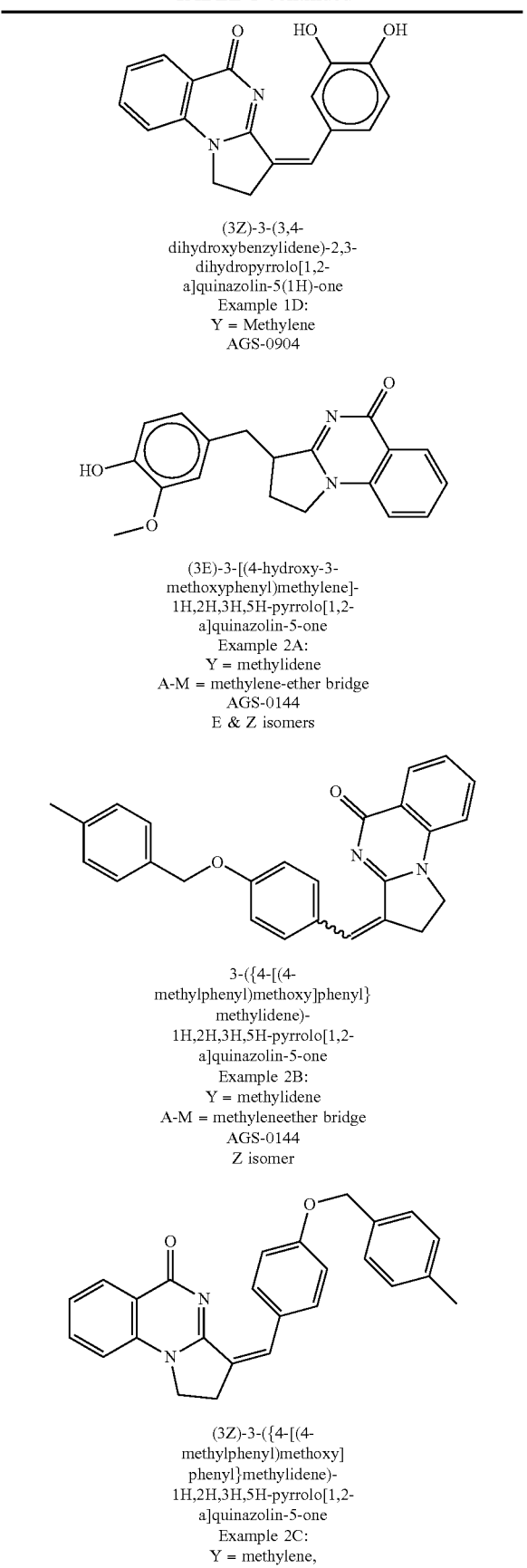

(3Z)-3-(3,4-dihydroxybenzylidene)-2,3-dihydropyrrolo[1,2-a]quinazolin-5(1H)-one
Example 1D:
Y = Methylene
AGS-0904

(3E)-3-[(4-hydroxy-3-methoxyphenyl)methylene]-1H,2H,3H,5H-pyrrolo[1,2-a]quinazolin-5-one
Example 2A:
Y = methylidene
A-M = methylene-ether bridge
AGS-0144
E & Z isomers 3-({4-[(4-methylphenyl)methoxy]phenyl}methylidene)-1H,2H,3H,5H-pyrrolo[1,2-a]quinazolin-5-one
Example 2B:
Y = methylidene
A-M = methyleneether bridge
AGS-0144
Z isomer (3Z)-3-({4-[(4-methylphenyl)methoxy]phenyl}methylidene)-1H,2H,3H,5H-pyrrolo[1,2-a]quinazolin-5-one
Example 2C:
Y = methylene, TABLE 1-continued A-M = methylene-ether bridge
AGS-0906

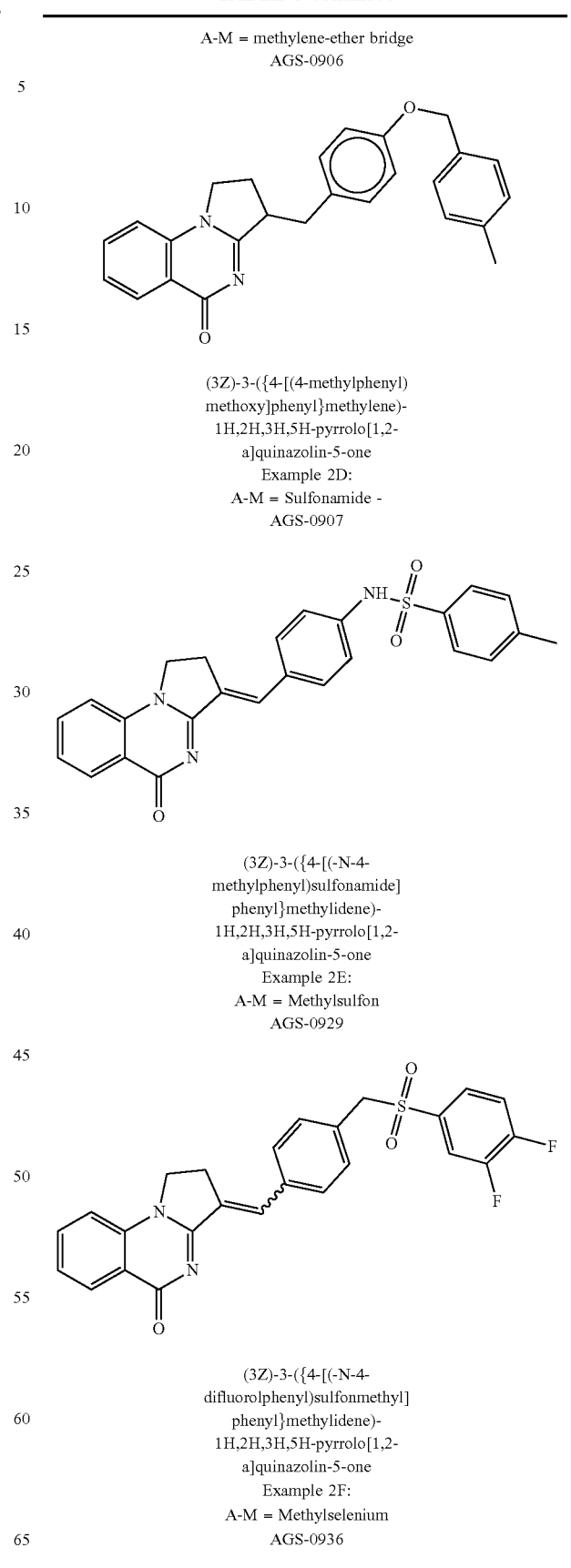

(3Z)-3-({4-[(4-methylphenyl)methoxy]phenyl}methylene)-1H,2H,3H,5H-pyrrolo[1,2-a]quinazolin-5-one
Example 2D:
A-M = Sulfonamide -
AGS-0907

(3Z)-3-({4-[(-N-4-methylphenyl)sulfonamide]phenyl}methylidene)-1H,2H,3H,5H-pyrrolo[1,2-a]quinazolin-5-one
Example 2E:
A-M = Methylsulfon
AGS-0929

(3Z)-3-({4-[(-N-4-difluorolphenyl)sulfonmethyl]phenyl}methylidene)-1H,2H,3H,5H-pyrrolo[1,2-a]quinazolin-5-one
Example 2F:
A-M = Methylselenium
AGS-0936

TABLE 1-continued

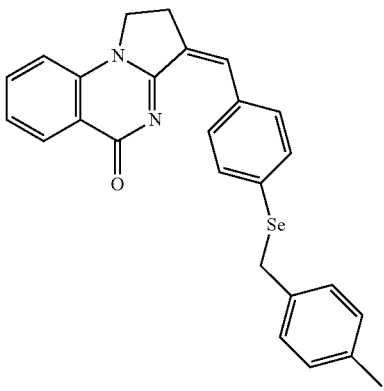 [SMILES: Cc1ccc(C[Se]c2ccc(/C=C3/CCn4c3nc(=O)c3ccccc34)cc2)cc1]

(3Z)-3-({4-[(4-methylphenyl)selanomethylene]phenyl}methylidene)-1H,2H,3H,5H-pyrrolo[1,2-a]quinazolin-5-one
Linear QZ
Example 3A: Y = methylidene
AGS-1011

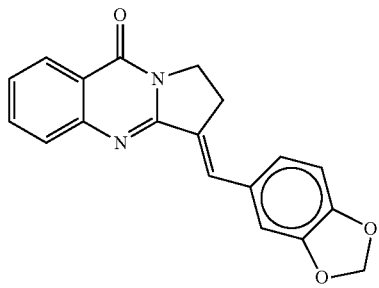

(3E)-3-[(2H-1,3-benzodioxol-5-yl)methylidene]-1H,2H,3H,9H-pyrrolo[2,1-b]quinazolin-9-one
Example B: Z = Sulfate
AGS-1021

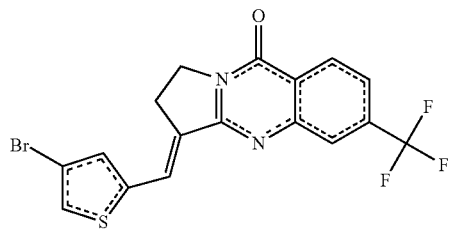

(3E)-3-[(4-bromothiophen-2-yl)methylidene]-6-(trifluoromethyl)-1H,2H,3H,9H-pyrrolo[2,1-b]quinazolin-9-one
Example 4A: Y = methylidene
A-M = Methoxyl bridge
AGS-1101

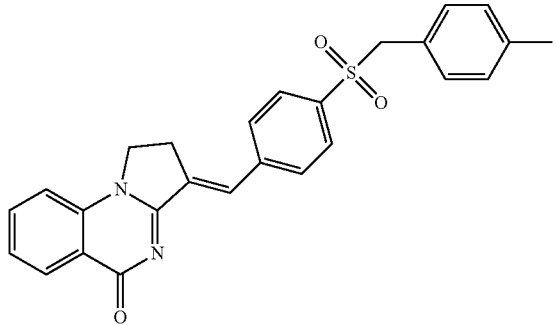

In some embodiments, the compound is a compound of Table 6 or a pharmaceutically acceptable salt or solvate thereof

TABLE 6

| GS Codes | Manufacturing codes | Structures |
|---|---|---|
| AGS-0928 | GTJC-144-009 | 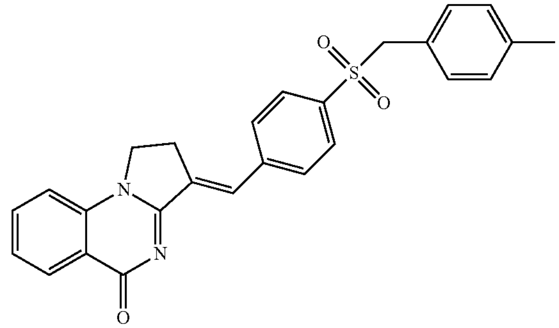 [SMILES: Cc1ccc(CS(=O)(=O)c2ccc(/C=C3\CCn4c3nc(=O)c3ccccc34)cc2)cc1] |

TABLE 6-continued
| GS Codes | Manufacturing codes | Structures |
|---|---|---|
| AGS-0925 | GTJC-144-006 | 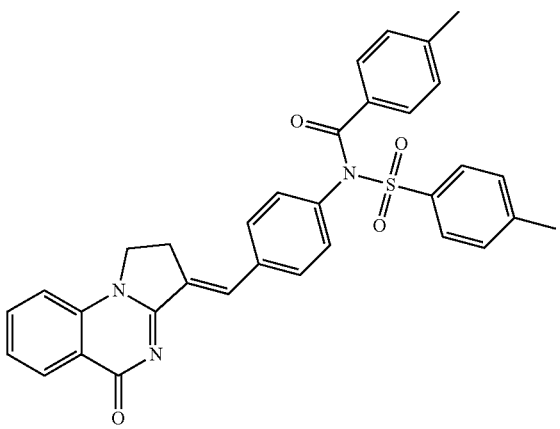 [SMILES: Cc1ccc(C(=O)N(c2ccc(/C=C3\CCn4c3nc(=O)c3ccccc34)cc2)S(=O)(=O)c2ccc(C)cc2)cc1] |
| AGS-0907 | GTJC-144-008 | 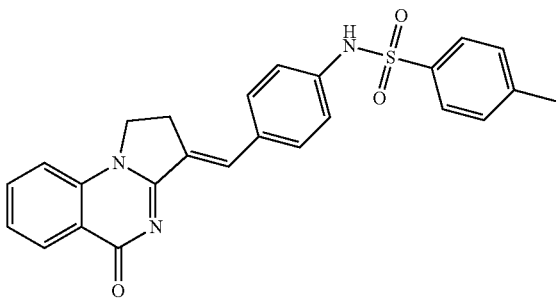 [SMILES: Cc1ccc(S(=O)(=O)Nc2ccc(/C=C3\CCn4c3nc(=O)c3ccccc34)cc2)cc1] |
| AGS-0921 | GTJC-144-008-1 | 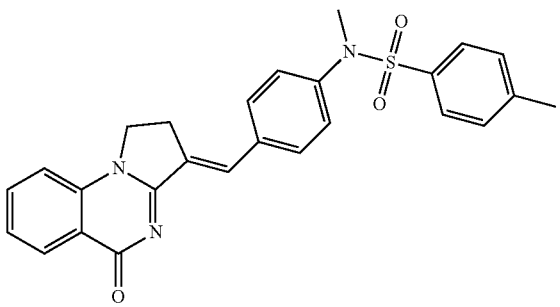 [SMILES: Cc1ccc(S(=O)(=O)N(C)c2ccc(/C=C3\CCn4c3nc(=O)c3ccccc34)cc2)cc1] |
| AGS-0926 | GTJC-028-12-2 | 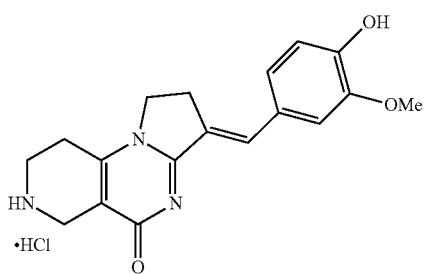  GTJC-028-12-2 |

TABLE 6-continued

| GS Codes | Manufacturing codes | Structures |
|---|---|---|
| AGS-0923 | GTJC-028-021 | 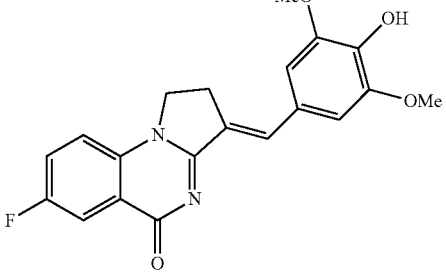 |
| AGS-0924 | GTJC-028-022 | 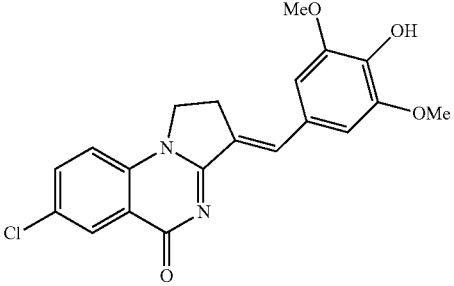 [SMILES: COc1cc(/C=C2\CCn3c2nc(=O)c2cc(Cl)ccc23)cc(OC)c1O] |
| AGS-0934 | GTJC-028-023 | 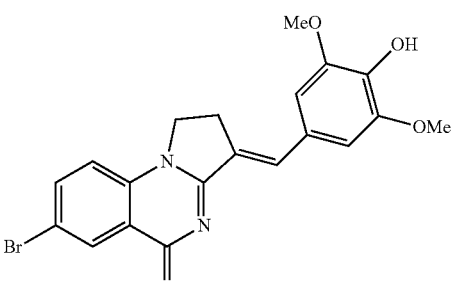 |

In some embodiments, the compound has a binding affinity of about 5 nM to 20 µM for Galectin-3.

In some embodiments, the compound is in a crystalline form or in a free form. The free form can be an anhydrate or a hydrate.

In some embodiments, the compound binds Galectin 3 with higher specificity than Galectin 1, Galectin 8, Galectin 9 or other galectins.

In some embodiments, the compound modulates Gal-3 binding to Insulin receptor and Insulin Like Growth Factor 1 Receptor.

Aspects of the invention relate to a composition comprising a therapeutically effective amount of the compound described herein, and a pharmaceutically acceptable adjuvant, excipient, formulation carrier or combinations thereof.

In some embodiments, the composition comprises a therapeutically effective amount of the compound described herein, and a therapeutically effective amount of an anti-inflammatory drug, anti-fibrosis drug, pharmaceutical drug, nutraceutical drug, supplement, or combinations thereof.

In some embodiments, the composition comprises the compound in an acceptable pharmaceutical carrier for use in enteral or parenteral administration.

In some embodiments, a pharmaceutical composition comprising the compound in an acceptable pharmaceutical carrier can be formulated for use in oral, intravenous or subcutaneous administration.

Aspects of the invention relate to a method of treatment of a disease in a subject in need thereof, comprising administering a therapeutically effective amount of a pharmaceutical composition comprising at least one compound described herein.

In some embodiments, the disease is a disorder related to pathological disease due to elevated galectin-3.

In some embodiments, the disease is alcoholic or viral steatohepatitis a nonalcoholic steatohepatitis, fibrosis, cirrhosis, inflammatory disorder, metabolic disorder, insulin resistance, autoimmune disorder, neoplastic condition, metabolic disorder or cancer.

In some embodiments, the inflammatory disorder is inflammatory bowel disease, Crohn's disease, multiple sclerosis, Systemic Lupus Erythematosus, arthritis, rheumatoid arthritis, asthma or ulcerative colitis.

In some embodiments, the fibrosis is liver fibrosis, kidney fibrosis, lung fibrosis, or heart fibrosis.

In some embodiments, the autoimmune disorder is rheumatoid arthritis, skin disease or multiple sclerosis.

In some embodiments, the disease is heart failure, arrhythmias, or uremic cardiomyopathy.

In some embodiments, the disease is a chronic kidney and idiopathic lung diseases.

In some embodiments, the disease is a skin autoimmune, proliferative and fibrotic skin disorder, optionally psoriasis or atopic dermatitis.

In some embodiments, the neoplastic condition is a benign or malignant neoplastic disease.

Aspects of the invention relates to method for treating systemic insulin resistance associated with type 1 diabetes and obesity.

Aspects of the invention relates to method for treating systemic insulin resistance associated with type 2 diabetes mellitus (T2DM).

Aspects of the invention relates to method for treating systemic insulin resistance associated with obesity, gestational diabetes or prediabetes.

In some embodiments, the treatment with the compound or composition described herein restores sensitivity of cells to insulin activity.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

FIGS. 5A and 5B demonstrates an inhibition of FP by the galactose derivative [TD-149] as comparing to an allosteric inhibitor AGS-0229 according to embodiments of the invention. Weak signal of FP (Fluorescent Polarization) by the allosteric galectin-3 inhibitor (FIG. 5A, AGS-0229) as compared with the strong signal generated by a galactoside derivative [FIG. 5B, TD-139] that bind directly to the CRD site.

FIG. 12A shows that the compounds described herein may have also effect the CRD by increase its affinity to the glycoproteins' receptors.

FIG. 12D shows that the compounds described herein can also increase the CRD affinity to the glycoprotein' receptors as shown in this experiment with AGS-0143.

FIG. 12E shows that the compounds described herein can also increase the CRD affinity to the glycoprotein' receptors as shown in this experiment with AGS-0150.

FIG. 12F shows that the compounds described herein can also increase the CRD affinity to the glycoprotein' receptors as shown in this experiment with AGS-0150.

FIG. 12E shows that the compounds described herein can also increase the CRD affinity to the glycoprotein' receptors as shown in this experiment with AGS-0903.

DETAILED DESCRIPTION OF THE INVENTION

Figure 1:
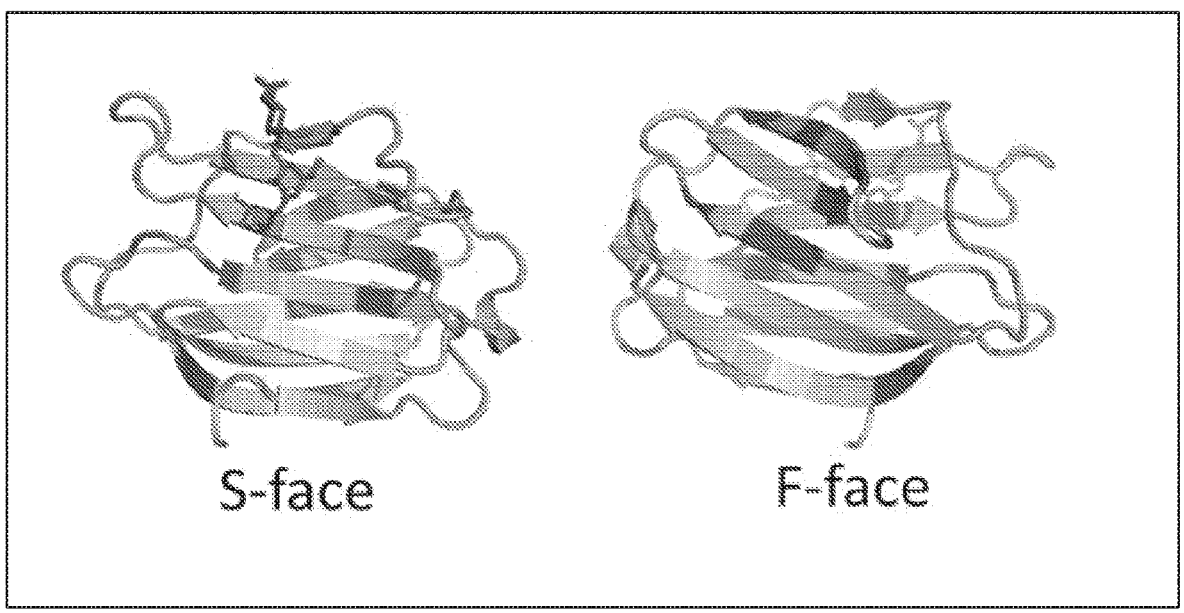
FIG. 1 depicts a high-definition 3D structure of Gal-3 illustrate the S face with the Carbohydrate Recognition Domain (CRD) binding pocket with lactose (blue) and the F Face where potential sites for allosteric interaction site, the binding target for the compounds described herein according to embodiments of the invention.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Citation of documents herein is not intended as an admission that any of the documents cited herein is pertinent prior art, or an admission that the cited documents are considered material to the patentability of the claims of the present application.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the meaning of "a," "an," and "the" include plural references.

Unless otherwise specified, all percentages expressed herein are weight/weight.

Galectins

Galectins (also known as galaptins or S-lectins) are a family of lectins which bind beta-galactoside. Galectin as a general name was proposed in 1994 for a family of animal lectins (Barondes, S. H., et al.: Galectins: a family of animal beta-galactoside-binding lectins. Cell 76, 597-598, 1994). The family is defined by having at least one characteristic carbohydrate recognition domain (CRD) with an affinity for beta-galactosides and sharing certain sequence elements. Further structural characterization segments the galectins into three subgroups including: (1) galectins having a single CRD, (2) galectins having two CRDs joined by a linker peptide, and (3) a group with one member (galectin-3) which has one CRD joined to a different type of N-terminal domain. The galectin carbohydrate recognition domain is a beta-sandwich of about 135 amino acids. The two sheets are slightly bent with 6 strands forming the concave side, also called the S-face, and 5 strands forming the convex side, the F-face). The concave side forms a groove in which carbohydrate is bound (Leffler H, Carlsson S, Hedlund M, Qian Y, Poirier F (2004). "Introduction to galectins". Glycoconj. J. 19 (7-9): 433-40).

A wide variety of biological phenomena have been shown to be related to galectins, including development, differentiation, morphogenesis, tumor metastasis, apoptosis, RNA splicing, and many others.

At least fifteen mammalian galectin proteins have been identified which have one or two carbohydrate domains in tandem. Galectin 3 (Gal-3), also known as MAC2, is a galectin encoded by a single gene, LGALS3.

Galectin proteins are markedly increased in a number of animal and human disease states, including but not limited to diseases associated with inflammation, fibrosis, autoimmunity, and neoplasia. Galectins have been directly implicated in the disease pathogenesis, as described below. For example, diseases states that may be dependent on galectins include, but are not limited to, acute and chronic inflammation, allergic disorders, asthma, dermatitis, autoimmune disease, inflammatory and degenerative arthritis, immune-mediated neurological disease, fibrosis of multiple organs (including but not limited to liver, lung, kidney, pancreas, and heart), inflammatory bowel disease, atherosclerosis, heart failure, ocular inflammatory disease, a large variety of cancers.

In addition to disease states, galectins are important regulatory molecules in modulating the response of immune cells to vaccination, exogenous pathogens and cancer cells.

Accordingly, there is a need to provide compounds and method of manufacturing compounds having selective pharmacological properties to bind and specifically attenuate the Gal-3 pathological and metabolic activities. In some embodiments, these compounds can have have reduced side effects due to non-specific interaction and attenuate other galectins metabolic activities.

Compounds

Aspects of the invention relate to compounds of Formula I or salts or solvates thereof:

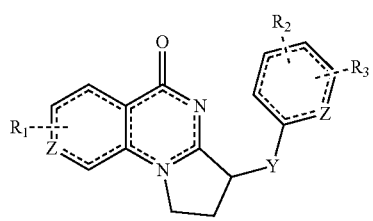

Formula I

Aspects of the invention relate to compounds having the structure of formula I, wherein a core pyrroloquinazoline-ketone structure is first linked to a selected aryl compounds through a single atom bridge (Y). In some embodiments, the aryl group has substituents (R2 and R3) which enable a Gal-3 allosteric binding which alter the CRD binding characteristics. In some embodiments, the linkage (Y) a methylidene (—CH═) could be of E or Z isomers (See Examples 1A, B and C of Table 1).

In some embodiments, the linkage (Y) is further selected also from a single atom of methylene (—CH2-) or —Se—, —S—, —N— or —O— (See example 1D of Table 1).

In some embodiments, Z indicates heteroatoms that are incorporated into the molecules such as nitrogen, oxygen or sulphur.

In some embodiments, the compound substitution R1 of Formula I is selected from hydrogen, oxygen, amine, carboxyl, C1-C6 alkyl, C1-C4 alkoxy, aryl, halogens, trifluoromethyl, dinitromethyl or combinations of the foregoing. In some embodiments, R2 and R3 are individually and independently selected from the group consisting of hydrogen, hydroxyl, amine, C1-C6 alkyl, C1-C4 alkoxy, and halogens.

In some embodiments, R2 and/or R3 independently are aryl group with substitutions such hydrogen, hydroxyl, amine, C1-C6 alkyl, C1-C4 alkoxy, halogens, benzene or combinations thereof. In some embodiments, R1 and/or R2 are fluoromethyl, as illustrated in Formula II (See examples 2A, 2B, and 2C of Table 1).

Some aspects of the invention relate to a compound of Formula I or a pharmaceutically acceptable salt or solvate thereof or a pharmaceutical composition comprising a compound of Formula I or a pharmaceutically acceptable salt or solvate thereof

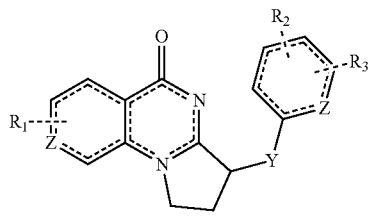

Formula I wherein (Y) linkage is (—CH═) or (—CH2-) or —CH2-X— wherein X is nitrogen, oxygen, sulfur or selenium;

wherein Z is a carbon, or a heteroatom, wherein the heteroatom is nitrogen, oxygen, sulphur, or selenium;

wherein R1 is hydrogen, oxygen, amine, carboxyl, C1-C6 alkyl, C1-C4 alkoxy, aryl, halogen, trifluoromethyl, dinitromethyl or a combination of the foregoing;

wherein R2 and R3 are independently selected from the group consisting of hydrogen, hydroxyl, amine, carboxyl, C1-C6 alkyl, C1-C4 alkoxy, and halogen.

In some embodiments, the Y linkage is —CH2-X wherein the —CH2 is linked to the pyrrolo[1,2-a]quinazolin-5-one.

In some embodiments, R2, R3 or R2 and R3 are aryl group with one or more substitutions, wherein the one or more substitution is hydroxyl, amine, C1-C6 alkyl, C1-C4 alkoxy, halogen, benzene or combinations thereof.

In some embodiments, R2, R3 or R2 and R3 are fluoromethyl.

In some embodiments, R2, R3 or R2 and R3 are hydroxyl, C1-C4 alkoxy or combinations thereof.

In some embodiments, the compound is

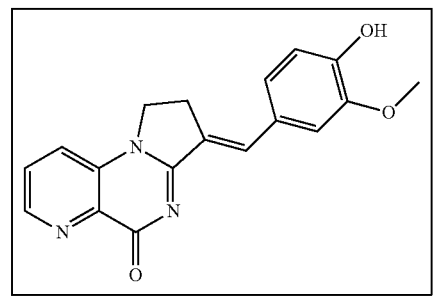 [SMILES: COc1cc(/C=C2\CCn3c2nc(=O)c2ncccc23)ccc1O]

or a pharmaceutically acceptable salt or solvate thereof.

Aspects of the invention relate to compounds having the structure of Formula II or a pharmaceutically acceptable salt or solvate thereof.

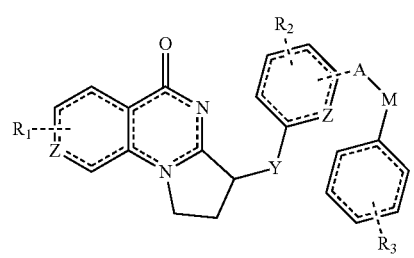

Formula II

In some embodiments, the allosteric activity can be enhanced by the property of the A-M linkage and the properties of the aryl group substituents with $IC_{50}$ range from 5 ηM to 20 μM.

In some embodiments, A-M can be a 2 atoms linkage having the structure of an amide —N(—Ra)—C(═O)—, sulfonamide —N(—H)—S(═O2)-, a methylether —C(—H2)-O— methylester —C(═O)—O—, carbosulfon —C(—H2)-S(═O)(═O)—, phosphate —O—P(═O)(—OH)—, diphosphate —O—P(═O)(—O)—O—P(═O)(—O)—, Hydrazide —N(—H)—N(—H)—, selanomethylene, methoxyl, ethyl, glycol and/or an amino acid.

In some embodiments, the Y linkage is —CH2-X wherein the —CH2 is linked to the pyrrolo[1,2-a]quinazolin-5-one.

In some embodiments, R2, R3 or R2 and R3 are aryl group with one or more substitutions, wherein the one or more substitution is hydroxyl, amine, C1-C6 alkyl, C1-C4 alkoxy, halogen, benzene or combinations thereof.

In some embodiments, wherein R2, R3 or R2 and R3 are fluoromethyl.

In some embodiments, the A-M entity in Formula II can be a 2-atom linkage having the structure of amide, sulfonamide, selanomethylene, methoxyl, methylester, ethyl, glycol and similar (See examples 2D, 2E and 2F of Table 1).

Aspects of the invention are also directed to compounds having the structure of formula II or salts or solvates thereof, wherein the compounds have a core Pyrroloquinazoline-ketone structure having a linear Pyrroloquinazoline-ketone structure. The linkage (Y) can be further selected from a single atom bridge of methylene (—CH2-) or methylidene (—CH═) or one of —Se—, —S—, —N— or —O— (See examples 3A and 3B of Table 1).

Aspects of the invention are also directed to compounds having the structure of formula III or salts or solvates thereof.

Formula III

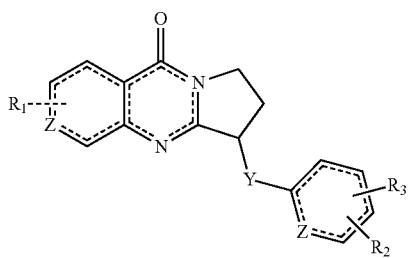

In some embodiments, Z indicates heteroatoms that are incorporated into the molecules such as nitrogen, oxygen or sulphur. In some embodiments, R1 is selected from hydrogen, hydroxyl, amine, C1-C6 alkyl, C1-C4 alkoxy, halogens and trifluoromethyl. In some embodiments, R2 and R3 are individually and independently selected from the group consisting of hydrogen, hydroxyl, amine, C1-C6 alkyl, C1-C4 alkoxy, halogens and aryl group with substitutions such hydrogen, hydroxyl, amine, C1-C6 alkyl, C1-C4 alkoxy, halogens and combinations thereof.

In some embodiments, the linkage (Y) is (—CH═) or (—CH2-)—) or —CH2-X—, wherein X is nitrogen, oxygen, sulfur or selenium. In some embodiments, the Y linkage is —CH2-X wherein the —CH2 is linked to the pyrrolo[1,2-a]quinazolin-5-one.

Aspects of the invention are directed to compounds having the structure as illustrated in Formula IV or salts or solvates thereof.

Formula IV

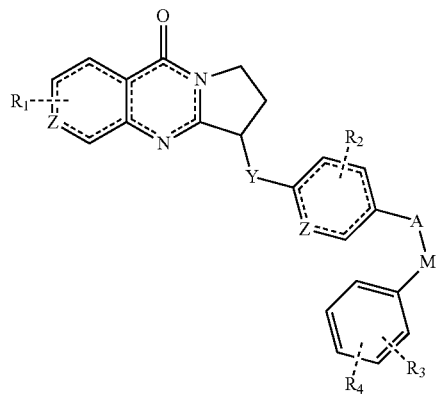

In some embodiments, the allosteric activity can be enhanced by the property of the A-M Linkage and the properties of the $2^{nd}$ aryl group substituents.

In some embodiments, the A-M entity in Formula IV can be a 2 atoms linkage having the structure of amide, sulfonamide, selanomethylene, methoxyl, methylester, ethyl, glycol and bi-atom linkages.

Aspects of the invention are also directed to compounds having the structure of formula IV or salts or solvates thereof.

In some embodiments, Z is a carbon, or a heteroatom wherein the heteroatom is nitrogen, oxygen Sulphur, or selenium; the linkage (Y) is methylidene (—CH═) or methylene (—CH2-)—) or —CH2-X—, wherein X is nitrogen, oxygen, sulfur or selenium; the A-M linkage being at least 2 atoms linkage having the structure of amide —N(—Ra)—C(═O)—, sulfonamide —N(—H)—S(═O2)-, a methylether —C(—H2)-O— methylester —C(═O)—O—, carbosulfon —C(—H2)-S(═O)(═O)—, phosphate —O—P(═O)(—OH)—, diphosphate —O—P(═O)(—O)—O—P(═O)(—O)—, Hydrazide —N(—H)—N(—H)—, selanomethylene, methoxyl, ethyl, glycol; and/or an amino acid.

In some embodiments, R1, R2, R3 and R4 are independently selected from the group consisting of CO, SO2, SO, PO2, PO, CH, Hydrogen, hydrophobic linear and cyclic hydrocarbons including heterocyclic substitutions of molecular weight of about 10-200 D In some embodiments, the compound has the structure of the compound shown in example 4A of Table 1)

In some embodiments, the hydrophobic linear and cyclic hydrocarbons can comprise one of:
a) an alkyl group of at least 4 carbons, an alkenyl group of at least 4 carbons, an alkyl group of at least 4 carbons substituted with a carboxy group, an alkenyl group of at least 4 carbons substituted with a carboxy group, an alkyl group of at least 4 carbons substituted with an amino group, an alkenyl group of at least 4 carbons substituted with an amino group, an alkyl group of at least 4 carbons substituted with both an amino and a carboxy group, an alkenyl group of at least 4 carbons substituted with both an amino and a carboxy group, and an alkyl group substituted with one or more halogens,
b) a phenyl group, or a phenyl group substituted with at least one carboxy group, a phenyl group substituted with at least one halogen, a phenyl group substituted with at least one alkoxy group, a phenyl group substituted with at least one nitro group, a phenyl group substituted with at least one sulfo group, a phenyl group substituted with at least one amino group, a phenyl group substituted with at least one alkylamino group, a phenyl group substituted with at least one dialkylamino group, a phenyl group substituted with at least one hydroxy group, a phenyl group substituted with at least one carbonyl group and a phenyl group substituted with at least one substituted carbonyl group.

c) a naphthyl group, or a naphthyl group substituted with at least one carboxy group, a naphthyl group substituted with at least one halogen, a naphthyl group substituted with at least one alkoxy group, a naphthyl group substituted with at least one nitro group, a naphthyl group substituted with at least one sulfo group, a naphthyl group substituted with at least one amino group, a naphthyl group substituted with at least one alkylamino group, a naphthyl group substituted with at least one dialkylamino group, a naphthyl group substituted with at least one hydroxy group, a naphthyl group substituted with at least one carbonyl group and a naphthyl group substituted with at least one substituted carbonyl group.

d) a heteroaryl group, or a heteroaryl group substituted with at least one carboxy group, a heteroaryl group substituted with at least one halogen, a heteroaryl group substituted with at least one alkoxy group, a heteroaryl group substituted with at least one nitro group, a heteroaryl group substituted with at least one sulfo group, a heteroaryl group substituted with at least one amino group, a heteroaryl group substituted with at least one alkylamino group, a heteroaryl group substituted with at least one dialkylamino group, a heteroaryl group substituted with at least one hydroxy group, a heteroaryl group substituted with at least one carbonyl group and/a heteroaryl group substituted with at least one substituted carbonyl group, or a combination thereof.

Without being bound to these examples other derivatives and/or substitutions would be active pharmaceuticals targeting galectins. Further examples of compounds are given in Table 1.

TABLE 1

EXAMPLE OF ALLOSTERIC GALECTIN SHIFTING COMPOUNDS (AGS):

Example 1A:
Y = methylidene
AGS-0028
E and Z isomers

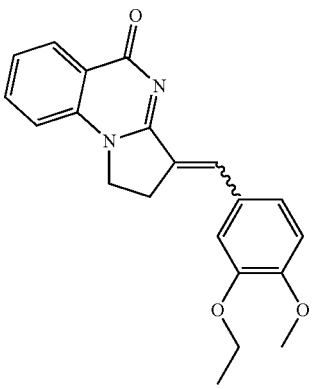 [SMILES: CCOc1cc(C=C2CCn3c2nc(=O)c2ccccc23)ccc1OC]

3-[(4-ethoxy-3-methoxyphenyl)methylidene]-1H,2H,3H,5H-pyrrolo[1,2-a]quinazolin-5-one TABLE 1-continued

EXAMPLE OF ALLOSTERIC GALECTIN SHIFTING COMPOUNDS (AGS):

Example 1B:
Y = methylidene
AGS-0028 - E isomer

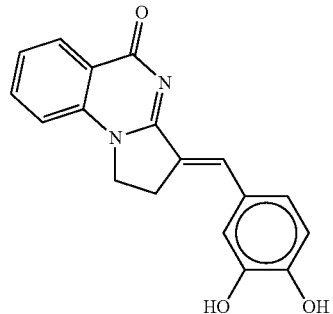

(3E)-3-(3,4-dihydroxybenzylidene)-2,3-dihydropyrrolo[1,2-a]quinazolin-5(1H)-one

Example 1C:
Y = methylidene
AGS-0028 - Z isomer

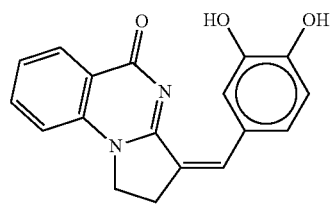

(3Z)-3-(3,4-dihydroxybenzylidene)-2,3-dihydropyrrolo[1,2-a]quinazolin-5(1H)-one

Example 1D:
Y = Methylene
AGS-0904

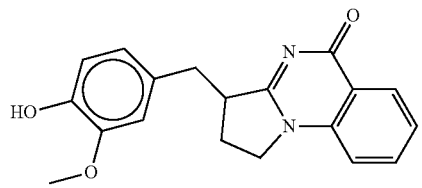

(3E)-3-[(4-hydroxy-3-methoxyphenyl)methylene]-1H,2H,3H,5H-pyrrolo[1,2-a]quinazolin-5-one Example 2A:
Y = methylidene
A-M = methylene-ethoer bridge
AGS-0144
E & Z isomers

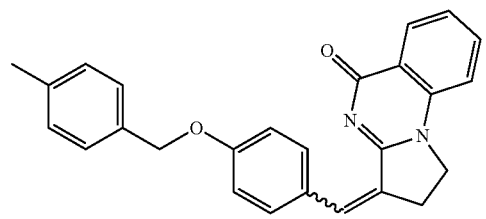 [SMILES: Cc1ccc(COc2ccc(C=C3CCn4c3nc(=O)c3ccccc34)cc2)cc1]

3-({4-[(4-methylphenyl)methoxy]phenyl}

TABLE 1-continued

EXAMPLE OF ALLOSTERIC GALECTIN SHIFTING COMPOUNDS (AGS):

methylidene)-
1H,2H,3H,5H-pyrrolo[1,2-a]quinazolin-5-one
Example 2B:
Y = methylidene
A-M = methylene-ethoer bridge
AGS-0144
Z isomer

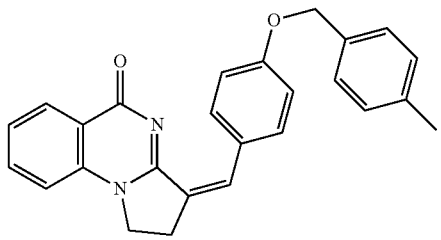 [SMILES: Cc1ccc(COc2ccc(/C=C3/CCn4c3nc(=O)c3ccccc34)cc2)cc1]

(3Z)-3-({4-[(4-methylphenyl)methoxy]phenyl}methylidene)-
1H,2H,3H,5H-pyrrolo[1,2-a]quinazolin-5-one
Example 2C:
Y = methylene,
A-M = methylene-ether bridge
bridge
AGS-0906

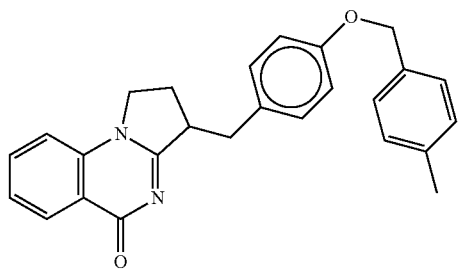

(3Z)-3-({4-[(4-methylphenyl)methoxy]phenyl}methylene)-
1H,2H,3H,5H-pyrrolo[1,2-a]quinazolin-5-one
Example 2D:
A-M = Sulfonamide -
AGS-0907

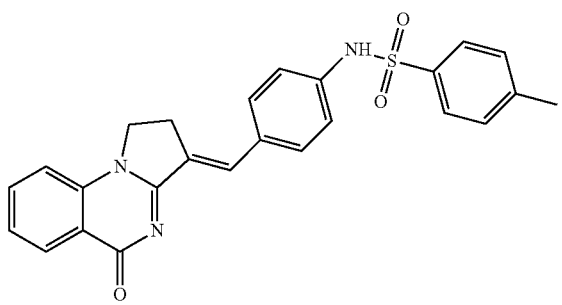 [SMILES: Cc1ccc(S(=O)(=O)Nc2ccc(/C=C3\CCn4c3nc(=O)c3ccccc34)cc2)cc1]

(3Z)-3-({4-[(-N-4-methylphenyl)sulfonamide]phenyl}methylidene)-
1H,2H,3,5H-pyrrolo[1,2-a]quinazolin-5-one
Example 2E:
A-M = Methylsulfon
AGS-0929

TABLE 1-continued

EXAMPLE OF ALLOSTERIC GALECTIN SHIFTING COMPOUNDS (AGS):

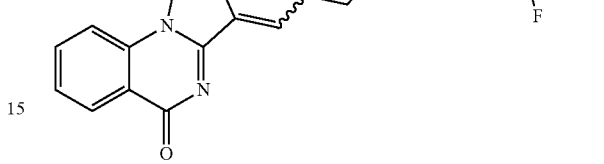

(3Z)-3-({4-[(-N-4-difluorolphenyl)sulfonmethyl]phenyl}methylidene)-
1H,2H,3H,5H-pyrrolo[1,2-a]quinazolin-5-one
Example 2F:
A-M = Methylselenium
AGS-0936

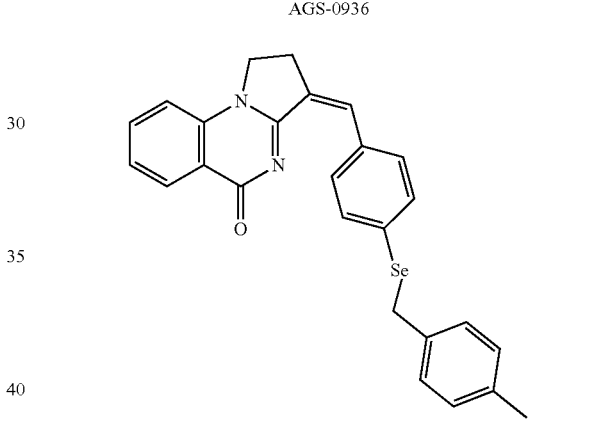

(3Z)-3-({4-[(4-methylphenyl)selanomethylene]phenyl}methylidene)-1H,2H,3H,5H-pyrrolo[1,2-a]pquinazolin-5-one
Linear QZ-Aryl Example 4A: Y = methylidene
A-M = Methoxyl bridge
AGS-1101

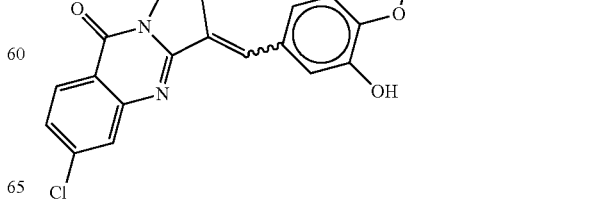

TABLE 1-continued

EXAMPLE OF ALLOSTERIC GALECTIN SHIFTING COMPOUNDS (AGS):

Linear QZ

Example 3A: Y = methylidene
AGS-1011

(3E)-3-[(2H-1,3-benzodioxol-5-yl)methylidene]-1H,2H,3H,9H-pyrrolo[2,1-b]quinazolin-9-one Example 3B: Z = Sulfate
AGS-1021

(3E)-3-[(4-bromothiophen-2-yl)methylidene]-6-(trifluoromethyl)-1H,2H,3H,9H-pyrrolo[2,1-b]quinazolin-9-one Aspects of the invention relate to compounds or compositions comprising a compound in an acceptable pharmaceutical carrier for enteral or parenteral administration, for use in therapeutic formulations. In some embodiments, the composition can be administered enteral via oral formulations, or parenterally via an intravenous or subcutaneous route.

Aspects of the invention relate to compounds or compositions for the treatment of various disorders in which lectin proteins play a role in the pathogenesis, including but not limited to, chronic inflammatory, fibrotic, metabolic diseases and malignant diseases. In some embodiments, the compound is capable of mimicking glycoprotein interactions with lectins or galectin proteins which are known to modulate the pathophysiological pathways leading to inflammation, fibrogenesis, angiogenesis, systemic insulin resistance, cancer progression and metastasis.

In some embodiments, the compound comprises pyrroloquinazoline-ketone structures bound via a single carbon atom, a methyl, to an aryl compound.

In some embodiments, specific aromatic substitutions can be added to the aryl core to further enhance the affinity of the aryl linked pyrroloquinazoline-ketone structures. Such aromatic substitutions can enhance the interaction of the compound with amino acid residues (e.g. Arginine, Tryptophan, Histidine, Glutamic acid etc. . . . ) exposed on the galectin in proximity to the carbohydrate-recognition-domains (CRD) of the lectins and thus prompting changes in the association and binding specificity of the CRD.

In some embodiments, the aryl compound comprises a single benzene ring or double aryl core linked through ethyl, ester, methyl-alkoxy, amide, sulfonamide, methyl-sulfone, or methyl-selenium which in-turn is linked to the pyrroloquinazoline-ketone compound.

In some embodiments, the compound is a symmetric di-pyrroloquinazoline-ketone-L-aryl compound, wherein the two pyrroloquinazoline-ketone-L-aryls are bound through the aryl compound by one or more linkages that are systemically cleaved to generate active pharmaceutical anti-Gal-3 compound.

In some embodiments, the compound is a symmetric di-Pyrroloquinazoline-ketone-L-aryl, wherein the two pyrroloquinazoline-ketones are linked through one or more systemically cleavable bonds such as disulfur, diselenium, ester, or amide bonds. The resultant two compounds generated systemically by enzymatic cleavage (mainly in the liver) post administration, are active pharmaceutical anti Gal-3.

Yet in other embodiments, the compound can be an asymmetric where the aryl substitutions are not symmetric. For example, the compound can have different aromatic or aliphatic substitutions on the aryl core.

In some embodiments, the compound is a fluoride derivatized pyrroloquinazoline-ketone-methyl-diphenol.

Aspect the present invention relates to a compound of formulas (I, II, III, IV) or a pharmaceutically acceptable salt or solvate thereof.

In some embodiments, the compound is in a free form. In some embodiments, the free form is an anhydrate. In some embodiments, the free form is a solvate, such as a hydrate.

In some embodiments, the compound of formula (I, II, III and IV) is in a crystalline form.

Without being bound to the theory, it is believed that the compounds containing the Pyrroloquinazoline-ketone containing molecules render the compound metabolically stable while maintaining the chemical, physical and allosteric characteristics for specific interaction with Gal-3 and affecting its recognition of target glycoproteins. In some embodiments, the pyrroloquinazoline-ketone aryl hybrids are metabolically more stable than galactose base inhibitors.

Furthermore, according to aspects of the invention, the compounds described herein and derivatives thereof do not interact with the CRD site on Gal-3. Unexpectedly, the compounds described herein are capable to disrupt the interaction of glycoproteins, such as various integrins, Gal-3 BP, elastin, insulin receptor, TGFb1-r=Receptor, HSP60, CD13, PSA and others from binding to the CRD site.

Furthermore, the compounds described herein target specifically the F-face of the Gal-3 which give these compounds great specificity versus other galectins that share common CRD sites. This can be seen in FIG. 1. FIG. 1 shows the 3D display of lactose (blue) interaction with the S-face of the Galectin-3 C-terminal CRD site.

Figure 2A:
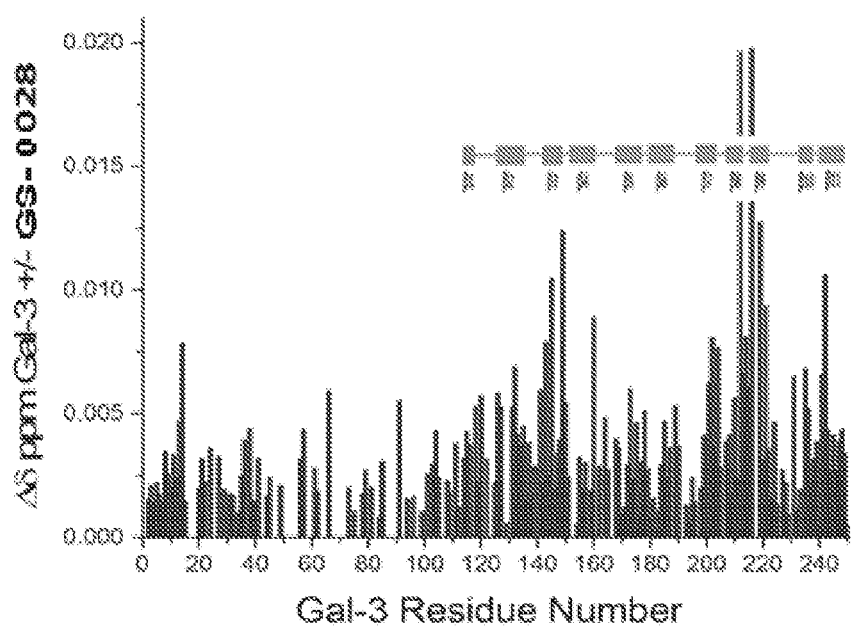
FIG. 2 shows $^{15}N$ NMR shifts, comparative analysis of allosteric compound (left, AGS-0028) and galactose based compound (right, TD-139) according to embodiments of the invention.
Figure 2B:
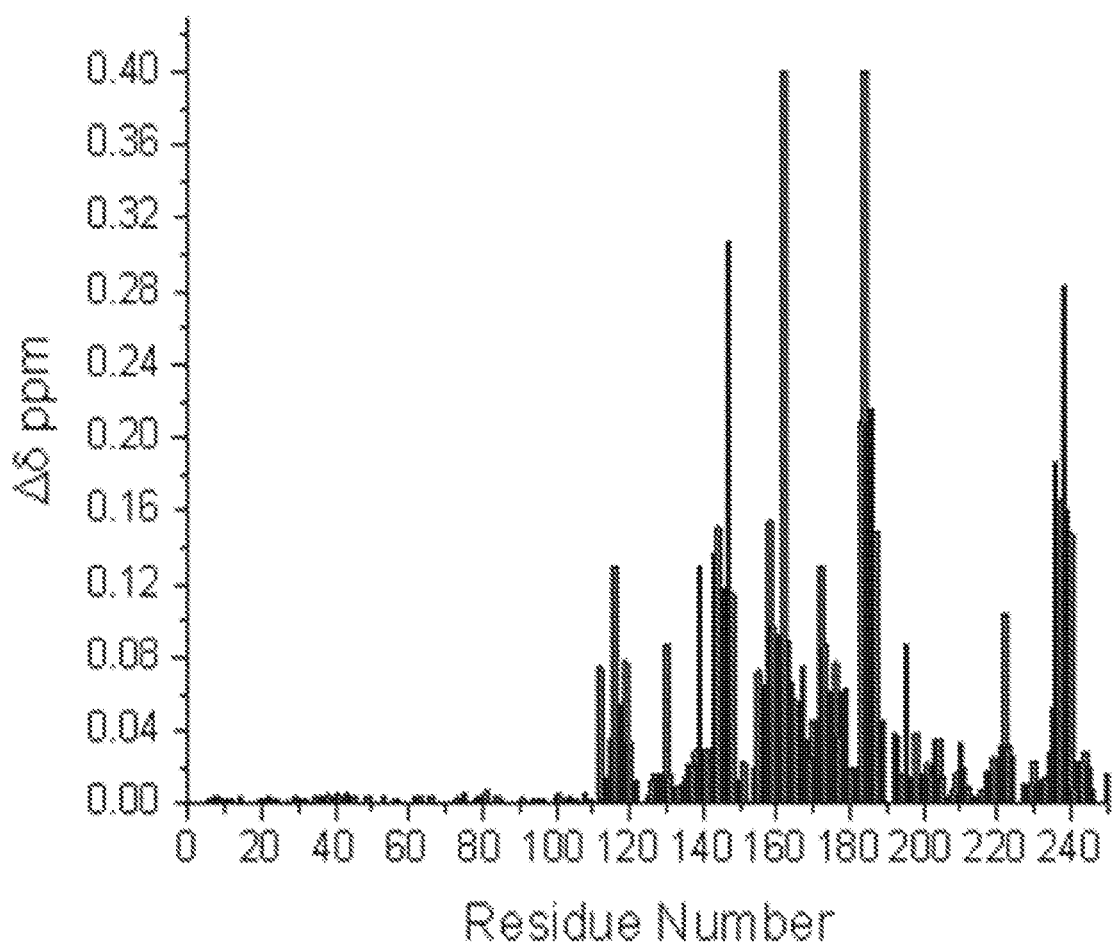

Furthermore, the compounds described herein targeting the F-face of the Gal-3 have shown clear shifts in $^{15}$N NMR studies. FIG. 2A and FIG. 2B is a comparative analysis by $^{15}$NMR shifts of an allosteric compound (left, AGS-0028) and galactose derivative compound (right, TD-139). FIGS. 2A and 2B show that the allosteric site interaction causes marginal shifts (FIG. 2A, AGS-0028, Max 0.02 ppm) at the C-terminal CRD S-face (Amino-acids 114-245) as compare to the strong shifts recorded with galactose derivative compound (FIG. 2B, TD-139, Max 0.4 ppm.

In some aspect, the compounds can be designed with chemical attributes to obey the Lipinski rule of 5 for oral drug [Lipinski, 2004, "Lead- and drug-like compounds: the rule-of-five revolution". Drug Discovery Today: Technologies 1 (4): 337-341].

In some aspects the substituents on the hybrid compounds have been selected through In-silico computational structure ADME prediction analysis for drugability characteristics.

Furthermore, stereoisomerization can be taken into consideration during synthesis as compounds with identical 2D nomenclature, could be different in the 3D orientation, which scores very different in the computer model as well in biological testing.

In some embodiments, in-silico computational analysis can be done for stability and expected metabolites, e.g. aromatic ring without certain substitutions could be metabolized or/and oxidized faster in the liver microsomes.

Furthermore, drugability likeness structure can be considered including the following: Molecular weight [<450] Log p or cLog P [<5.0], H bond donors [<5], H Bond acceptors [<10], Polar Surface area [<140 AO], Rotatable bonds [<10], Ligand Efficiency (LE) [>0.4], Lipophilic Efficiency (LipE) [>6] as established by medicinal chemistry rules [Lipinski CA. 2004, Drug Discovery Today: Technologies. 1 (4): 337-341].

Furthermore, binding to allosteric site can be studied by in-silico 3D analysis (see FIGS. 2A and 2B) that indicate potential effect in the 3D structure of the CRD and thus attenuate the binding pocket specificity which could either reduce or enhance the CRD affinity to its galactose ligands.

Figure 3A:
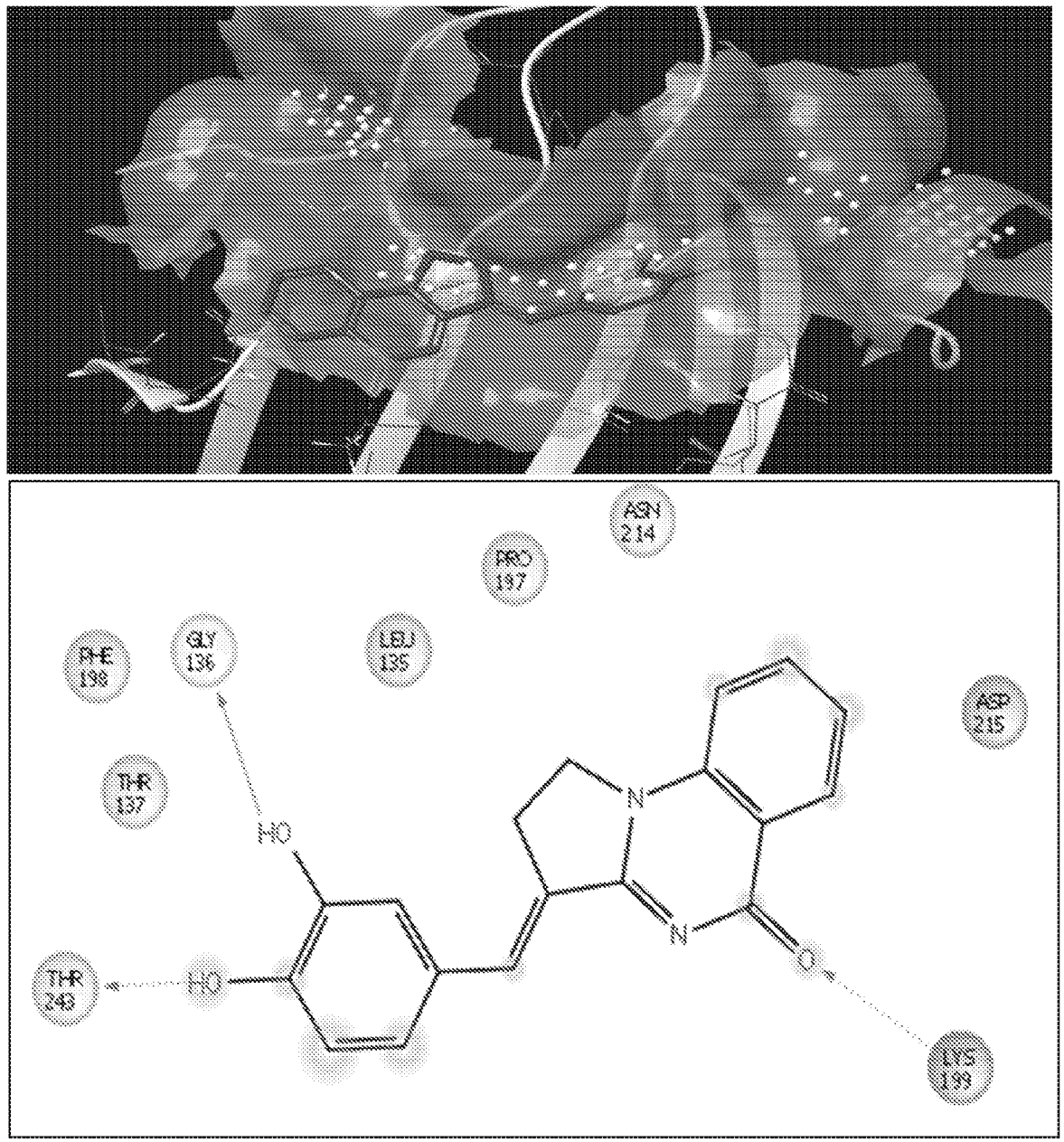
FIG. 3A illustrates a 3D picture of hydrophobic patches (yellow) within a Binding site pocket (grey) on the F-Face of Gal-3 identified as potential target for allosteric compounds (green) that could affect Gal-3 interaction with its ligands according to embodiments of the invention.

Binding of Compound AGS-0028 (green) of Formula I to a hydrophobic patches (yellow) within a binding site pocket (grey) on the F-Face is illustrated in FIG. 3A. Referring to FIG. 3A, illustration is made for hydrophobic patches (yellow) within a Binding site pocket (grey) on the F-Face of Gal-3 as potential target for allosteric compounds (green) that could affect galectin-3 interaction with its ligands.

Figure 3B:
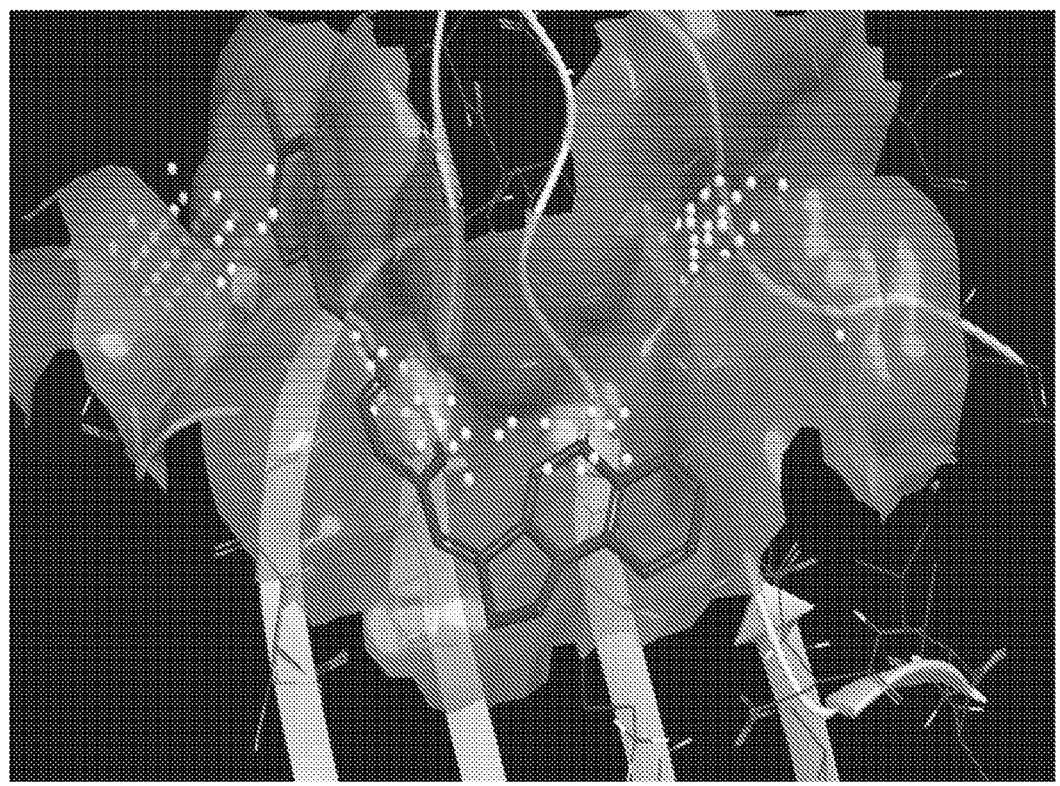
FIG. 3B illustrates a 3D picture of a compound AGS-0144 (green) interacting with the potential target for these allosteric compounds on the F-Face of Gal-3 with a Glide score of −5.96 according to embodiments of the invention.
Figure 3B:
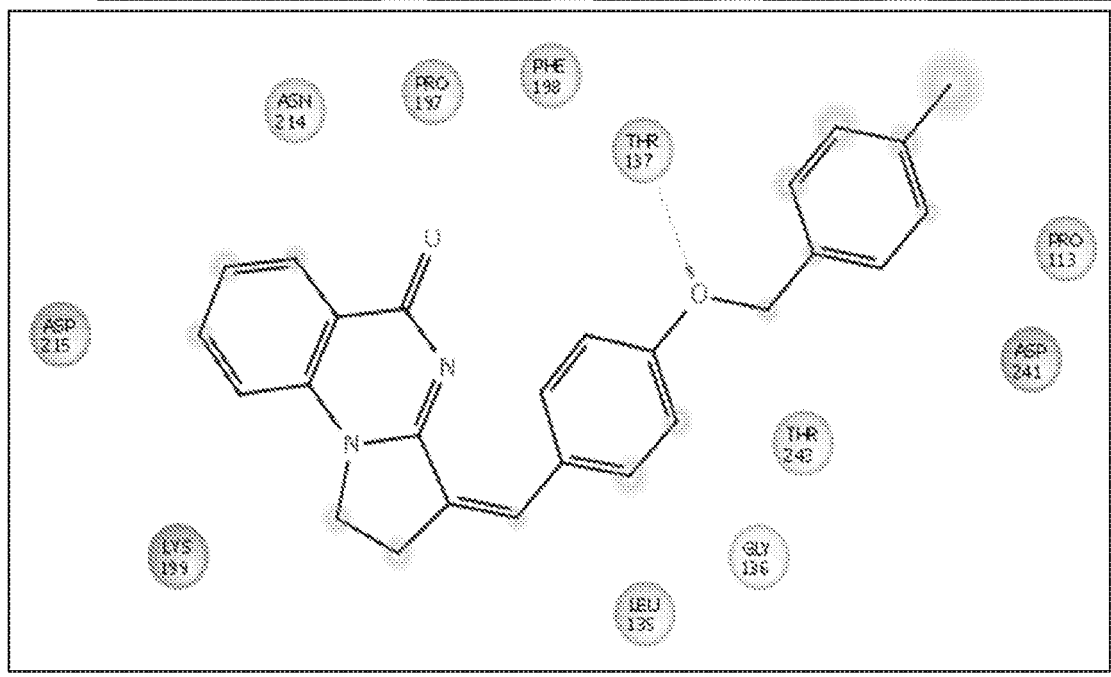

Compound AGS-0144 (green) of Formula II is shown interacting with the potential target for these allosteric compounds on the F-Face of Galectin-3 with a Glide score of −5.96 (FIG. 3B).

Figure 3C:
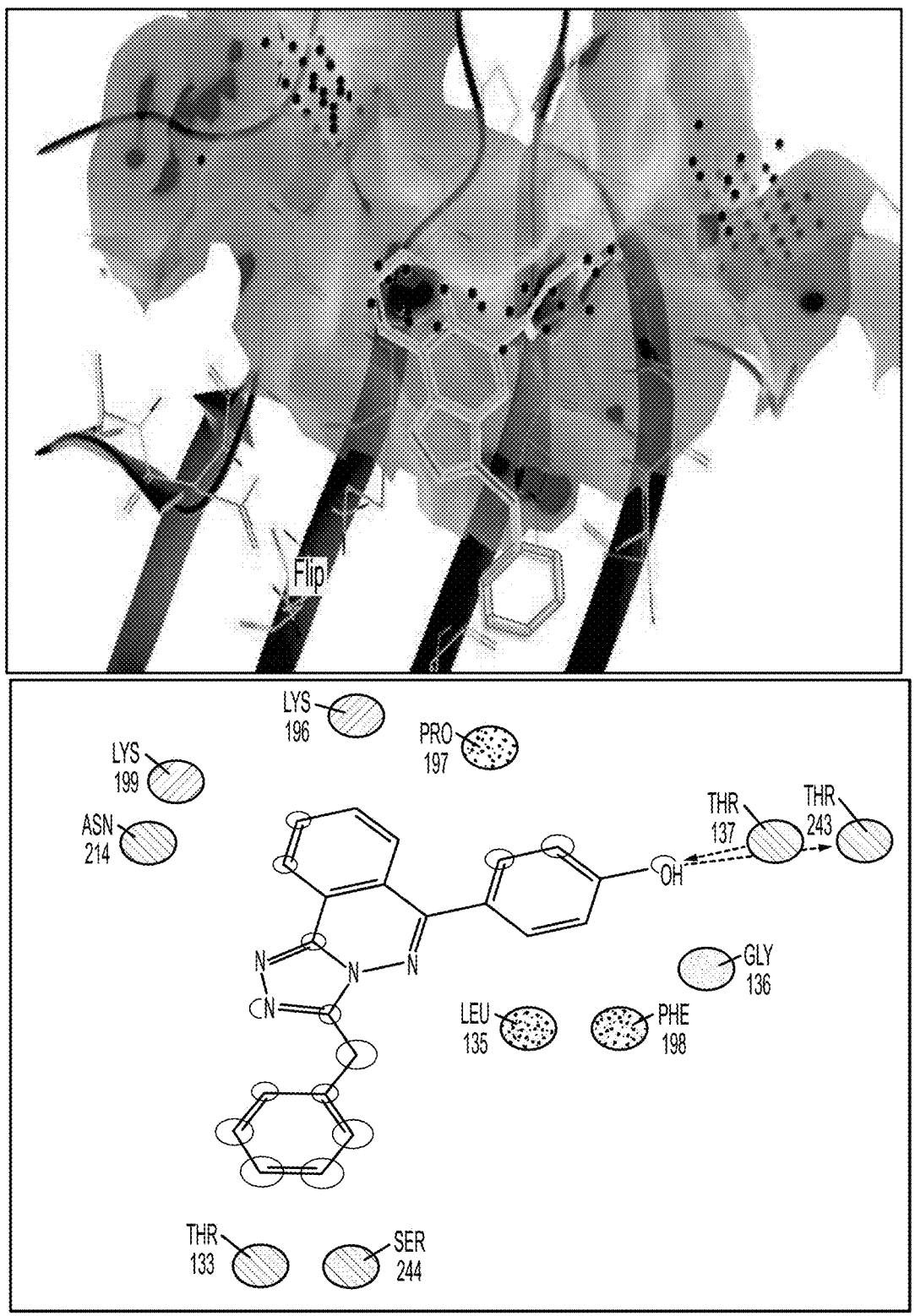
FIG. 3C illustrates a 3D picture of a compound AGS-0164 (green) interacting with the potential target for these allosteric compounds on the F-Face of Gal-3 with a Glide score of −7.09 according to embodiments of the invention.

FIG. 3C disclosed Compound AGS-0164 (green) binding with the potential target for these allosteric compounds on the F-Face of Gal-3 with a Glide score of −7.09.

Some aspects of the present invention relate to a compound of Formula I, Formula II, Formula III or Formula IV for use as a therapeutic agent in a mammal, such as a human.

Some aspects of the present invention relate to a pharmaceutical composition comprising the compound of Formula I, Formula II, Formula III or Formula IV and optionally a pharmaceutically acceptable additive, such as carrier or excipient.

In some embodiments, the compound binds with high selectivity to Gal-3 through an allosteric site and affecting the CRD.

In some embodiments, the compounds have very high selectivity and affinity for Gal-3 at the range of 5 ηM to 20 μM.

TABLE 2

Examples of compounds of Formula II.

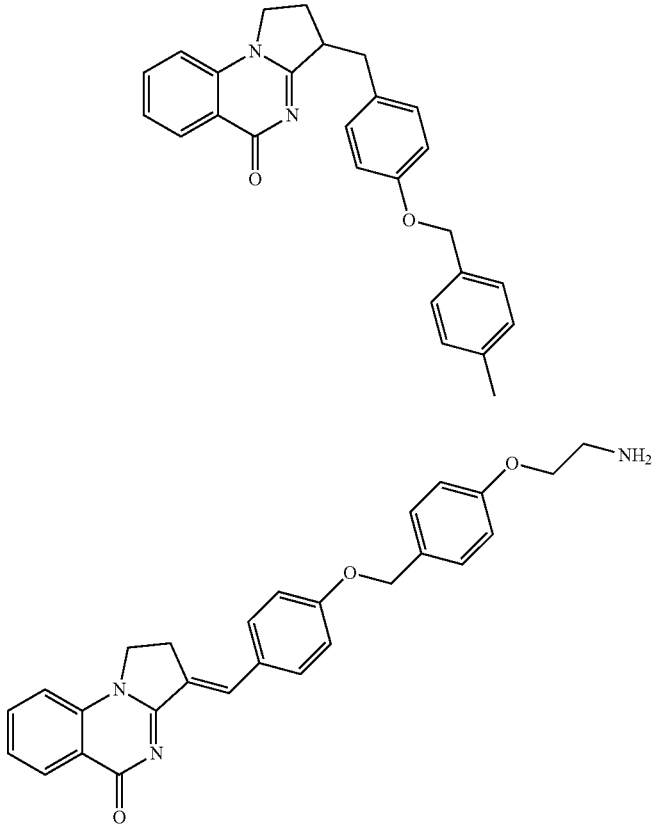

TABLE 2-continued
Examples of compounds of Formula II.
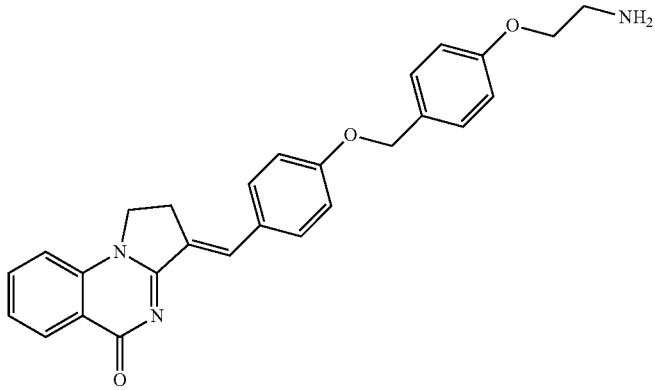 [SMILES: NCCOc1ccc(COc2ccc(/C=C3\CCn4c3nc(=O)c3ccccc34)cc2)cc1]
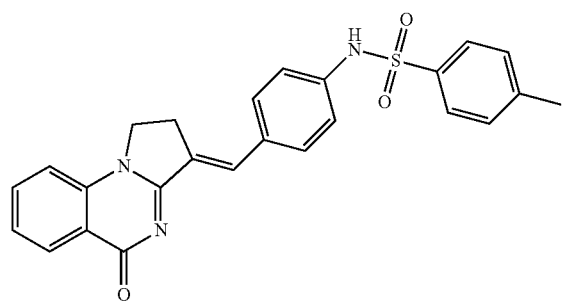 [SMILES: Cc1ccc(S(=O)(=O)Nc2ccc(/C=C3\CCn4c3nc(=O)c3ccccc34)cc2)cc1]
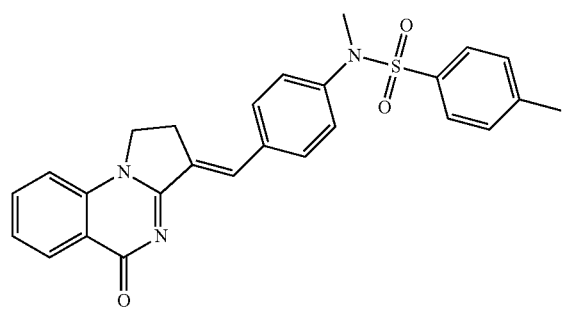 [SMILES: Cc1ccc(S(=O)(=O)N(C)c2ccc(/C=C3\CCn4c3nc(=O)c3ccccc34)cc2)cc1]
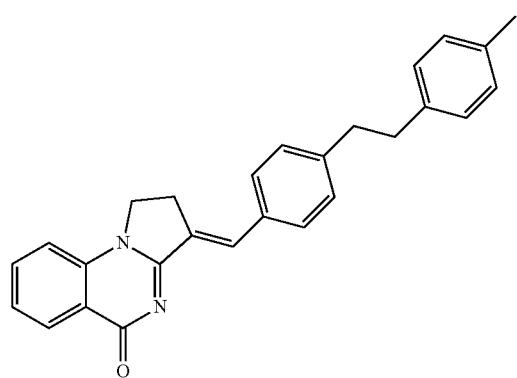

TABLE 2-continued
Examples of compounds of Formula II.
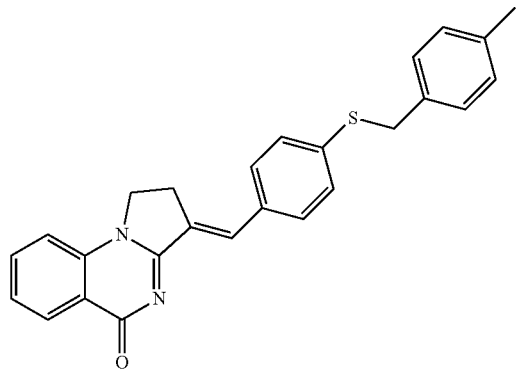 [SMILES: Cc1ccc(CSc2ccc(/C=C3\CCn4c3nc(=O)c3ccccc34)cc2)cc1]
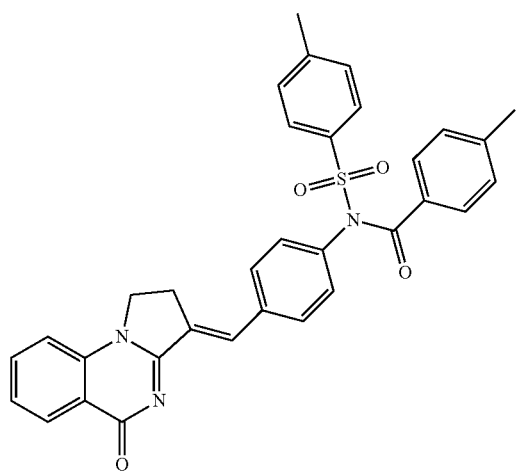 [SMILES: Cc1ccc(C(=O)N(c2ccc(/C=C3\CCn4c3nc(=O)c3ccccc34)cc2)S(=O)(=O)c2ccc(C)cc2)cc1]
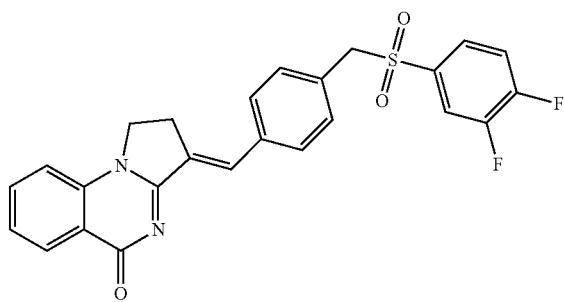 [SMILES: O=c1nc2n(c3ccccc13)CC/C2=C\c1ccc(CS(=O)(=O)c2ccc(F)c(F)c2)cc1]
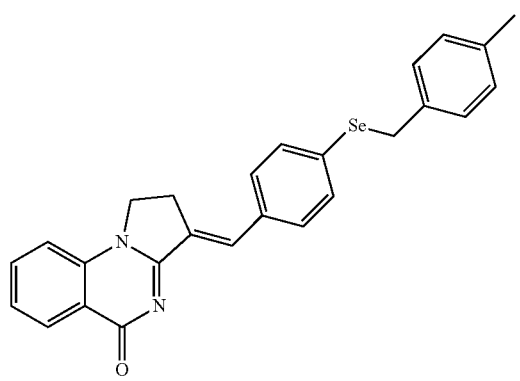

TABLE 2-continued
Examples of compounds of Formula II.
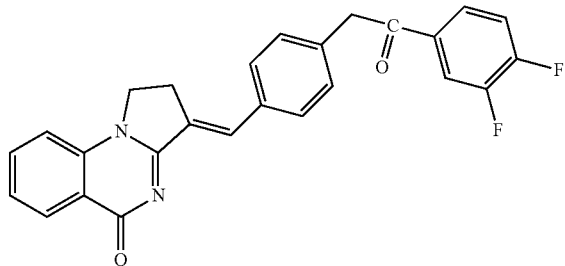 [SMILES: O=C(Cc1ccc(/C=C2\CCn3c2nc(=O)c2ccccc23)cc1)c1ccc(F)c(F)c1]
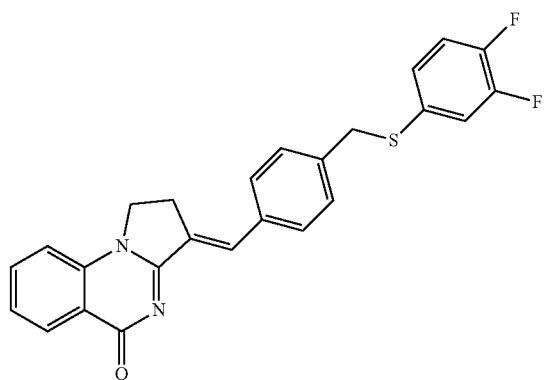 [SMILES: O=c1nc2n(c3ccccc13)CC/C2=C\c1ccc(CSc2ccc(F)c(F)c2)cc1]
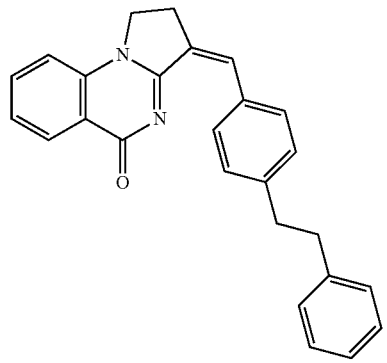 [SMILES: O=c1nc2n(c3ccccc13)CC/C2=C/c1ccc(CCc2ccccc2)cc1]
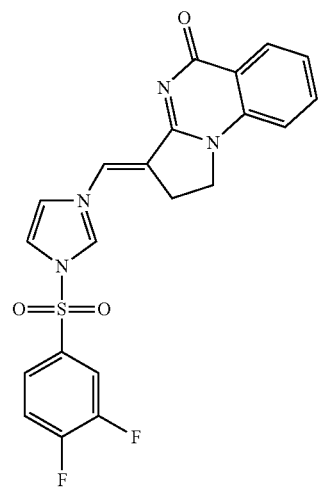

TABLE 2-continued
Examples of compounds of Formula II.
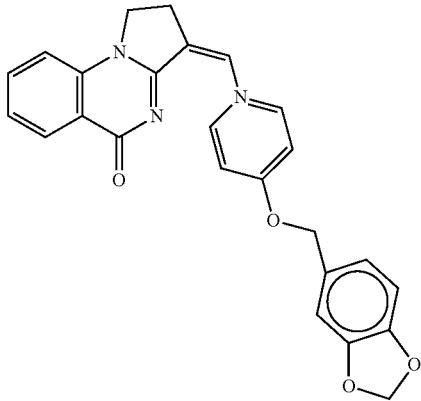
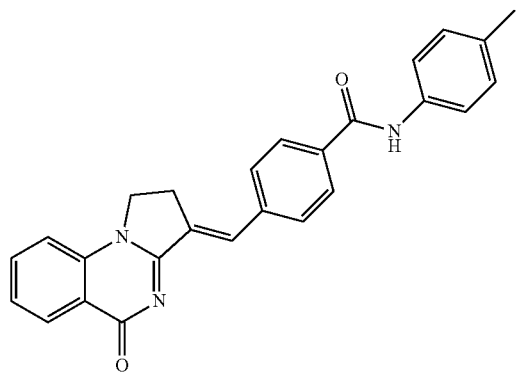 [SMILES: Cc1ccc(NC(=O)c2ccc(/C=C3\CCn4c3nc(=O)c3ccccc34)cc2)cc1]
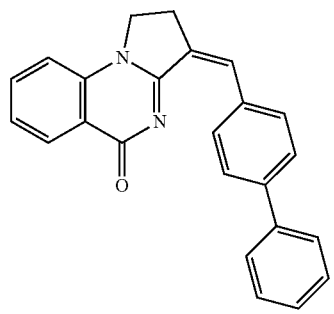 [SMILES: O=c1nc2n(c3ccccc13)CC/C2=C/c1ccc(-c2ccccc2)cc1]
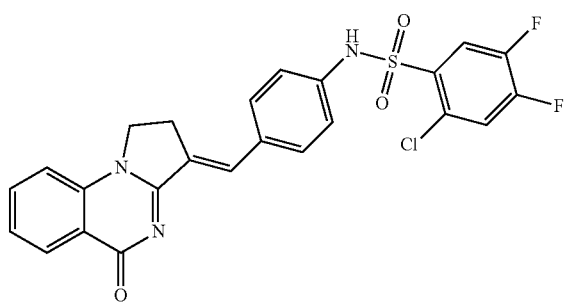 [SMILES: O=c1nc2n(c3ccccc13)CC/C2=C\c1ccc(NS(=O)(=O)c2cc(F)c(F)cc2Cl)cc1]

TABLE 3
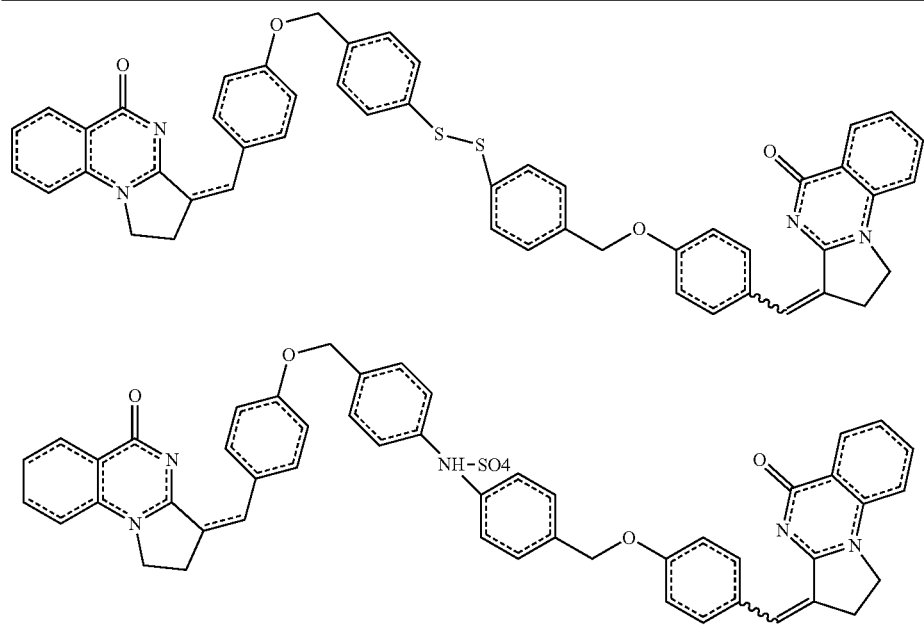
| TABLE 4 | TABLE 4-continued |
|---|---|
| Compounds of Formula I that may also be further derivatized to Formula II. | Compounds of Formula I that may also be further derivatized to Formula II. |
| 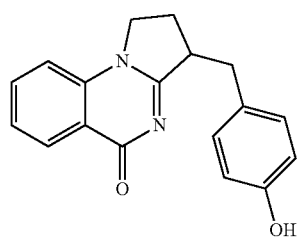 [SMILES: O=c1nc2n(c3ccccc13)CCC2Cc1ccc(O)cc1] | 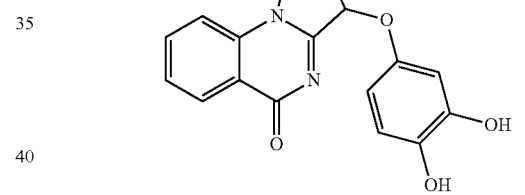 |
| 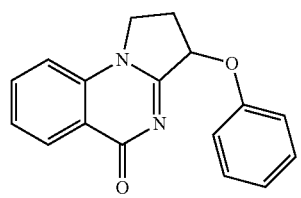 [SMILES: O=c1nc2n(c3ccccc13)CCC2Oc1ccccc1] | 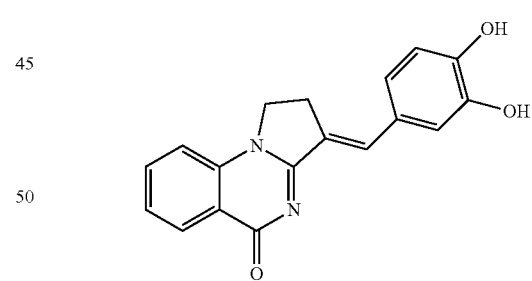 |
| 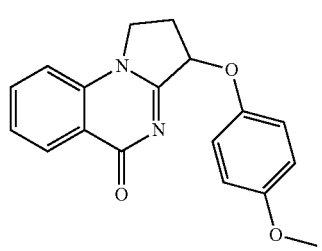 [SMILES: COc1ccc(OC2CCn3c2nc(=O)c2ccccc23)cc1] | 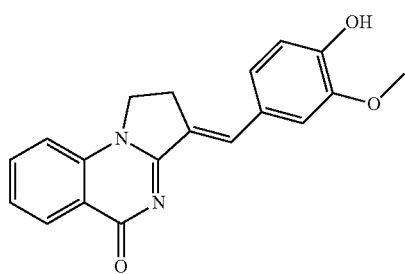 [SMILES: COc1cc(/C=C2\CCn3c2nc(=O)c2ccccc23)ccc1O] |

TABLE 4-continued
Compounds of Formula I that may also be further derivatized to Formula II.
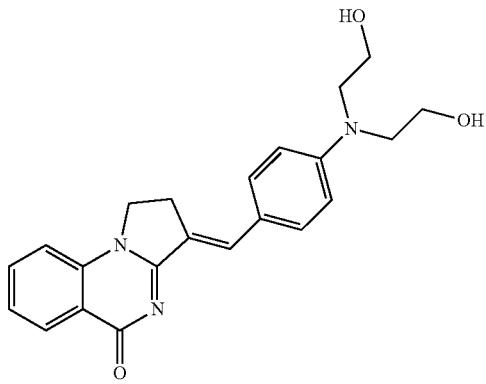 [SMILES: O=c1nc2n(c3ccccc13)CC/C2=C\c1ccc(N(CCO)CCO)cc1]
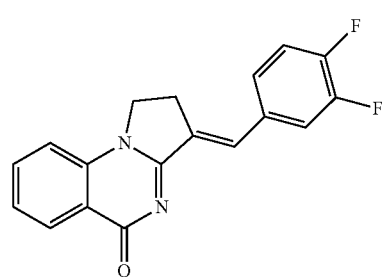 [SMILES: O=c1nc2n(c3ccccc13)CC/C2=C\c1ccc(F)c(F)c1]
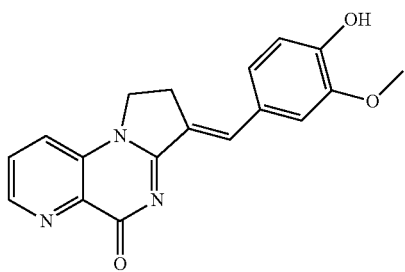 [SMILES: COc1cc(/C=C2\CCn3c2nc(=O)c2ncccc23)ccc1O]
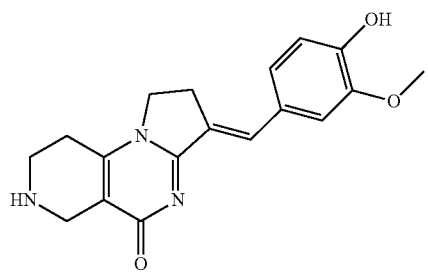 [SMILES: COc1cc(/C=C2\CCn3c2nc(=O)c2c3CCNC2)ccc1O]
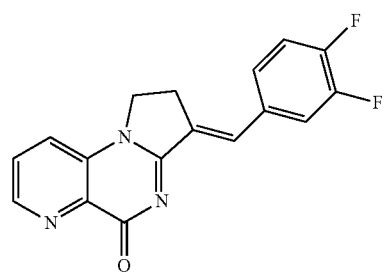 [SMILES: O=c1nc2n(c3cccnc13)CC/C2=C\c1ccc(F)c(F)c1]
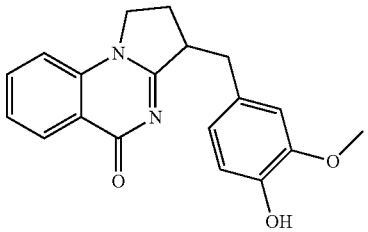 [SMILES: COc1cc(CC2CCn3c2nc(=O)c2ccccc23)ccc1O]
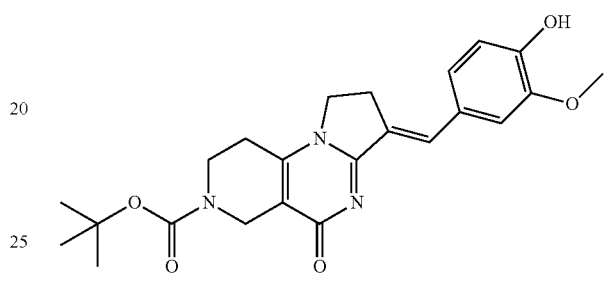
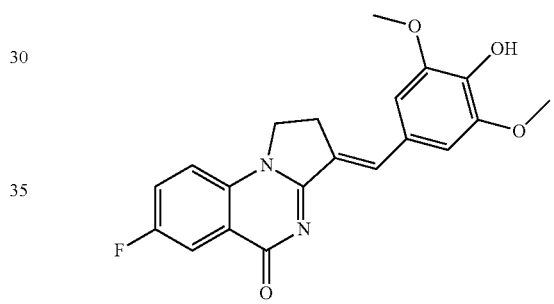
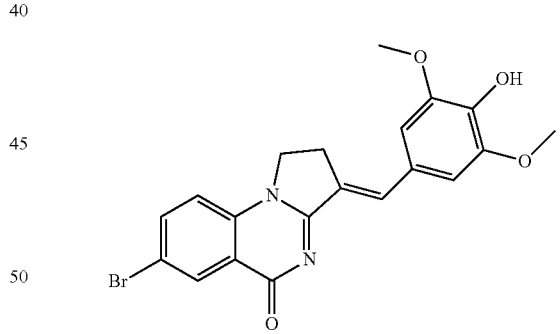
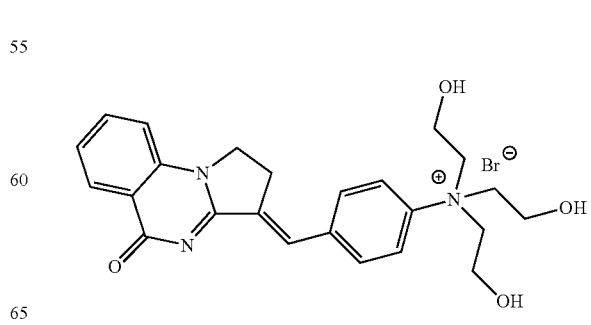

TABLE 4-continued
Compounds of Formula I that may also be further derivatized to Formula II.
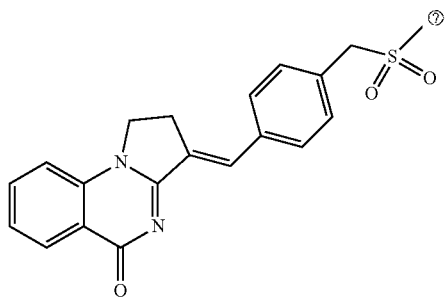
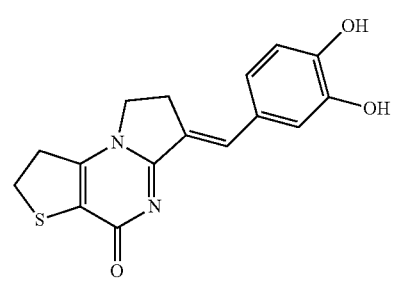 [SMILES: O=c1nc2n(c3c1SCC3)CC/C2=C\c1ccc(O)c(O)c1]
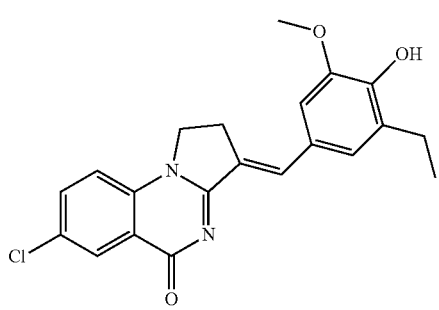 [SMILES: CCc1cc(/C=C2\CCn3c2nc(=O)c2cc(Cl)ccc23)cc(OC)c1O]
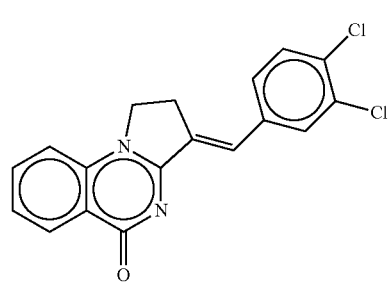
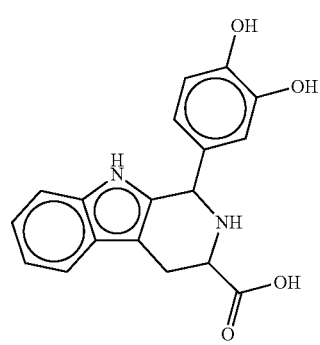
TABLE 4-continued
Compounds of Formula I that may also be further derivatized to Formula II.
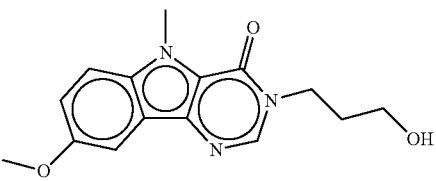
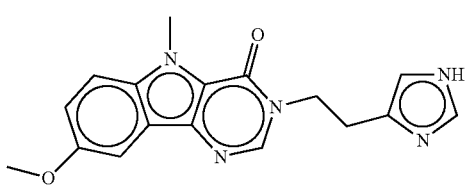
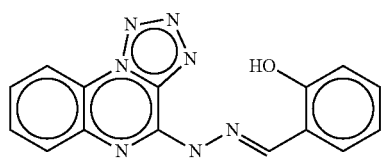
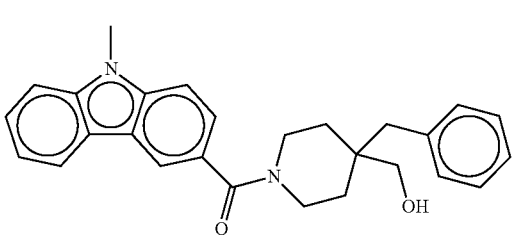
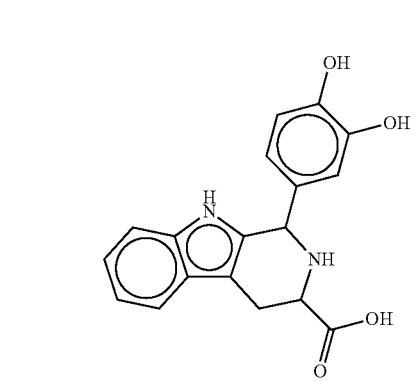
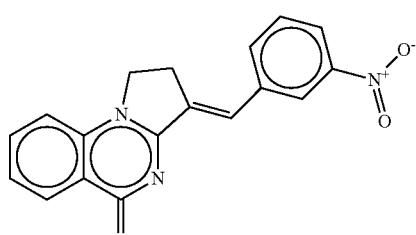

TABLE 4-continued
Compounds of Formula I that may also be further derivatized to Formula II.
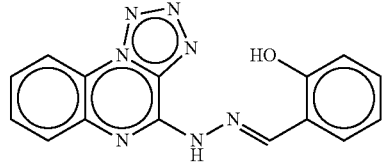
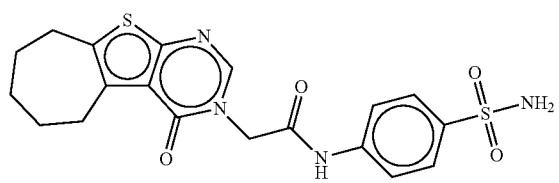
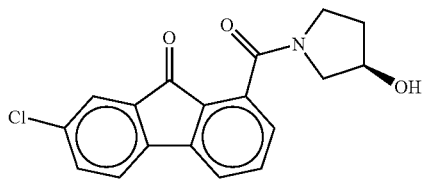
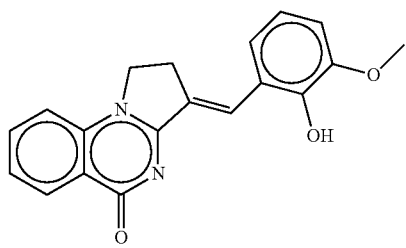
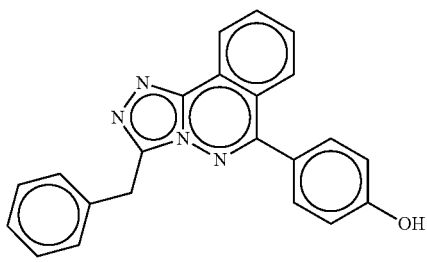
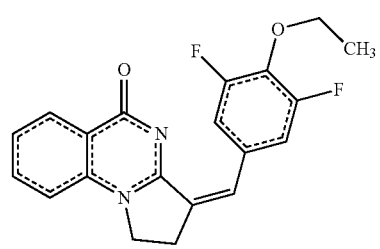
TABLE 4-continued
Compounds of Formula I that may also be further derivatized to Formula II.
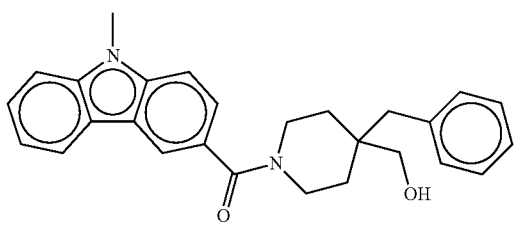
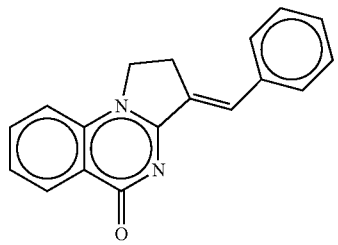
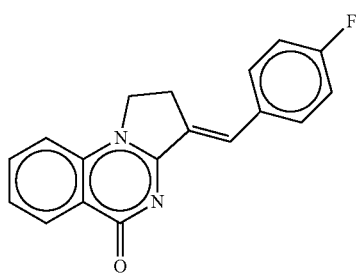
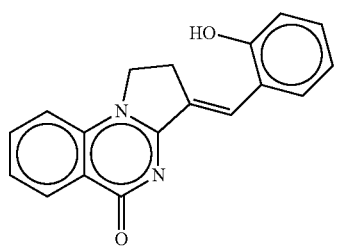
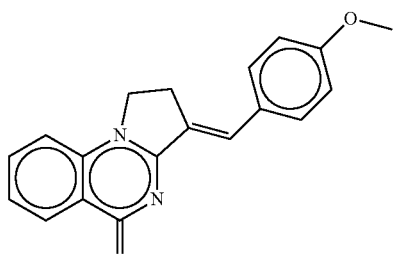
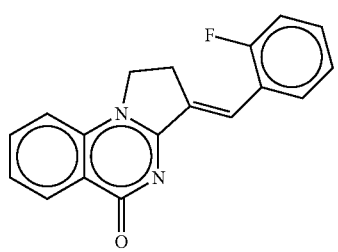

TABLE 4-continued
Compounds of Formula I that may also be further derivatized to Formula II.
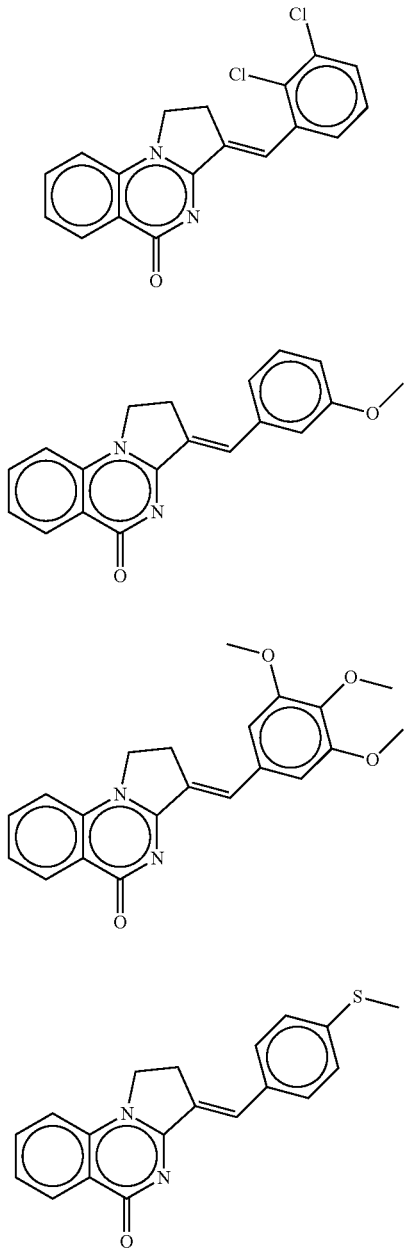
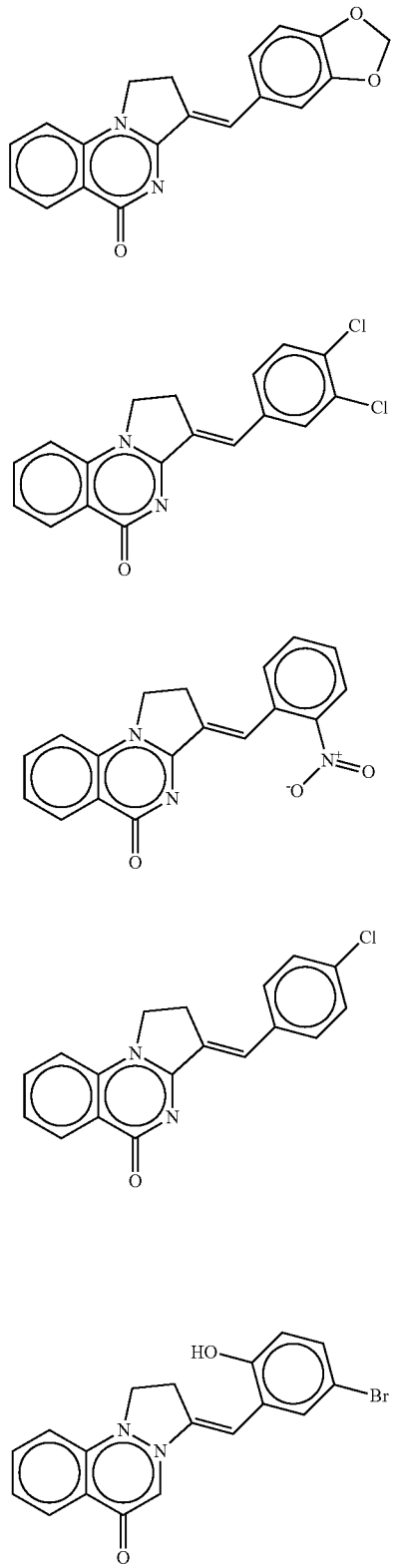

TABLE 4-continued
Compounds of Formula I that may also be further derivatized to Formula II.
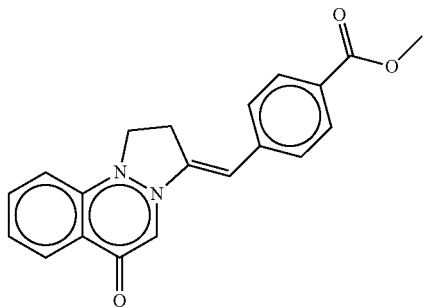
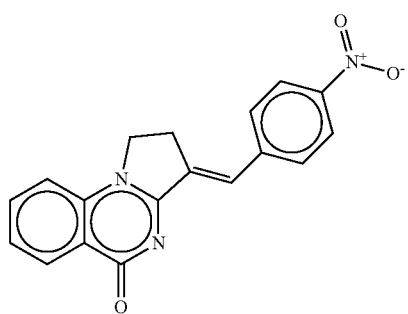
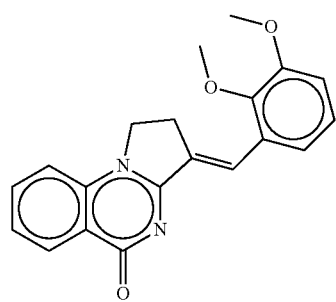
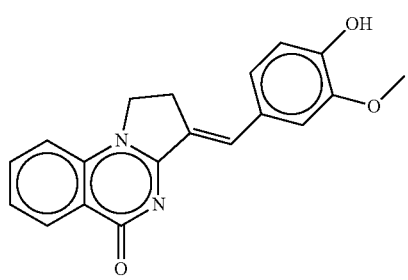
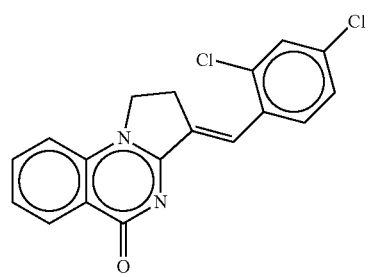
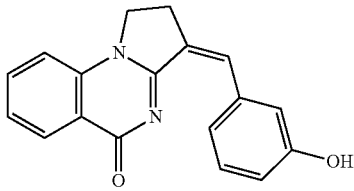
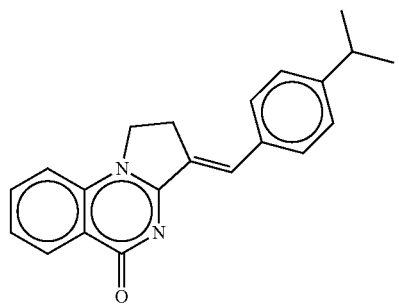
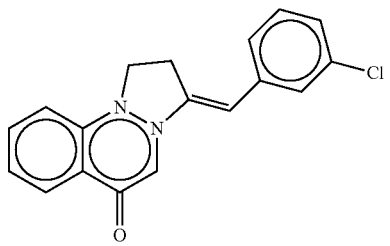
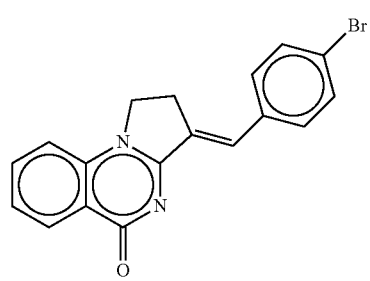
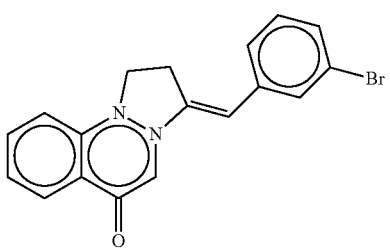

TABLE 4-continued
Compounds of Formula I that may also be further derivatized to Formula II.
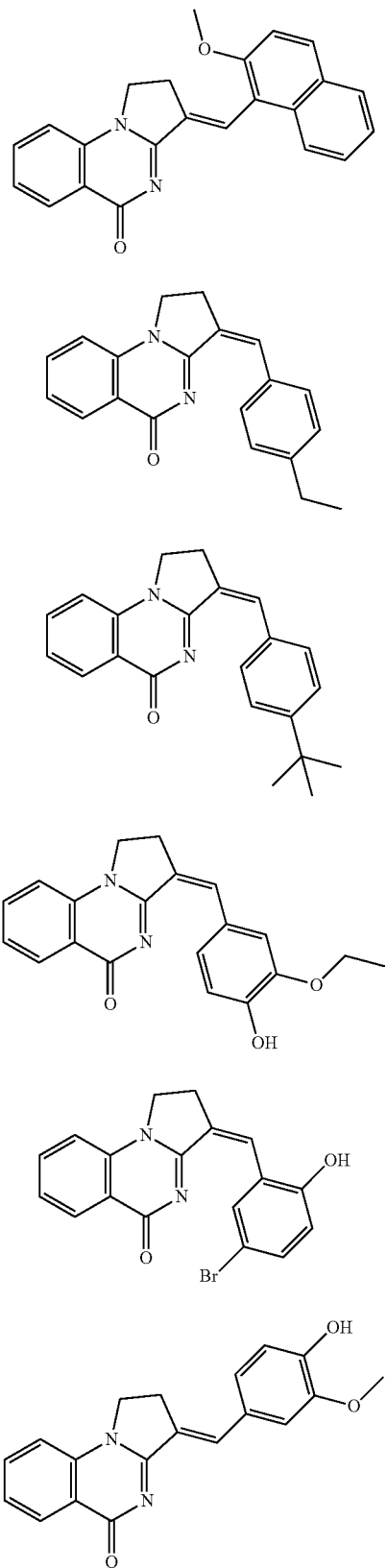
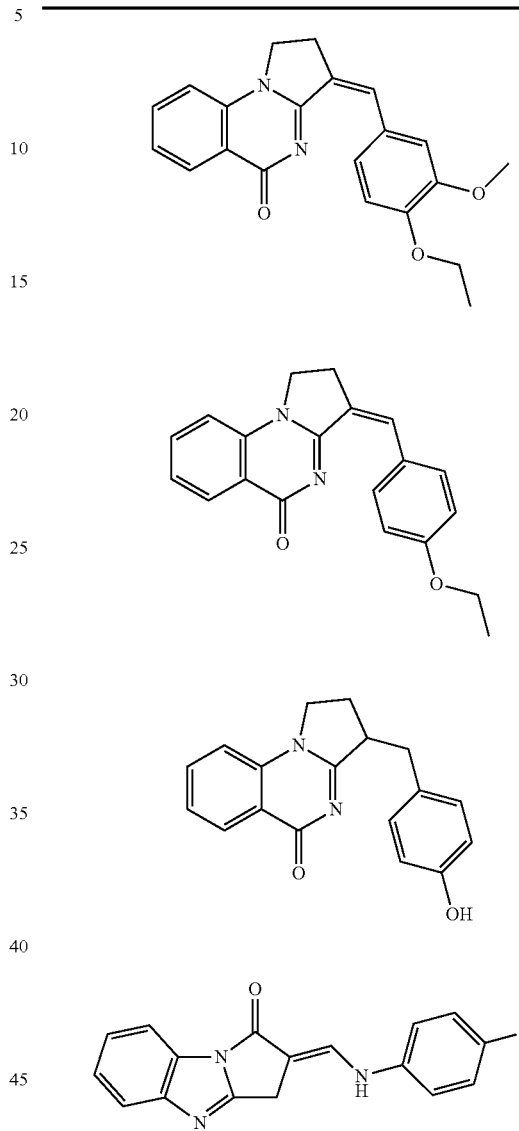
TABLE 5
Compounds of Formula III that may also be further derivatized to Formula IV. This include compounds that may found in commercial library but have not claimed for pharmaceutical activity
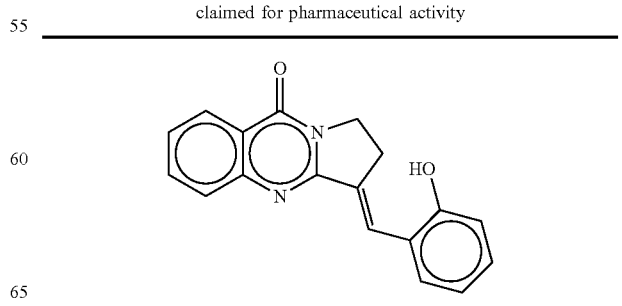

TABLE 5-continued

Compounds of Formula III that may also be further derivatized to Formula IV. This include compounds that may found in commercial library but have not claimed for pharmaceutical activity

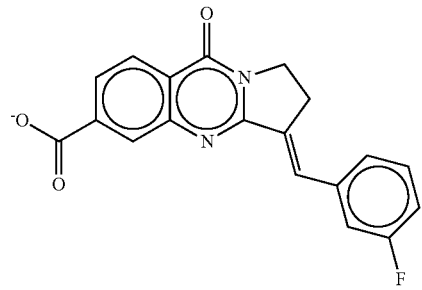

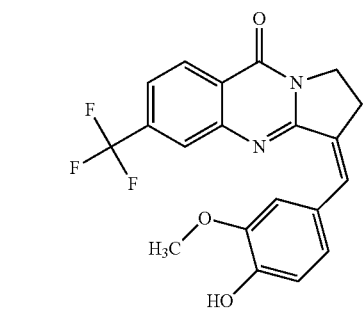 [SMILES: COc1cc(/C=C2/CCn3c2nc2cc(C(F)(F)F)ccc2c3=O)ccc1O]

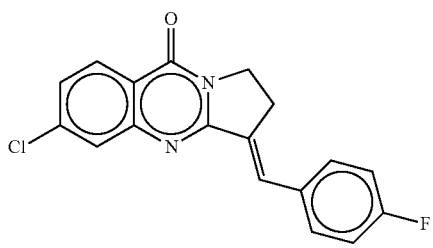

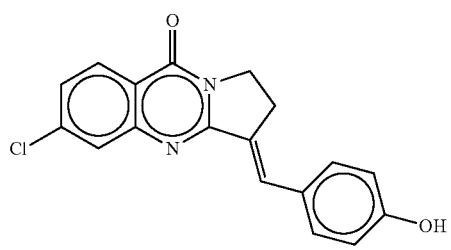

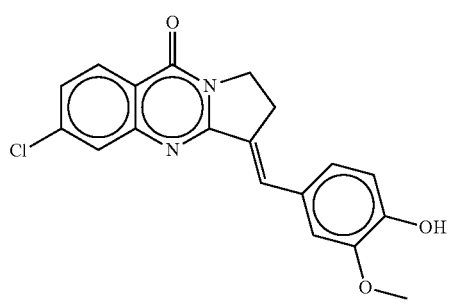

TABLE 5-continued

Compounds of Formula III that may also be further derivatized to Formula IV. This include compounds that may found in commercial library but have not claimed for pharmaceutical activity

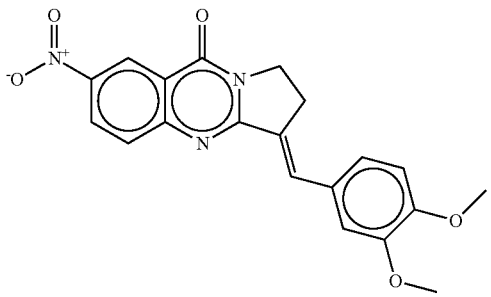

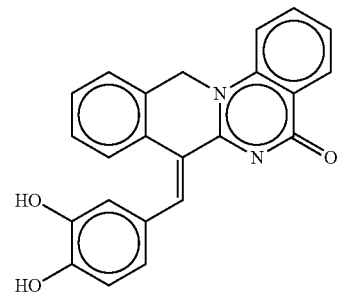

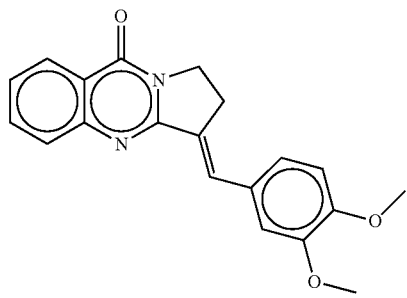

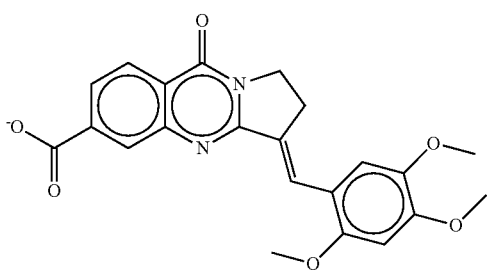

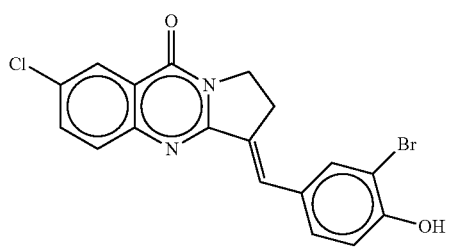

TABLE 5-continued

Compounds of Formula III that may also be further derivatized to Formula IV. This include compounds that may found in commercial library but have not claimed for pharmaceutical activity

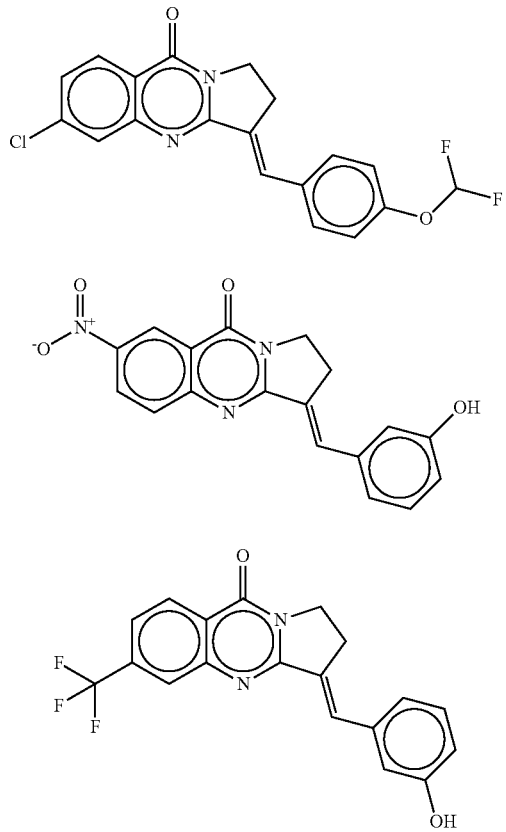

Methods of Treatment

In some embodiments, the compounds or the pharmaceutical compositions can be used in the treatment of Cancer, inflammation, Fibrosis/cirrhosis, autoimmune diseases/metabolic diseases (diabetes/insulin).

In some embodiments, the compounds or the pharmaceutical compositions can be used in the treatment of Cancer, inflammation, Fibrosis/cirrhosis, autoimmune diseases/metabolic diseases (diabetes/insulin).

In some embodiments, the compounds or the pharmaceutical compositions can be used in alcoholic or viral steatohepatitis a nonalcoholic steatohepatitis.

In some embodiments, the compounds or the pharmaceutical compositions can be used in the treatment of chronic inflammatory and autoimmune disorders In some embodiments, the compounds or the pharmaceutical compositions can be used in the treatment of fibrosis including but not limited to liver fibrosis, kidney fibrosis, lung fibrosis, or heart fibrosis.

Some aspects of the invention relate to a pharmaceutical composition or a compound capable of enhancing autonomous anti-fibrosis activity in organs and healing of injured organ but not limited to liver, kidney, lung, and heart.

Some aspects of the invention relate to a method of treating metastatic cancer and angiogenesis disorders in which Gal-3 is at least in part involved in the pathogenesis, by enhancing metastasis in organs, including but not limited to liver, kidney, lung, and brain.

Some aspects of the invention relate to a pharmaceutical composition or a compound that has a therapeutic activity to treat immunosuppression and systemic insulin resistance, in another aspect, the invention relates to a method to reduce the pathology and disease activity associated with systemic insulin resistance [Pingping Li et al. 2016. "Hematopoietic-Derived Galectin-3 Causes Cellular and Systemic Insulin Resistance", Cell. 2016 Nov. 3; 167(4):973-984].

Some aspects of the invention relate to a pharmaceutical composition or a compound utilized in treating or a method of treating inflammatory and autoimmune disorders in which galectins are at least in part involved in the pathogenesis including but not limited to arthritis, rheumatoid arthritis, asthma, skin disease, inflammatory bowel and Crohn's diseases.

Some aspects of the invention relate to a pharmaceutical composition or a compound to treat neoplastic malignant conditions (e.g. benign or malignant neoplastic diseases) in which Gal-3 is at least in part involved in the pathogenesis by inhibiting processes promoted by the increase expression of Gal-3. In some embodiments, the pharmaceutical composition or a compound can be used to treat or prevent tumor cell invasion, metastasis, and neovascularization. In some embodiments, the pharmaceutical composition or a compound can be used to treat primary and secondary cancers.

In some embodiments, a therapeutically effective amount of the compound or of the composition can be compatible and effective in combination with a therapeutically effective amount of various anti-inflammatory drugs, vitamins, other pharmaceuticals and nutraceuticals drugs or supplement, or combinations thereof without limitation.

Some aspects of the present invention relate to a compound of Formula I, Formula II, Formula III or Formula IV for use in a method for treating a disorder relating to the specific glycoprotein ligands that are activated by binding to Gal-3. Some aspects of the present invention relate to a compound of Formula I, Formula II, Formula III or Formula IV for use in a method for treating a disorder relating to the binding of Gal-3 to a specific ligand.

Some aspects of the present invention relate to a method for treatment of a disorder relating to the binding of a galectin, such as Gal-3, to a ligand in a human or other mammal, wherein the method comprises administering a therapeutically effective amount of at least one compound of Formula I, Formula II, Formula III or Formula IV to a human or a mammal in need thereof.

Aspects of the invention relate to pharmaceutical compositions comprising one or more of the compounds described herein. In some embodiments, the pharmaceutical compositions comprise one or more of the following: pharmaceutically acceptable adjuvant, diluent, excipient, and carrier.

The term "pharmaceutically acceptable carrier" refers to a carrier or adjuvant that may be administered to a subject (e.g., a patient), together with a compound described herein, and which does not destroy the pharmacological activity thereof and is nontoxic when administered in doses sufficient to deliver a therapeutic amount or an effective mount of the compound.

"Pharmaceutically acceptable carrier" refers to any and all solvents, dispersion media. The use of such media and compounds for pharmaceutically active substances is well known in the art. Preferably, the carrier is suitable for oral, intravenous, intramuscular, subcutaneous, parenteral, spinal or epidural administration (e.g., by injection or infusion). Depending on the route of administration, the active compound can be coated in a material to protect the compound from the action of acids and other natural conditions that can inactivate the compound.

In some embodiments, the pharmaceutical composition comprises a compound described herein as active ingredient together with a pharmaceutically acceptable adjuvant, diluent, excipient or carrier. A pharmaceutical composition can comprise from 1 to 99 weight % of a pharmaceutically acceptable adjuvant, diluent, excipient or carrier and from 1 to 99 weight % of a compound described herein.

The adjuvants, diluents, excipients and/or carriers that may be used in the composition of the invention are pharmaceutically acceptable, i.e. are compatible with the compounds and the other ingredients of the pharmaceutical composition, and not deleterious to the recipient thereof. The adjuvants, diluents, excipients and carriers that may be used in the pharmaceutical composition of the invention are well known to a person within the art.

An effective oral dose of the compound of the present invention to an experimental animal or human may be formulated with a variety of excipients and additives that enhance the absorption of the compound via the stomach and small intestine.

The pharmaceutical composition of the present invention may comprise two or more compounds of the present invention. The composition may also be used together with other medicaments within the art for the treatment of related disorders.

In some embodiments, the pharmaceutical composition comprising one or more compounds described herein may be adapted for oral, intravenous, topical, intraperitoneal, nasal, buccal, sublingual, or subcutaneous administration, or for administration via the respiratory tract in the form of, for example, an aerosol or an air-suspended fine powder, or, for administration via the eye, intra-ocularly, intravitreally or corneally.

In some embodiments, the pharmaceutical composition comprising one or more compounds described herein may be in the form of, for example, tablets, capsules, powders, solutions for injection, solutions for spraying, ointments, transdermal patches or suppositories.

Some aspects of the present invention relate to pharmaceutical composition comprising the compound described herein or a pharmaceutically acceptable salt or solvate thereof and optionally a pharmaceutically acceptable additive, such as carrier or excipient.

An effective oral dose could be 10 times and up to 100 times the amount of the effective parental dose.

An effective oral dose may be given daily, in one or divided doses or twice, three times weekly, or monthly.

In some embodiments, the compounds described herein can be co-administered with one or more other therapeutic agents. In certain embodiments, the additional agents may be administered separately, as part of a multiple dose regimen, from the compounds described herein (e.g., sequentially, e.g., on different overlapping schedules with the administration of the compound described herein). In other embodiments, these agents may be part of a single dosage form, mixed together with the compounds described herein in a single composition. In still another embodiment, these agents can be given as a separate dose that is administered at about the same time that the compounds described herein. When the compositions include a combination of the compound described herein and one or more additional therapeutic or prophylactic agents, both the compound and the additional agent can be present at dosage levels of between about 1 to 10000, and more preferably between about 5 to 95% o of the dosage normally administered in a monotherapy regimen.

Methods of Making

Aspects of the invention relate to the method of making compounds described herein.

TABLE 6

Examples Of Synthesis Of Compounds According To Aspects of the Invention:

| GS Codes | Manufacturing codes | Structures |
|---|---|---|
| AGS-0928 | GTJC-144-009 | 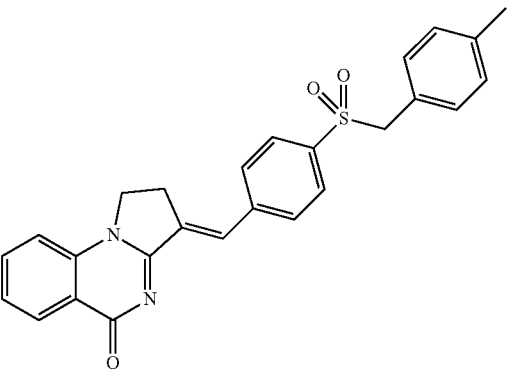 |

GTJC-144-009

TABLE 6-continued
Examples Of Synthesis Of Compounds According To Aspects of the Invention:
| GS Codes | Manufacturing codes | Structures |
|---|---|---|
| AGS-0925 | GTJC-144-006 | 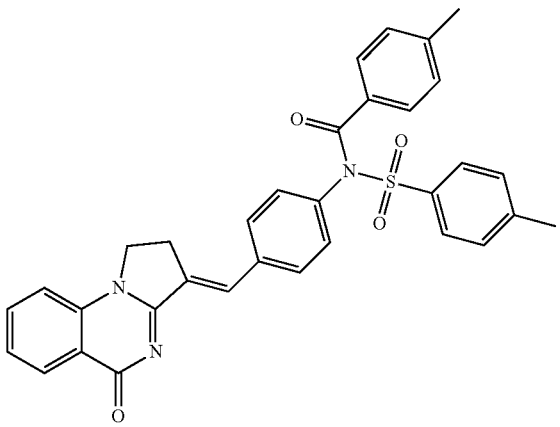<br>GTJC-144-006 |
| AGS-0907 | GTJC-144-008 | 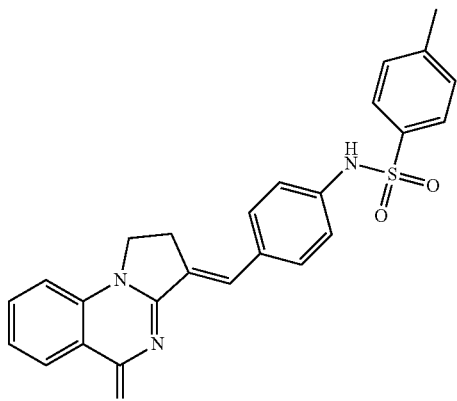<br>GTJC-144-008 |
| AGS-0921 | GTJC-144-008-1 | 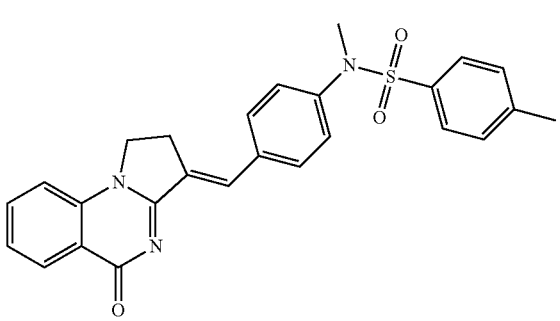<br>GTJC-144-008-1 |

TABLE 6-continued
Examples Of Synthesis Of Compounds According To Aspects of the Invention:
| GS Codes | Manufacturing codes | Structures |
|---|---|---|
| AGS-0926 | GTJC-028-12-2 | 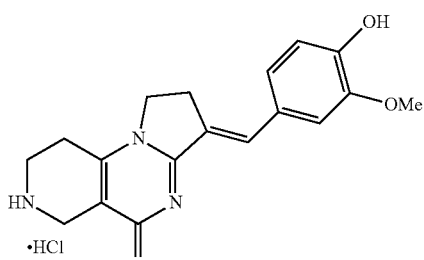<br>GTJC-028-12-2 |
| AGS-0923 | GTJC-028-021 | 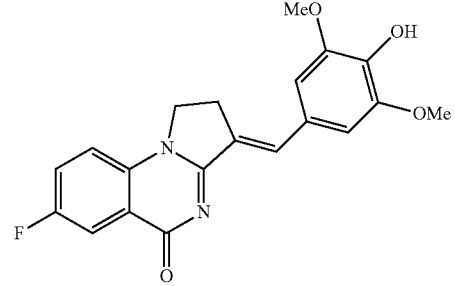<br>GTJC-028-021 |
| AGS-0924 | GTJC-028-022 | 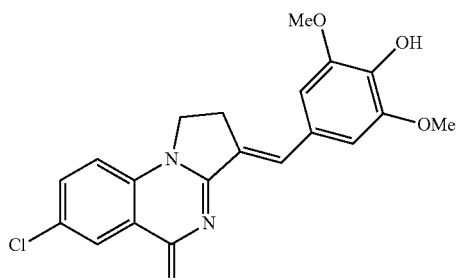<br>GTJC-028-022 |
| AGS-0934 | GTJC-028-023 | 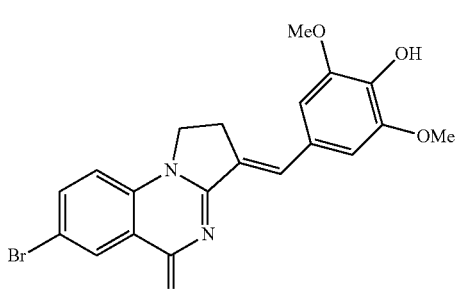<br>GTJC-028-023 |

Experimental Procedure for AGS-0928 (GTJC-144-009)

Scheme I

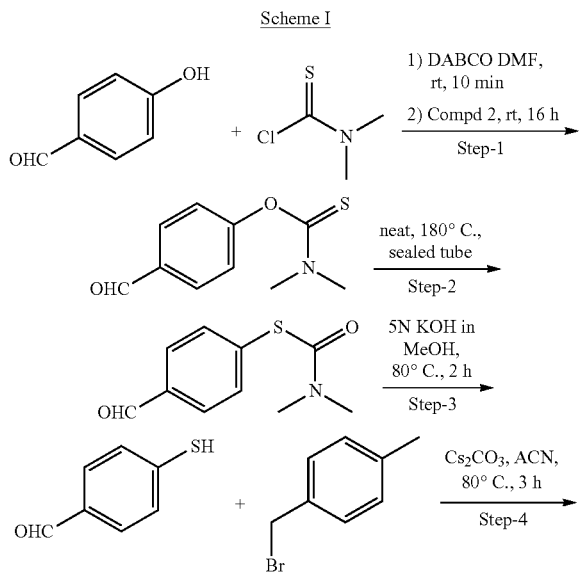

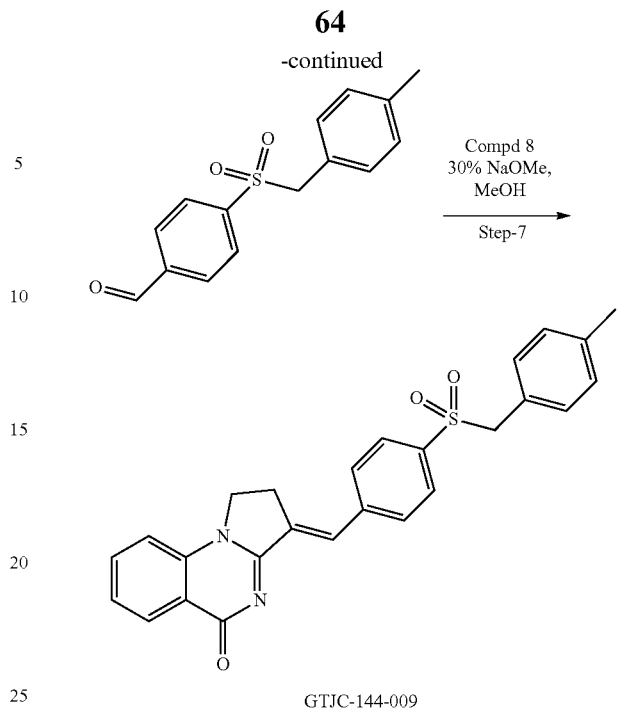

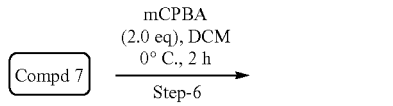

Step-1:
O-(4-formylphenyl) dimethylcarbamothioate: DABCO (3.60 g, 32.78 mmol) was added to a solution of 4-hydroxybenzaldehyde 1 (2.0 g, 16.39 mmol) in DMF (20 mL) at room temperature and the reaction mixture was stirred for 10 min Dimethylcarbamothioic chloride (4.03 g, 32. mmol) was then added portionwise and the reaction mixture was stirred for 16 h. Ice cold water (100 mL) was added to the reaction mixture and stored in refrigerator for 5 h. The precipitated solid was filtered through sintered funnel and purified by Combiflash using 100% ethyl acetate in hexane to afford O-(4-formylphenyl) dimethylcarbamothioate 3 as a white solid (1.80 g, 500%). HRMS (ESI) [M+H]+ calc. for $C_{10}H_{11}NO_2S$ is 209.05, found: 210.00 [M+H]+

$^1$H NMR (400 MHz; CDCl$_3$): δ=10.0 (s, 1H), 7.93 (d, J=8.4 Hz, 2H), 7.24 (d, J=8.4 Hz, 2H), 3.46 (s, 3H), 3.37 (s, 3H).

Step-2:
S-(4-formylphenyl) dimethylcarbamothioate: O-(4-formylphenyl) dimethylcarbamothioate (3, 1.0 g, 4.7 mmol) was heated at 180° C. in a sealed tube for 6 h. The crude was purified by Combiflash using 15% ethyl acetate in hexane to afford S-(4-formylphenyl) dimethylcarbamothioate 4 as white solid (650 mg, 920).

HRMS (ESI) [M+H]+ calc. for $C_{10}H_{11}NO_2S$ is 209.05, found: 210.00 [M+H]+

$^1$H NMR (400 MHz; CDCl$_3$): δ=9.83 (s, 1H), 7.86 (d, J=8.2 Hz, 2H), 7.67 (d, J=8.2 Hz, 2H), 3.10 (s, 3H), 3.04 (s, 3H).

Step-3:
4-Mercaptobenzaldehyde: To a solution of S-(4-formylphenyl) dimethylcarbamothioate 4 (650 mg, 3.11 mmol) in MeOH (15 mL), 5 N KOH (6.5 mL) was added and the reaction mixture was stirred at 80° C. for 2 h. The mixture was concentrated to remove methanol, neutralized with 1:1 HCl: H$_2$O (pH-7) and extracted with EtOAc (3×50 mL). The combined organic layers were washed with saturated brine and dried (Na$_2$SO$_4$) and concentrated under reduced pressure at 45° C. to afford 4-mercaptobenzaldehyde as colorless liquid (400 mg, 93%). The crude material was used for next steps without purification.

HRMS (ESI) [M+H]+ calc. for $C_7H_6OS$ is 138.01, found: 137.00 [M+H]+

1H NMR (400 MHz; CDCl3): δ=9.92 (s, 1H), 7.73 (d, J=8.4 Hz, 2H), 8.03 (s, 1H), 7.37 (d, J=8.2 Hz, 2H), 3.67 (s, 1H).

Step-4:

4-((4-methylbenzyl)thio)benzaldehyde: To a stirred solution of 4-mercaptobenzaldehyde (5, 400 mg, 2.89 mmol) in ACN (15 mL), $CsCO_3$ (2.8 g, 8.60 mmol) and 4-(bromomethyl)benzaldehyde (6, 404 mg, 1.36 mmol) were added at room temperature (rt). The reaction mixture was stirred for 10 min for same temperature. 1-(bromomethyl)-4-methylbenzene was added in reaction mixture and stirred at 80° C. for 3 h. The reaction mixture was quenched with water (50 mL) and extracted with EtOAc (3×50 mL). The combined organic layers were washed with brine, dried ($Na_2SO_4$) filtered and concentrated under reduced pressure at 45° C. The residue was purified by combiflash using 10% ethyl acetate in hexane to afford 4-((4-methylbenzyl)thio)benzaldehyde (600 mg, 85%) as white solid.

HRMS (ESI) [M+H]+ calc. for $C_{15}H_{14}OS$ was 242.08, found: 241.04 [M−H]−

1H-NMR (400 MHz; CDCl3): δ=9.91 (s, 1H), 7.77 (d, J=8.3 Hz, 2H), 7.37 (d, J=8.3 Hz, 2H), 7.31 (d, J=7.8 Hz, 2H), 7.13 (d, J=7.8 Hz, 2H), 4.23 (s, 2H), 3.37 (s, 3H).

Step-5:

(E)-3-(4-((4-methylbenzyl)thio)benzylidene)-2,3-dihydropyrrolo[1,2-a]quinazolin-5(1H)-one: 2,3-dihydropyrrolo[1,2-a]quinazolin-5(1H)-one (7, 250 mg, 1.34 mmol) and 4-((4-methylbenzyl)thio)benzaldehyde (6, 325 mg, 1.34 mmol) were taken in AcOH (8 mL) and the reaction mixture was stirred at 117° C. for 16 h. The solvent was evaporated under reduced pressure at 45° C. and the residue was purified by prep HPLC to afford (E)-3-(4-((4-methylbenzyl)thio)benzylidene)-2,3-dihydropyrrolo[1,2-a]quinazolin-5 (1H)-one as isomeric mixture of (GTJC-144-009-1) (27 mg, 5%) as light yellow solid.

HRMS (ESI) [M+H]+ calc. for $C_{26}H_{22}N_2OS$ was 410.15, found: 411.20 [M+H]

1H-NMR (400 MHz; CDCl3): δ=8.18 (d, J=7.8 Hz, 1H), 7.95 (s, 1H), 7.69 (t, J=7.0 Hz, 1H), 7.46-7.41 (m, 3H), 7.31 (d, J=8.4 Hz, 2H), 7.26-7.22 (m, 3H), 7.12 (d, J=7.8 Hz, 2H), 4.32 (t, J=6.6 Hz, 2H), 4.16 (s, 2H), 2.33 (s, 3H), 2.33 (s, 3H).

Step-6:

4-((4-methylbenzyl)sulfonyl)benzaldehyde: m-CPBA (172 mg, 0.82 mmol) was added to a solution of 4-((4-methylbenzyl)thio)benzaldehyde (8, 100 mg, 0.41 mmol) in DCM (5 mL) at 0° C. and the reaction mixture was stirred at 0° C. temperature for 3 h. The reaction mixture was quenched with ice cold water (20 mL) and extracted with EtOAc (3×20 mL). The combined organic layers were washed with brine, dried ($Na_2SO_4$), filtered and concentrated under reduced pressure at 45° C. and the residue was purified by Combiflash using 10% ethyl acetate in hexane to afford 4-((4-methylbenzyl)sulfonyl)benzaldehyde (90 mg, 79%) as white solid.

HRMS (ESI) [M+H]+ calc. for $C_{15}H_{14}O_3S$ was 274.07, found: 273.01 [M−H]+

1H-NMR (400 MHz; CDCl3): δ=10.06 (s, 1H), 7.93 (t, J=8.4 Hz, 2H), 7.79 (d, J=8.2 Hz, 2H), 7.06 (d, J=7.4 Hz, 2H), 6.95 (d, J=7.9 Hz, 2H), 4.45 (s, 2H), 2.32 (s, 3H).

Step-7:

(E)-3-(4-((4-methylbenzyl)sulfonyl)benzylidene)-2,3-dihydropyrrolo[1,2-a]quinazolin-5(1H)-one: To a stirred solution of 2,3-dihydropyrrolo[1,2-a]quinazolin-5(1H)-one (8, 60 mg, 032 mmol) in IPA (4 mL), 30% NaOMe (0.3 ml) and 4-((4-methylbenzyl)sulfonyl)benzaldehyde (9, 92 mg, 0.32 mmol) were added at room temperature. The reaction mixture was stirred at 80° C. for 4 hr. After 4 h, the reaction mixture was concentrated directly to get crude product. Crude washed with diethyl ether and pentane and purified by prep HPLC to give (E)-3-(4-((4-methylbenzyl)sulfonyl)benzylidene)-2,3-dihydropyrrolo[1,2-a]quinazolin-5(1H)-one (GTJC-144-009) as a pale yellow solid (10 mg, 7%).

Experimental Procedure for AGS-0925 (GTJC-144-006-1)

Scheme II

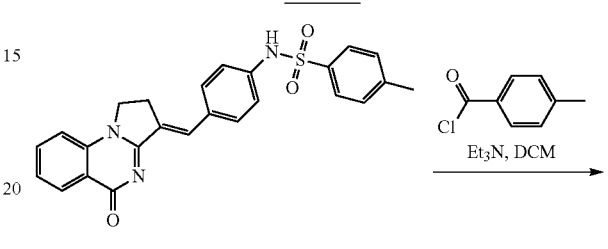

GTJC-144-008

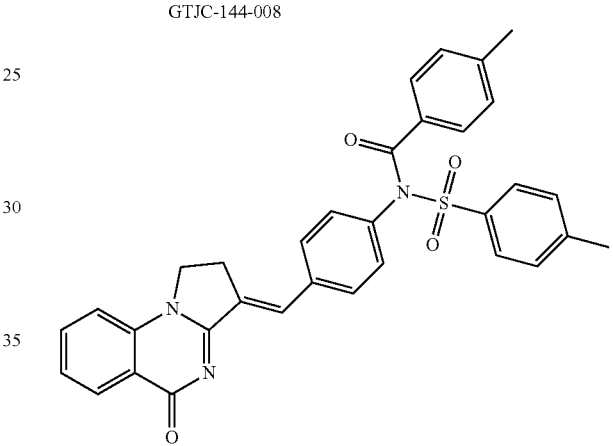

GTJC-144-006

Step-1:

(E)-4-methyl-N-(4-((5-oxo-1,2-dihydropyrrolo[1,2-a]quinazolin-3(5H)-ylidene)methyl)phenyl)-N-tosylbenzamide:

To a solution of (E)-4-methyl-N-(4-((5-oxo-1,2-dihydropyrrolo[1,2-a]quinazolin-3(5H)-ylidene)methyl)phenyl) benzene sulfonamide (GTJC-144-008) (100 mg, 0.225 mmol) in DCM (3 mL), triethylamine (0.3 mL, 0.677 mmol) was added at 0° C. followed by 4-methylbenzoyl chloride (52 mg, 0.338 mmol) at the same temperature and reaction was stirred at room temperature for 3 h. Water was added to the reaction mixture and extracted with DCM (3×25 mL). The combined organic layers were washed with brine and dried ($Na_2SO_4$), filtered, concentrated and the residue was purified by prep. HPLC to afford (E)-4-methyl-N-(4-((5-oxo-1,2-dihydropyrrolo[1,2-a]quinazolin-3(5H)-ylidene)methyl) phenyl)-N-tosylbenzamide (GTJC-144-006) as a brown solid.

HRMS (ESI) [M+H]+ calc. for $C_{33}H_{27}N_3O_4S$ 561.17, found: 562.22 [M+H]+

1H-NMR (400 MHz; DMSO-d6): δ=8.31-8.70 (m, 17H), 4.43 (t, J=4.5 Hz, 2H), 3.36 (s, 2H), 2.43 (s, 3H), 2.21 (s, 3H).

Experimental Procedure for AGS-0907 (GTJC-144-008)

Scheme III

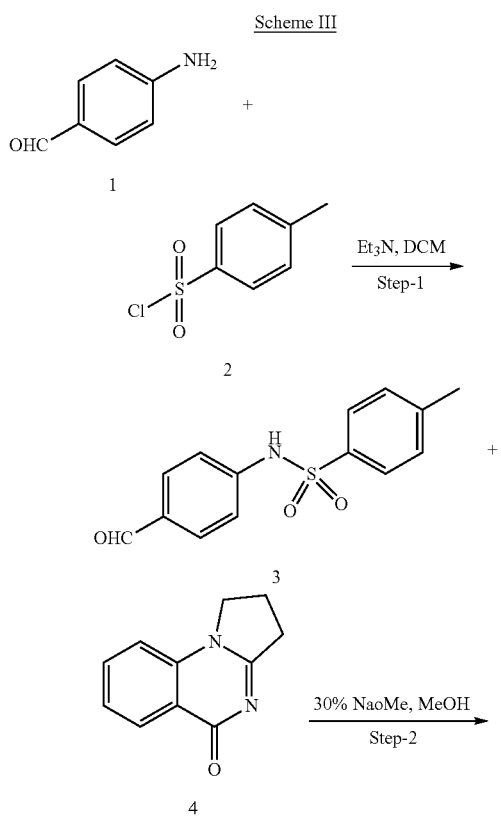

Step-1:
N-(4-formylphenyl)-4-methylbenzenesulfonamide: To a solution of 4-aminobenzaldehyde (200 mg, 1.65 mmol) in DCM (10 mL) triethylamine (0.68 mL, 4.45 mmol) and 4-methylbenzenesulfonyl chloride (471 mg, 2.47 mmol) were added dropwise at 0° C. and reaction was stirred at room temperature for 12 h. Water was added to the reaction mixture and extracted with DCM (3×25 mL). The combined organic layers were washed with brine and dried ($Na_2SO_4$), filtered concentrated and the residue was purified by flash column chromatography eluting with 5% Methanol in DCM to afford N-(4-formylphenyl)-4-methylbenzenesulfonamide (3) as a yellow solid.

HRMS (ESI) $[M+H]^+$ calc. for $C_{14}H_{13}NO_3S$ 275.32, found: 274.18 $[M-H]^+$ LCMS (Method B): m/z 274.18 $(M-H)^+(ES^-)$, at 2.00 min (68.93 m).

$^1$H-NMR (400 MHz; DMSO-$d_6$): δ=10.90 (s, 1H), 9.80 (s, 1H), 7.80-7.77 (m, 2H), 7.75 (d, J=4.8 Hz, 2H), 7.33 (d, J=4.6 Hz, 2H), 7.26 (d, J=4.3 Hz, 2H), 2.49 (s, 3H).

Step-2:
(E)-4-methyl-N-(4-((5-oxo-1,2-dihydropyrrolo[1,2-a]quinazolin-3(5H)-ylidene)methyl)phenyl) benzene sulfonamide (GTJC-144-008): To a solution of 2, 3-dihydropyrrolo[1,2-a]quinazolin-5(1H)-one (4), (70 mg, 0.376 mmol) and N-(4-formylphenyl)-4-methylbenzenesulfonamide (103 mg, 0.376 mmol) in MeOH (5 mL) 30% NaOMe (182.7 mg, 1.128 mmol) was added at 0° C. The reaction mixture was then stirred at 90° C. temperature for 2 h. The reaction mixture was concentrated under vacuum and the residue was washed with diethyl ether (3×15 mL). The solvent was removed under reduced pressure at 45° C. and the residue was purified by Prep HPLC to afford (E)-4-methyl-N-(4-((5-oxo-1,2-dihydropyrrolo[1,2-a]quinazolin-3(5H)-ylidene)methyl)phenyl) benzene sulfonamide (GTJC-144-008) as a white solid (11 mg, 99.26%).

HRMS (ESI) $[M+H]^+$ calc. for $C_{25}H_{21}N_3O_3S$ 443.13, found: 444.44 $[M+H]^+$ LCMS (Method A): m/z 444.44 $(M+H)^{3o}(ES^{3o})$ at 5.18 min (68.33%) and 5.54 min (30.93%)

$^1$H-NMR (400 MHz; DMSO-$d_6$): δ=10.65 (s, 1H), 8.08 (d, J=7.36 Hz, 1H), 7.83 (t, J=8.0 Hz, 1H), 7.71 (d, J=8.4 Hz, 2H), 7.57 (d, J=2.4 Hz, 4H), 7.51 (t, J=7.6 Hz, 1H), 7.37 (d, J=8.0 Hz, 2H), 7.21 (d, J=8.4 Hz, 2H), 4.36 (t, J=6.8 Hz, 2H), 3.32-3.29 (m, 2H), 2.33 (s, 3H).

Experimental Procedure for AGS-0921 (GTJC-144-008-1)

Scheme IV

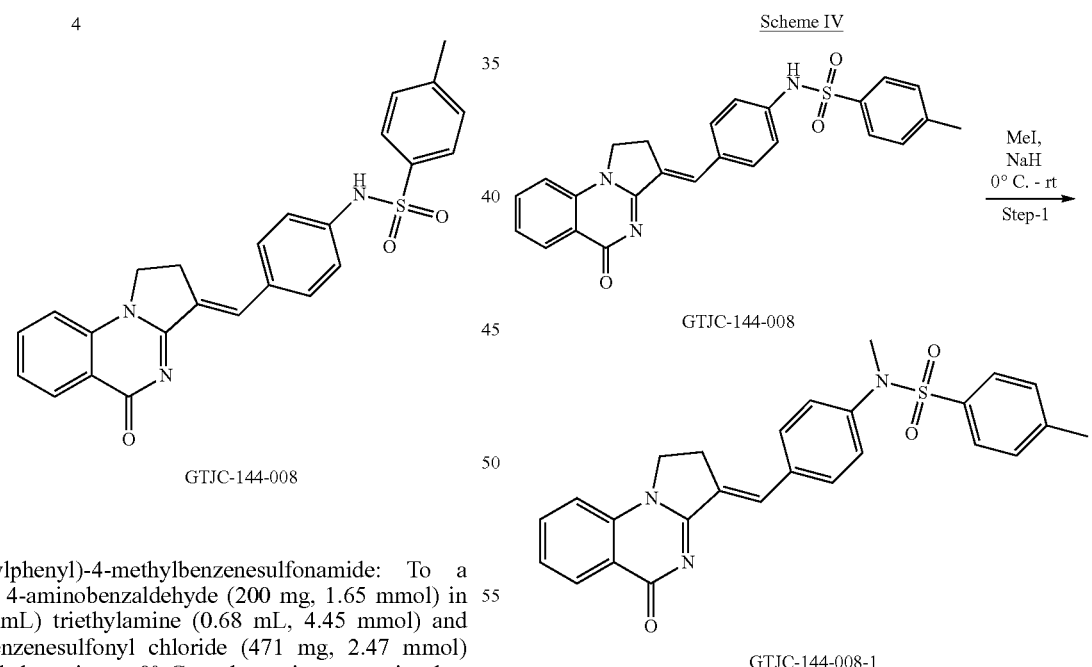

Step-1:

Synthesis of (E)-N,4-dimethyl-N-(4-((5-oxo-1,2-dihydropyrrolo[1,2-a]quinazolin-3(5H)-ylidene)methyl)phenyl)benzenesulfonamide To a solution of (E)-4-methyl-N-(4-((5-oxo-1,2-dihydropyrrolo[1,2-a]quinazolin-3(5H)-ylidene)methyl)phenyl) benzene sulfonamide (GTJC-144-008) (150 mg, 0.3386 mmol) in THF (10 mL), NaH (34 mg, 0.6772 mmol) was added at 0° C. After stirring for 30 min methyliodide (120 mg, 0.8465 mmol) was added dropwise at the same temperature and reaction mixture was stirred at room temperature for 1 h. The reaction mixture was quenched with NH₄Cl diluted with water and extracted with ethyl acetate (3×15 mL). The combined organic layers were washed with brine and dried (Na₂SO₄), filtered concentrated and the residue was purified by Prep HPLC to afford (E)-N,4-dimethyl-N-(4-((5-oxo-1,2-dihydropyrrolo [1,2-a] quinazolin-3 (5H)-ylidene)methyl)phenyl)benzenesulfonamide (GTJC-144-008-1) as a brown solid.

HRMS (ESI) [M+H]⁺ calc. for $C_{26}H_{23}N_3O_3S$ 457.55, found: 458.29 [M–H]⁺

¹H-NMR (400 MHz; DMSO-d₆): δ=8.11 (d, J=7.5 Hz, 1H), 7.7 (t, J=7.1 Hz, 1H), 7.67 (d, J=8.2 Hz, 2H), 7.45 (d, J=3.6 Hz, 4H), 7.35 (t, J=6.8 Hz, 1H), 7.30 (d, J=8.1 Hz, 2H), 7.21 (d, J=7.7 Hz, 2H), 4.30 (t, J=6.5 Hz, 2H), 3.32-3.25 (m, 2H), 3.20 (s, 3H), 2.34 (s, 3H).

Experimental Synthesis Procedure for G-926

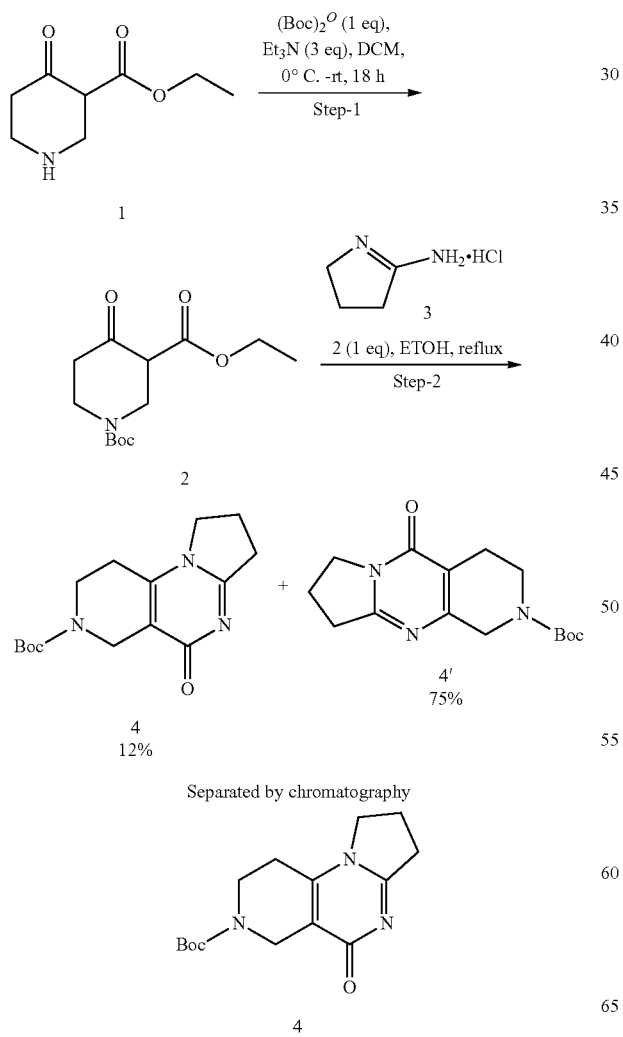

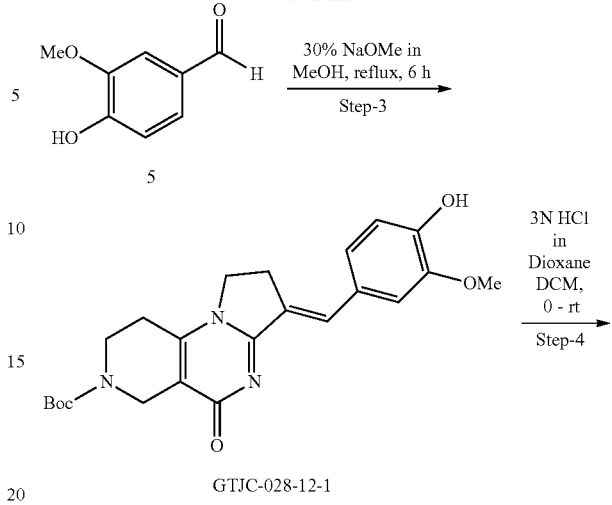

In this synthetic scheme the Me-o- group on intermediate 5 represents variety of potential aryl structure [Rx-O-] that may strengthen the binding coeffiecent of the compound, increase its affinity to the Gal-3, affecting the ligand binding and/or the pharmacokinetic profile of the compound including its oral bioavailability.

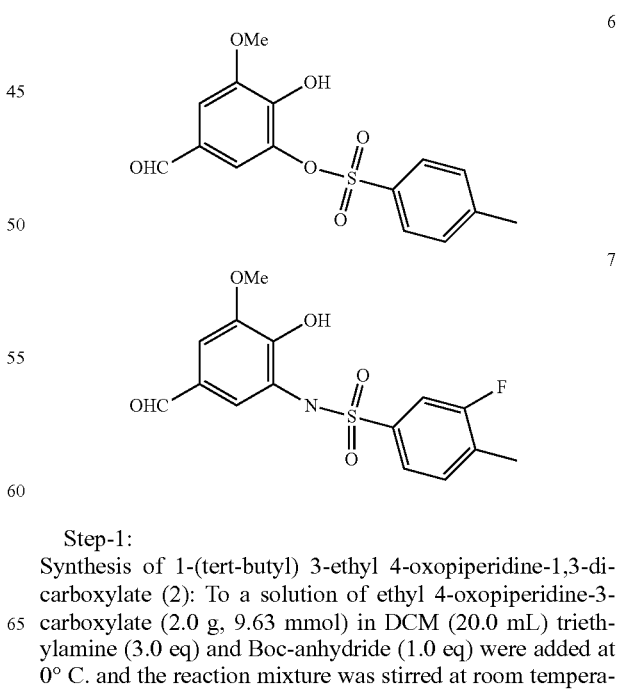

Step-1:
Synthesis of 1-(tert-butyl) 3-ethyl 4-oxopiperidine-1,3-dicarboxylate (2): To a solution of ethyl 4-oxopiperidine-3-carboxylate (2.0 g, 9.63 mmol) in DCM (20.0 mL) triethylamine (3.0 eq) and Boc-anhydride (1.0 eq) were added at 0° C. and the reaction mixture was stirred at room temperature for 18 h. Water was added to the reaction mixture and extracted with DCM (3×25 mL)). The combined organic layers were washed with brine and dried ($Na_2SO_4$). The solvent was removed under reduced pressure at 45° C. and the residue was purified by flash column chromatography eluting with 5% MeOH in DCM to afford 1-(tert-butyl) 3-ethyl 4-oxopiperidine-1,3-dicarboxylate (2) as colorless syrup.

$^1$H-NMR (400 MHz; $CDCl_3$): δ=4.23 (t, J=6.2 Hz, 3H), 4.05 (s, 2H), 3.56 (t, J=7.0 Hz, 2H), 2.58 (s, 2H), 1.46 (s, 9H), 1.40 (t, J=5.6 Hz, 3H).

Step-2:

tert-butyl 5-oxo-1,4,5,7,8,9-hexahydropyrido[3,4-e]pyrrolo[1,2-a]pyrimidine-3(2H)-carboxylate (4)

To a solution of 3,4-dihydro-2H-pyrrol-5-amine hydrochloride (3, 1998 mg, 7.375 mmol) in EtOH (5 mL) added 30% NaOMe in methanol (6 mL) and 1-(tert-butyl) 3-ethyl 4-oxopiperidine-1,3-dicarboxylate (4, 885 mg, 7.375 mmol) were added at room temperature. The reaction mixture was stirred at 80° C. temperature for 8 h. After completion the reaction mixture was concentrated under reduced pressure at 45° C., to give the crude. The crude reaction mixture was purified by flash column chromatography to afford tert-butyl 5-oxo-1,4,5,7,8,9-hexahydropyrido[3,4-e]pyrrolo[1,2-a]pyrimidine-3(2H)-carboxylate (4) as colorless gum.

HRMS (ESI) [M+H]$^+$ calc. for $C_{15}H_{21}N_3O_3$ 291.16, found: 292.15 [M+H]$^+$ LCMS (Method A): m/z 292.15 (M+H)$^{30}$(ES$^{30}$), at 4 min (99.16%).

$^1$H-NMR (400 MHz; $CDCl_3$): δ=4.30 (s, 2H), 4.03 (t, J=6.5 Hz, 2H), 3.71 (t, J=6.1 Hz, 2H), 3.07 (t, J=6.3 Hz, 2H), 2.60 (s, 2H), 2.33-2.27 (m, 2H), 1.46 (s, 9H).

Step-3:

tert-butyl 7-(4-hydroxy-3-methoxybenzylidene)-5-oxo-1,4,5,7,8,9-hexahydropyrido[3,4-e]pyrrolo[1,2-a]pyrimidine-3(2H)-carboxylate (GTJC-028-12-1)

To a solution of tert-butyl 5-oxo-1,4,5,7,8,9-hexahydropyrido[3,4-e]pyrrolo[1,2-a]pyrimidine-3(2H)-carboxylate (4, 130 mg, 0.446 mmol) in IPA (10 mL), 30% NaOMe in methanol (0.3 ml) and 1-(tert-butyl) 3-ethyl 4-oxopiperidine-1,3-dicarboxylate (4, 885 mg, 7.375 mmol) were added at rt. The reaction mixture was stirred at 90° C. for 24 h. After completion the reaction mixture was concentrated under reduced pressure at 45° C., to give the crude. The crude reaction mixture was purified by Flash column chromatography eluting with 5% MeOH in DCM to afford tert-butyl 7-(4-hydroxy-3-methoxybenzylidene)-5-oxo-1,4,5,7,8,9-hexahydropyrido[3,4-e]pyrrolo[1,2-a]pyrimidine-3(2H)-carboxylate as yellow solid (GTJC-028-12-1).

HRMS (ESI) [M+H]$^+$ calc. for $C_{23}H_{27}N_3O_5$ 425.20, found: 426.23 [M+H]$^+$ LCMS (Method A): m/z 426.23 (M+H)$^{30}$(ES$^{30}$), at 10 min (98.94%).

$^1$H-NMR (400 MHz; $CDCl_3$): δ=9.55 (s, 1H), 7.48 (s, 1H), 7.18 (s, 1H), 7.09 (d, J=7.6 Hz, 1H), 6.88 (d, J=8.2 Hz, 1H), 4.18-4.14 (t, 2H), 4.09 (s, 2H), 3.83 (s, 3H), 3.61 (t, J=6.2 Hz, 2H), 3.24 (t, J=6.0 Hz, 2H), 2.70 (t, J=6.4 Hz, 2H), 1.42 (s, 9H).

Step-4:

7-(4-hydroxy-3-methoxybenzylidene)-1,2,3,4,8,9-hexahydropyrido[3,4-e]pyrrolo[1,2-a]pyrimidin-5(7H)-one (GTJC-028-12-2)

To a solution of tert-butyl 7-(4-hydroxy-3-methoxybenzylidene)-5-oxo-1,4,5,7,8,9-hexahydropyrido[3,4-e]pyrrolo[1,2-a]pyrimidine-3(2H)-carboxylate (60 mg, 0.141 mmol) in DCM (5 mL) was added 3N HCl in Dioxane (0.2 mL) at 0° C. The reaction mixture was the stirred at room temperature for 2 h. After completion the reaction mixture was concentrated under reduced pressure at 45° C., and the residue was titurated with diethylether to afford 7-(4-hydroxy-3-methoxybenzylidene)-1,2,3,4,8,9-hexahydropyrido[3,4-e]pyrrolo[1,2-a]pyrimidin-5(7H)-one as light yellow solid (GTJC-028-12-2).

HRMS (ESI) [M+H]$^+$ calc. for $C_{18}H_{19}N_3O_3$ 325.14, found: 326.05 [M+H]$^+$ LCMS (Method A): m/z 326.05 (M+H)$^{30}$(ES$^{30}$), at 10 min (99.65%).

$^1$H-NMR (400 MHz; DMSO-$d_6$): δ=9.55 (s, 2H), 7.60 (s, 1H), 7.19 (s, 1H), 7.13 (d, J=1.92 Hz, 1H), 6.92 (d, J=8.2 Hz, 2H), 4.26 (t, J=6.3 Hz, 2H), 3.84 (s, 3H), 3.30 (t, J=6.2 Hz, 2H), 3.30 (t, J=6.4 Hz, 2H), 2.96 (t, J=6.2 Hz, 2H).

Experimental Procedure for AGS-0923 (GTJC-028-021) Scheme VI

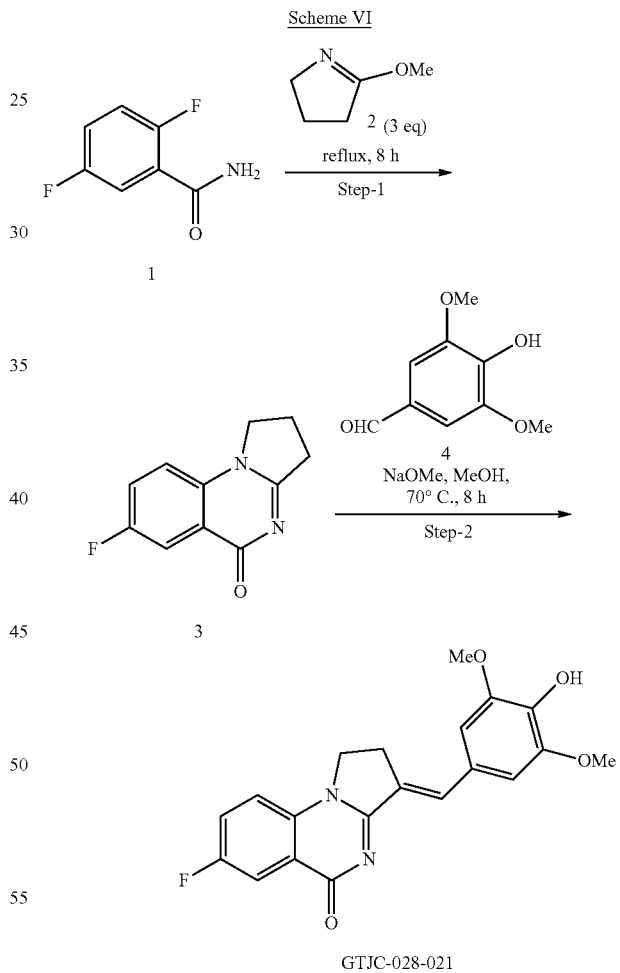

Step-1:

7-fluoro-2,3-dihydropyrrolo[1,2-a]quinazolin-5(1H)-one (3)

A mixture of 2,5-difluorobenzamide (500 mg, 3.18 mmol) and 5-methoxy-3,4-dihydro-2H-pyrrole (945 mg, 9.54 mmol) were heated at 120° C. for 8 h. The reaction mixture was cooled to rt and dissolved in 5% MeOH in DCM and concentrated in vacuo. The crude was purified by Combiflash using 5% MeOH in DCM to afford 7-fluoro-2,3-dihydropyrrolo[1,2-a]quinazolin-5(1H)-one (3) as light red solid.

HRMS (ESI) [M+H]+ calc. for $C_{11}H_9FN_2O$ 204.07, found: 205.01 [M+H]+

LCMS (Method A): m/z 205.01 (M+H)³⁰(ES³⁰), at 4.00 min (95.32%).

¹H-NMR (400 MHz; DMSO-$d_6$): δ=7.73-7.70 (m, 2H), 7.61-7.58 (m, 1H), 4.26 (t, J=6.2 Hz, 2H), 3.05-3.01 (t, J=6.4 Hz, 2H), 2.27-2.23 (m, 2H).

Step-2:

(E)-7-fluoro-3-(4-hydroxy-3,5-dimethoxybenzylidene)-2,3-dihydropyrrolo[1,2-a]quinazolin-5(1H)-one (GTJC-028-021)

To a solution of 7-fluoro-2,3-dihydropyrrolo[1,2-a]quinazolin-5(1H)-one (3, 220 mg, 0.927 mmol) in Methanol (5 mL), 30% NaOMe in methanol (2 mL) and 4-hydroxy-3,5-dimethoxybenzaldehyde (4, 337 mg, 1.85 mmol) were added at rt. The reaction mixture was stirred at 70° C. temperature for 8 h. After completion the reaction mixture was concentrated under reduced pressure at 45° C. The residue was purified by Prep column chromatography to give (E)-7-fluoro-3-(4-hydroxy-3, 5-dimethoxybenzylidene)-2,3-dihydropyrrolo[1,2-a]quinazolin-5(1H)-one (GTJC-028-002) as light brownish solid (24 mg, 11%).

HRMS (ESI) [M+H]+ calc. for $C_{20}H_{17}FN_2O_4$ 368.12, found: 369.07 [M+H]+

LCMS (Method A): m/z 369.07 (M+H)³⁰(ES³⁰), at 10 min (97.33%).

¹H-NMR (400 MHz; DMSO-$d_6$): δ=9.00 (s, 1H), 7.75-7.70 (m, 2H), 7.72-7.67 (m, 2H), 6.97 (s, 2H), 4.40-4.36 (m, 2H), 3.87 (s, 6H), 3.39-3.38 (m, 2H).

Experimental Procedure for AGS-924

Scheme VII

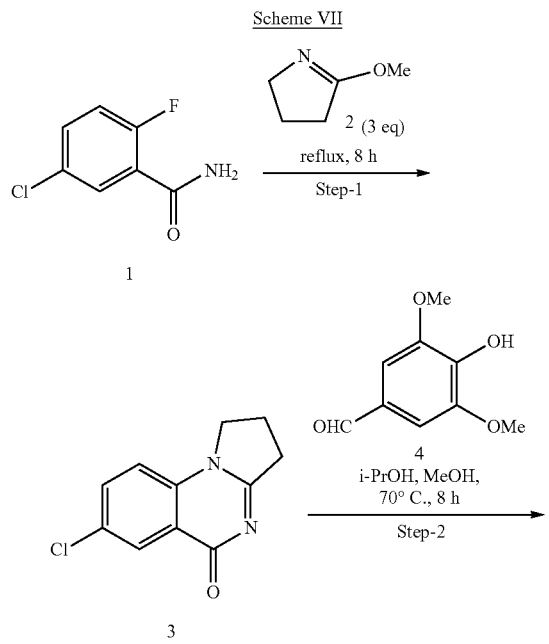

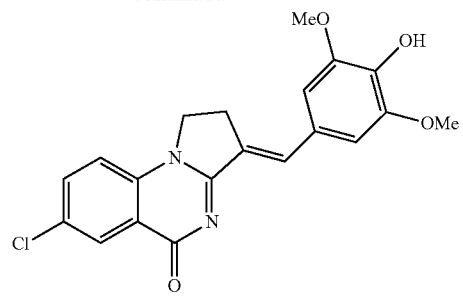

GTJC-028-022

Step-1:

7-chloro-2,3-dihydropyrrolo[1,2-a]quinazolin-5(1H)-one (3) A mixture of 5-chloro-2-fluorobenzamide (3, 500 mg, 2.89 mmol) and 5-methoxy-3,4-dihydro-2H-pyrrole (858 mg, 8.67 mmol) were heated at 120° C. for 8 h. The reaction mixture was cooled to room temperature dissolved in 5% MeOH in DCM and concentrated in vacuo. The residue was purified by Combiflash eluting with 5% MeOH in DCM to afford 7-chloro-2,3-dihydropyrrolo[1,2-a]quinazolin-5(1H)-one (3) as a light red solid.

HRMS (ESI) [M+H]+ calc. for $C_{11}H_9ClN_2O$, 220.04 found: 221.04 [M+H]+

LCMS (Method H): m/z 221 (M+H)³⁰(ES³⁰), at 4.12 min (92.58%).

¹H-NMR (400 MHz; DMSO-$d_6$): δ=7.97 (s, 1H), 7.07-7.85 (m, 1H), 7.57 (d, J=6.4 Hz, 1H), 4.26 (t, J=6.3 Hz, 2H), 3.05- (t, J=6.6 Hz, 2H), 2.25 (t, J=6.0 Hz, 2H).

Step-2:

(E)-7-chloro-3-(4-hydroxy-3,5-dimethoxybenzylidene)-2,3-dihydropyrrolo[1,2-a]quinazolin-5(1H)-one (AGS-0934, GTJC-028-022):

To a solution of 7-chloro-2,3-dihydropyrrolo[1,2-a]quinazolin-5(1H)-one (3, 380 mg, 1.77 mmol) in isopropanol (10 mL), 30% NaOMe in methanol (3.5 mL) and 4-hydroxy-3,5-dimethoxybenzaldehyde (4, 345 mg, 1.89 mmol) were added at rt. The reaction mixture was stirred at 70° C. temperature for 8 h. The reaction mixture was concentrated under reduced pressure at 45° C. and the residue was purified by Prep HPLC to afford (E)-7-chloro-3-(4-hydroxy-3,5-dimethoxybenzylidene)-2,3-dihydropyrrolo[1,2 a]quinazolin-5(1H)-one (GTJC-028-022) as a yellow solid (4 mg, 10%).

HRMS (ESI) [M+H]+ calc. for $C_{20}H_{17}ClN_2O4$, 384.09, found: 385.10 [M+H]+

LCMS (Method A): m/z 385.10 (M+H)³⁰(ES³⁰), at 10 min (85.00%).

¹H-NMR (400 MHz; DMSO-$d_6$): δ=8.01 (s, 1H), 7.88 (t, J=6.6 Hz, 1H), 7.69 (s, 1H), 7.62-7.59 (d, J=12.0 Hz, 2H), 6.89 (s, 2H), 4.40 (t, J=6.2 Hz, 2H), 3.81 (s, 6H), 3.40 (t, J=6.1 Hz. 2H).

Experimental Procedure for AGS-0934 (GTJC-028-023)

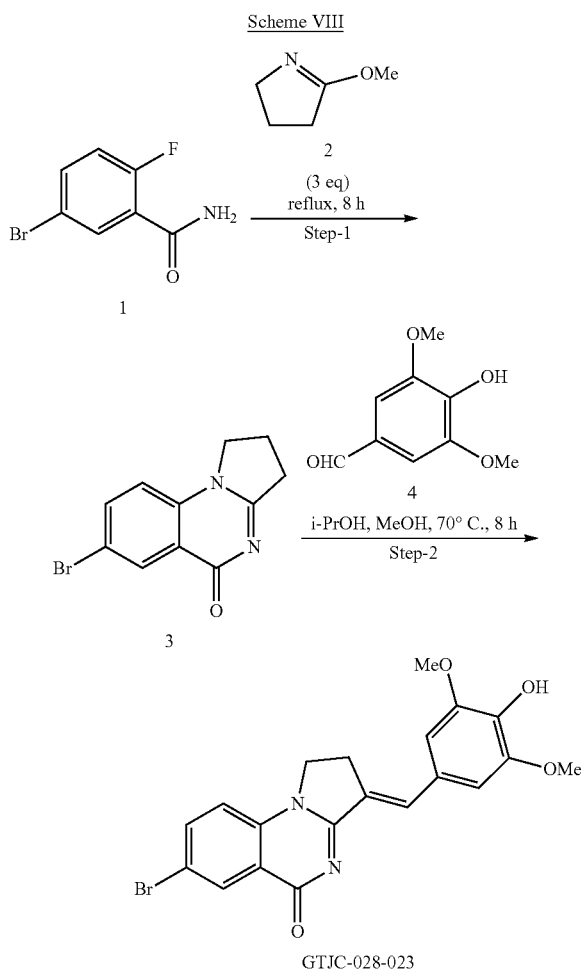

Scheme VIII

GTJC-028-023

Step-1:
7-bromo-2,3-dihydropyrrolo[1,2-a]quinazolin-5(1H)-one (3): A mixture of 5-bromo-2-fluorobenzamide (1, 600 gm, 2.76 mmol) and 5-methoxy-3,4-dihydro-2H-pyrrole (2, 995 mg, 179.6 mmol) were heated at 120° C. for 8 h. The reaction mixture was cooled to room temperature, dissolved in 5% MeOH in DCM and concentrated in vacuo. The residue was purified by Combiflash eluting with 5% MeOH in DCM to afford 7-bromo-2,3-dihydropyrrolo[1,2-a]quinazolin-5(1H)-one (3) as a light brown solid.

HRMS (ESI) [M+H]$^+$ calc. for $C_{11}H_9BrN_2O$ 264, found: 265 [M+H]$^+$ and 267 [M+H+2]$^+$ LCMS (Method B): m/z 265 (M+H)$^{30}$(ES$^{30}$), at 4.12 min (99.54%).

$^1$H-NMR (400 MHz; DMSO-d$_6$): δ=8.11 (s, 1H), 7.99-7.97 (d, J=8.0 Hz, 1H), 7.50 (d, J=8.3 Hz, 1H), 4.25-4.22 (m, 2H), 3.05 (t, J=5.6 Hz, 2H), 2.26 (t, J=6.0 Hz, 2H).

Step-2:

Synthesis of (E)-7-bromo-3-(4-hydroxy-3,5-dimethoxybenzylidene)-2,3-dihydropyrrolo[1,2-a]quinazolin-5(1H)-one (AGS-0924, GTJC-028-023)

To a solution of 7-bromo-2,3-dihydropyrrolo[1,2-a]quinazolin-5(1H)-one (3,400 mg, 1.51 mmol) in isopropanol (8 mL), 30% NaOMe in methanol (2.0 mL) and 4-hydroxy-3,5-dimethoxybenzaldehyde (4, 330 mg, 1.818 mmol) were added at room temperature. The reaction mixture was stirred at 70° C. for 8 h. The reaction mixture was concentrated under reduced pressure at 45° C. and the residue was purified by Prep HPLC to afford (E)-7-bromo-3-(4-hydroxy-3,5-dimethoxybenzylidene)-2,3-dihydropyrrolo[1,2-a]quinazolin-5(1H)-one (GTJC-028-002) as a light yellow solid, (4 mg, 10%).

HRMS (ESI) [M+H]$^+$ calc. for $C_{20}H_{17}BrN_2O_4$ 428.04, found: 429 [M+H]$^+$ and 431 [M+H+2]$^+$ LCMS (Method A): m/z 429.05 (M+H)$^{30}$(ES$^{30}$), at 10 min (92.32%).

$^1$H-NMR (400 MHz; DMSO-d$_6$): δ=8.92 (s, 1H), 8.13 (d, J=2.0 Hz, 1H), 7.99-7.97 (m, 1H), 7.67 (s, 1H), 7.56-7.54 (m, 1H), 6.97 (s, 2H), 4.38 (t, J=6.3 Hz, 2H), 3.84 (s, 6H), 3.397 (t, J=6.6 Hz, 2H).

EXAMPLES

The identified compounds were synthesized and purified by conventional high performance chromatography and then validated for structure, purity and isomers composition by NMR and LC-MS. Compounds were then screen for binding to Gal-3 by multiple in-vitro and in-vivo assays.

Examples are given for proprietary compounds described herein that have significant physiological effect on galectins and more specific on Gal-3 functionality in-vitro and in-vivo:

Examples are given for compounds described herein (Tables 2, 3 and 4) that may have significant physiological effect on galectins or may serve as intermediates for further integrated into fused structures (as demonstrated in Table 3) to produce enhanced binding specificity to Gal-3 or other galectin and attenuate its functionality and pathological manifestation.

Figure 4:
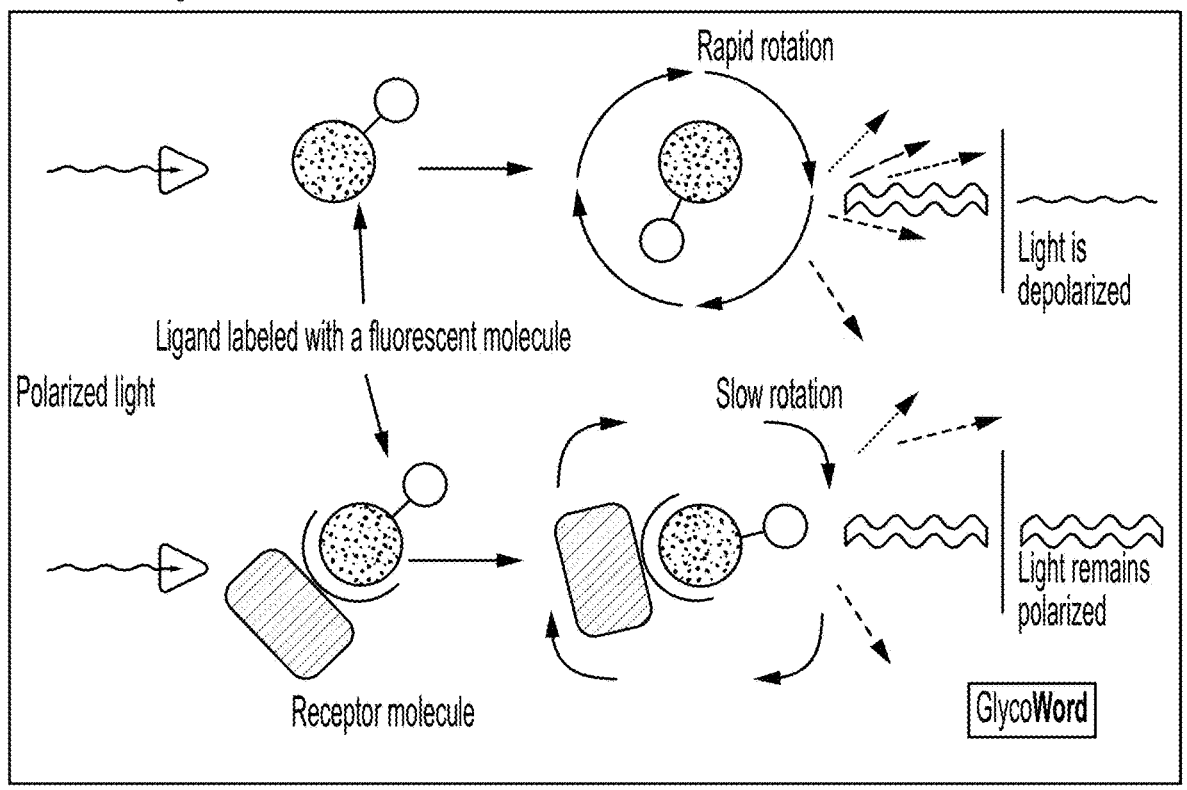
FIG. 4 depicts a method using Fluorescent Polarization (FP) to show interaction of fluorescent ligand (FL) with the CRD of Gal-3 according to embodiments of the invention. A potential inhibitor that binds to the CRD will compete with the FL and reduce the polarization signal.

Example 1: Compound Inhibition of Galectin' CRD (Carbohydrate Recognition Domain) Binding to Fluorescent Probes Fluorescent molecules in solution, excited with a polarized light, emit light into a fixed plane if the molecules remain immobilized during the fluorophore's excitation. However, the molecule will emit light into a multiple plane if the molecule freely rotates and tumbles during the fluorophore's excitation. Therefore, when fluorescent molecule binds to a large molecule such as protein, the emitted light remains polarized, however, in free unbound state the light is obviously depolarized (FIG. 4).

Fluorescein-labeled carbohydrate probes have been developed which bind to Gal-3 and other galectin proteins and these probes have been used to establish assays that measure the binding affinity of compounds for the galectin proteins using interference with the Fluorescence Polarization signal. Compounds described herein avidly bind to Gal-3, as well as other galectin proteins like Galectin-1, Galectin-8, galectin-9 and others. Using this assay and displace the probe with high affinity, with IC$_{50}$'s (concentration at 50% inhibition) of between 5 ηM to 20 μM. In some embodiments, the compounds described herein have an IC50 of between 5 nM and 10 nM, from 5 nM and 100 nM, from 5 nM to 1 μM, from 5 nM to 10 μM, from 10 nM to 100 nM, from 10 nM to 1 μM, from 10 nM to 10 μM, from 10 nM to 20 μM, from 100 nM to 1 μM, from 100 nM to 10 μM, from 100 nM to 20 μM, from 1 μM to 10 μM, from 1 μM to 20 μM, from 10 μM to 20 μM, etc . . .

Allosteric compounds interference with a small fluorescein probe binding has been in general weaker than the observation with galectin interaction with the natural larger glycoproteins ligands of galectins. This method was more effective in measuring small molecules of galactose derivatives.

Figure 8A:
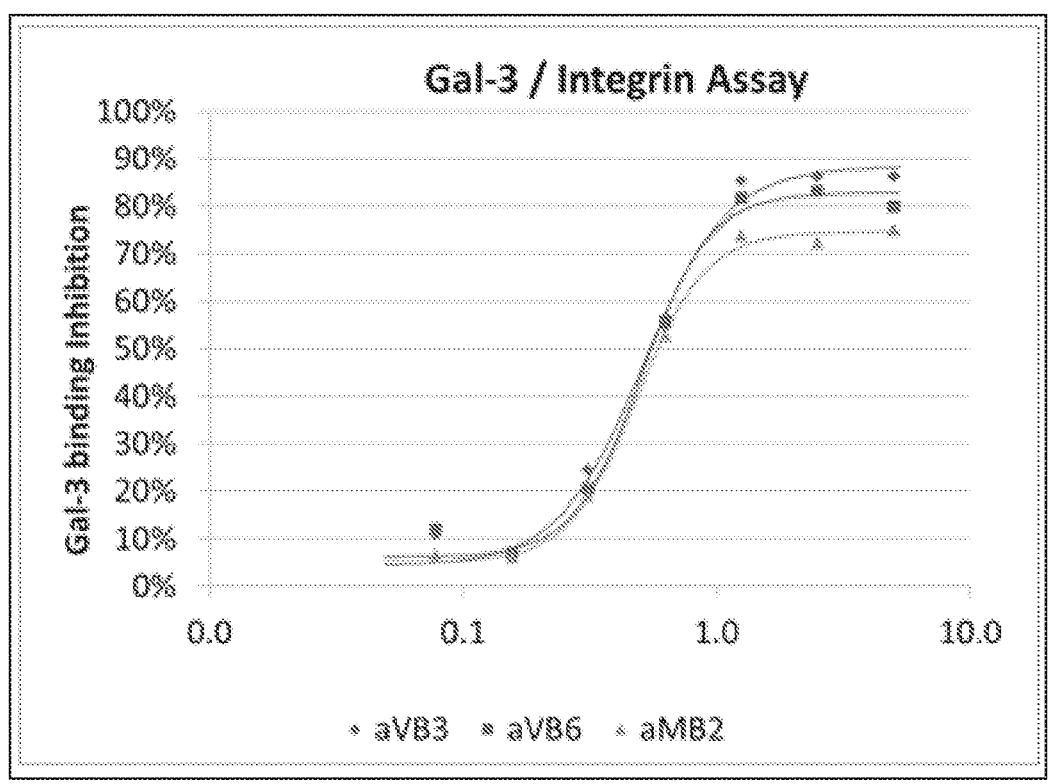
FIG. 8A shows comparison of inhibition of various integrins interaction with Gal-3 by compound AGS-0028 according to embodiments of the invention.
Figure 8B:
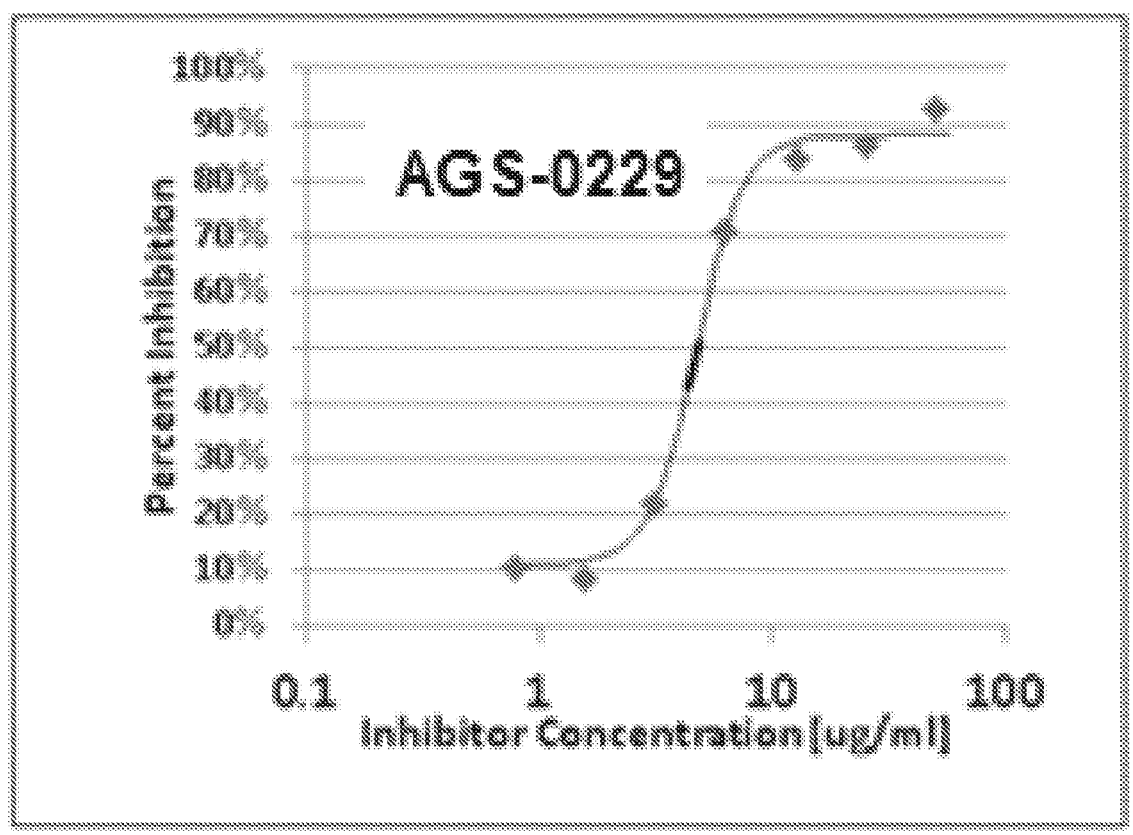
FIGS. 8B and 8C show the inhibition of Integrin αMP2 interaction with Gal-3 by AGS-0229, an allosteric compound (FIG. 8B) and TD-139 (FIG. 8C), a galactose derivative compound according to embodiments of the invention.
Figure 8C:
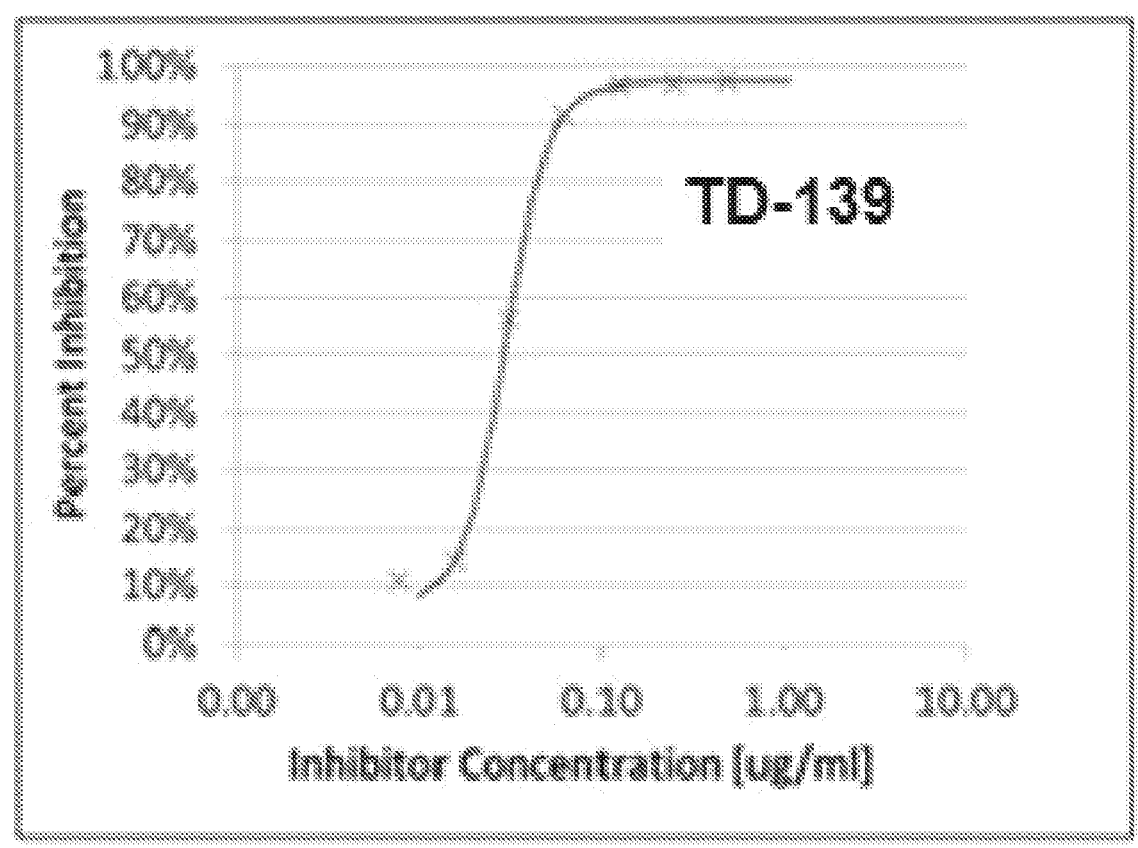

For example, a digalactoside derivative causing significant inhibition of polarization when tested against an either a small FITC linked lactose derivative (SEE FIG. 5B) or the more complex interaction of glycoprotein ligand like Integrin αMβ2 (See FIG. 8C). However, allosteric compound (as in Examples 1A, 2 and 3) may only slightly effect interaction of small FITC-lactose derivative (See FIG. 5A) but will significantly affect the more complex interaction with glycoproteins ligand like Integrin αMβ2 and αVβ6 (See FIGS. 8A and 8B).

Example 2: Compound Inhibition of Transfer of Resonance Energy Between the Galectin' Chromophore (Donor) and a Fluorescent Ligand (Acceptor)

Fluorescence Resonance Energy Transfer (FRET) is a method suitable to evaluate binding of relative small molecule to a bind site of a larger acceptor molecule. The FRET is a physical phenomenon that is being used regularly in drug discovery. FRET signal sensitivity relies on the distance-dependent transfer of energy due to a donor molecule interaction with an acceptor molecule. Upon interaction the donor molecule' chromophore that initially absorbs the energy subsequently transfer it to the acceptor' chromophore. The transfer of energy leads to a reduction in the donor's fluorescence intensity and excited state lifetime, and an increase in the acceptor's emission intensity. A pair of molecules that interact in such a manner that FRET occurs is often referred to as a donor/acceptor pair.

Figure 6:
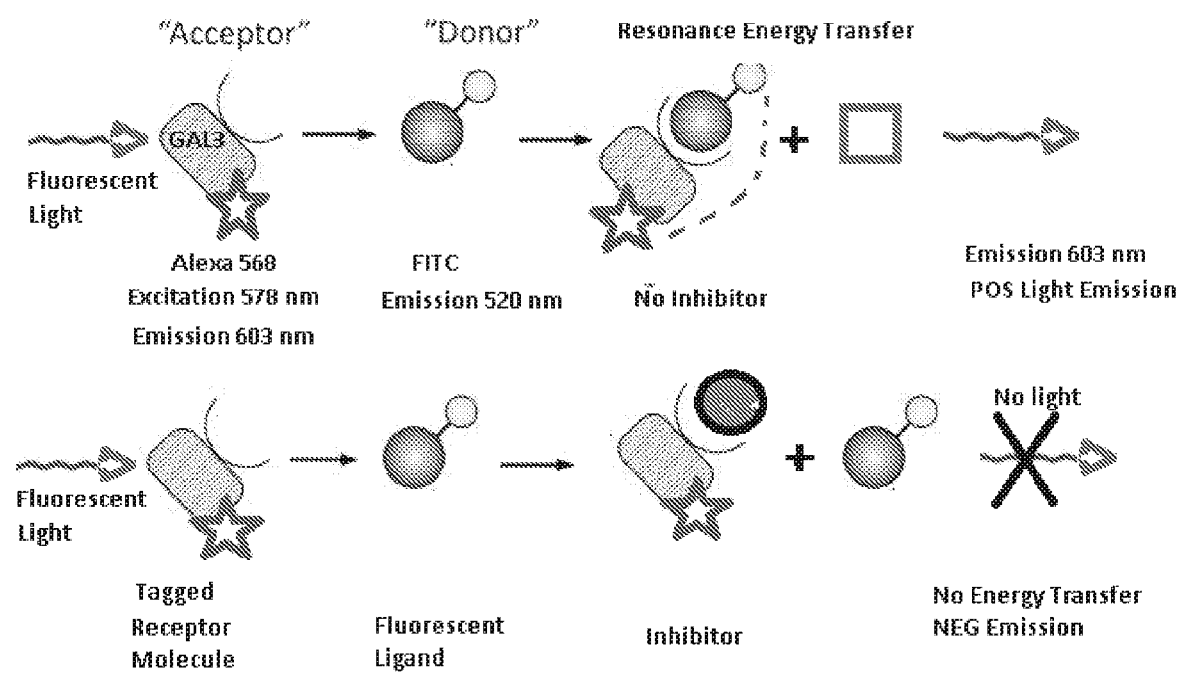
FIG. 6 is schematic representation of fluorescence resonance energy transfer (FRET) analytical method using a fluorescent tagged (DONOR) ligand to measure interaction with the target Galectin-3 tagged with fluorescent emission compound (ACCEPTOR). Interaction by two fluorescence-tagged molecules creates a fluorescence resonance energy transfer (FRET) between a fluorescent "DONOR" ligand and the target Gal-3 tagged with fluorescent emission compound "ACCEPTOR" according to embodiments of the invention.

FRET assay was adapted for evaluating the interaction of chromophore tagged galectins with galactose fluorescent-donor probe that when binding to the CRD has positive emission (See FIG. 6). The method was found effective to verify that compounds described herein avidly bind to Gal-3, as well as other galectin proteins and reduce the emission intensity. Using this assay IC50's (inhibition concentration of 50%) has been established in the range of 5 ηM to 20 μM.

In some embodiments, the compounds described herein have an IC50 of between 5 nM and 10 nM, from 5 nM and 100 nM, from 5 nM to 1 μM, from 5 nM to 10 μM, from 10 nM to 100 nM, from 10 nM to 1 μM, from 10 nM to 10 μM, from 10 nM to 20 μM, from 100 nM to 1 μM, from 100 nM to 10 μM, from 100 nM to 20 μM, from 1 μM to 10 μM, from 1 μM to 20 μM, from 10 μM to 20 μM, etc . . .

Example 3: Compound Inhibition of Galectin Binding to Physiological Ligands

Galectin proteins, including but not limited to Gal-3 and galectin-1, have multiple biologically relevant binding ligands in mammalian species, including but not limited to rodents, primates, and humans. Galectins are carbohydrate-binding proteins that bind to glycoproteins with P-galactoside-containing sugars The result of binding of galectin proteins to these ligands results in a plethora of biological effects in and on cells and in tissues and whole organisms including regulating cell survival and signaling, influencing cell growth and chemotaxis, interfering with cytokine secretion, mediating cell-cell and cell-matrix interactions or influencing tumor progression and metastasis. Additionally, changes in normal expression of galectin proteins are responsible for pathological effects in multiple diseases, including but not limited to inflammatory, fibrotic and neoplastic diseases.

Compounds described herein are designed to attenuate the carbohydrate recognition domain of galectin proteins, with higher specificity to Gal-3, and disrupt its interactions with biologically relevant ligands. They are intended to inhibit the function of galectin proteins that may be involved in pathological processes at normal levels of expression or in situations where they are increased over physiological levels.

Some of the ligands for galectin proteins that are important in normal cellular function and pathology in disease include, but are not limited to, integrins, Gal-3 binding protein, TIM-3 (T cell immunoglobulin mucin-3), CD8, T cell receptor, transforming growth factor-O receptors (TGF-β Rs), laminins, fibronectins, BCR (B cell receptor, CTLA-4 (cytotoxic T-lymphocyte-associated protein-4), EGFR (Epidermal growth factor receptor), FGFR (fibroblast growth factor receptor), GLUT-2 (glucose transporter-2), IGFR (insulin-like growth factor receptor), insulin receptor, various interleukins, LPG (lipophosphoglycan), MHC (major histocompatibility complex), PDGFR (platelet-derived growth factor receptor), TCR (T cell receptor), CD98, Mac3 antigen (Lysosome-associated membrane protein 2 (LAMP2) also known as CD107b (Cluster of Differentiation 107b) and others.

Experiments have been performed to evaluate the physical interaction of galectin proteins with these various biological ligands mediating cellular functions as well as with specific antibodies to the galectins. The design of these experiments was used to evaluate the interaction between various Gal-3 ligands and determine whether compounds described herein are able to inhibit these interactions, as shown in diagrams in FIGS. 7A and 7B.

Figure 7A:
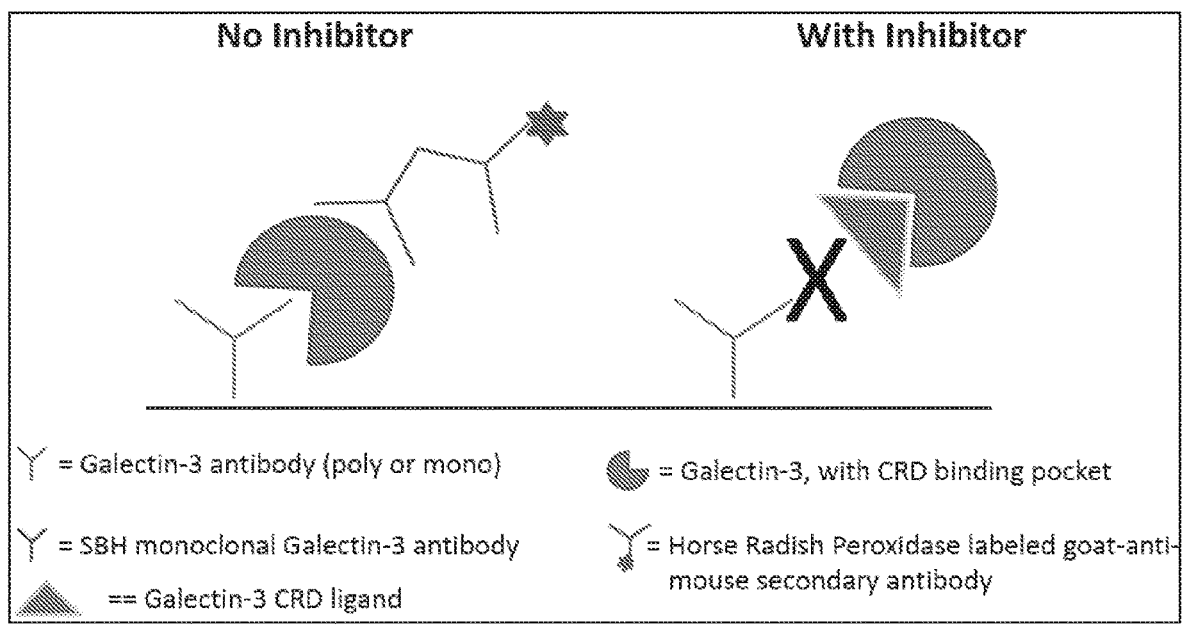
FIG. 7A illustrates a sandwich ELISA method using 2 specific antibodies to Gal-3 whose interaction with Gal-3 is sensitive to the CRD occupation status according to embodiments of the invention. Thus, a compound that interacts with the CRD will inhibit the ELISA signal.
Figure 7B:
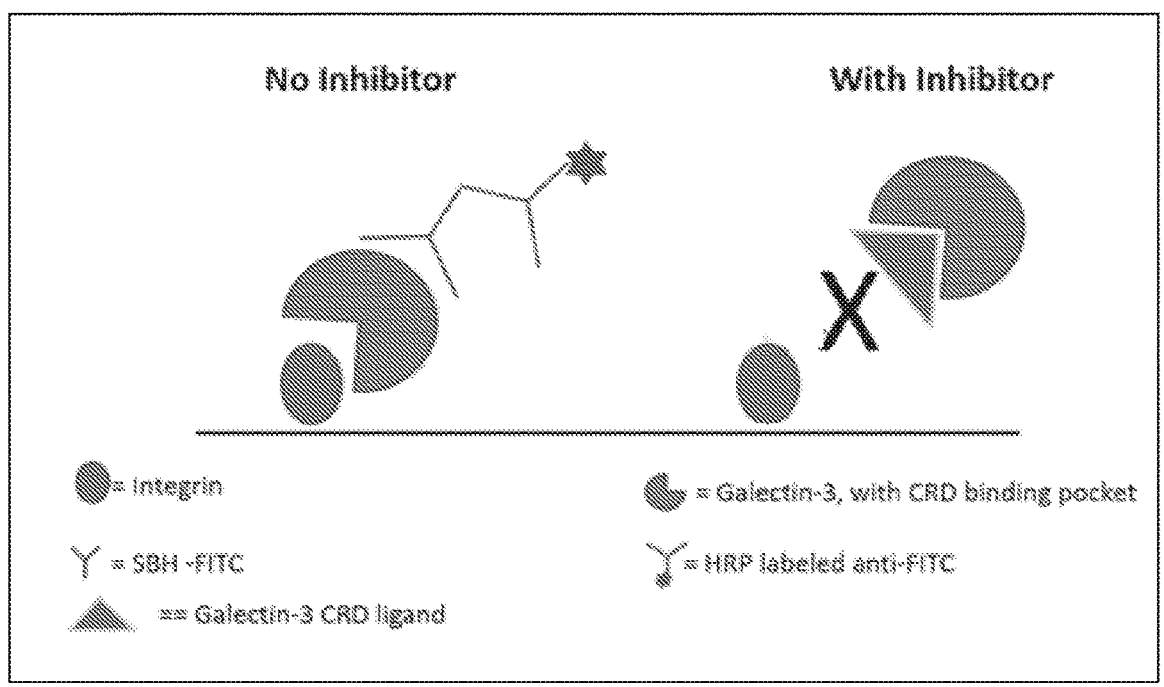
FIG. 7B illustrates a sandwich ELISA method using a functional ligand of Gal-3 with a specific antibody to Gal-3 to measure inhibition of ligand-target interaction according to embodiments of the invention.

Illustrations of functional assays with Gal-3 binding pairing specific antibody with a Glycoprotein ligand, e.g. Gal-3 Binding-Protein (Gal-3 BP), Integrins, etc. (FIGS. 7A and 7B).

Figure 8D:
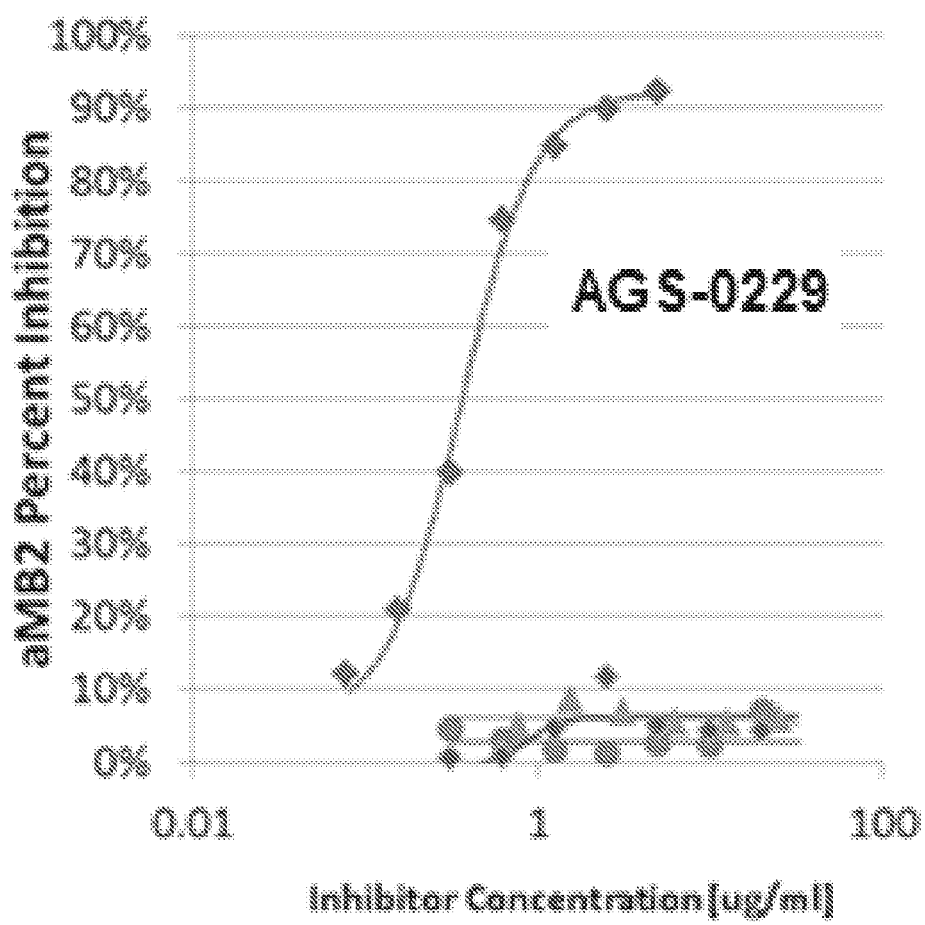
FIGS. 8D and 8E depict the specificity of AGS-0229, an allosteric inhibitor to Gal-3, as compare to the galactose derivatized compound according to embodiments of the invention. The ELISA assay (FIG. 8D, left) of Gal-3 (blue diamond) interaction with Integrin αMβ2 clearly demonstrate the specificity of AGS-0028 to Gal-3 while the galactose derivative TD-139 inhibit interaction of diversified galectins in addition to Gal-3 (galectins 1 (triangle), 8 (circle), and 9 (red diamond)) with integrin αMβ2 (FIG. 8E).

Using this assay, the compounds described herein inhibit the interaction of Gal-3 proteins with their ligands, including but not limited to various integrin molecules (αVβ3, αVβ6, αMβ2, α2β3, and others) with IC50's in the range of 50 ηM to 20 μM (FIGS. 8A, 8B and 8D). In some embodiments, compounds described herein have an IC50 of between 5 nM and 10 nM, from 5 nM and 100 nM, from 5 nM to 1 μM, from 5 nM to 10 μM, from 10 nM to 100 nM, from 10 nM to 1 μM, from 10 nM to 10 μM, from 10 nM to 20 μM, from 100 nM to 1 μM, from 100 nM to 10 μM, from 100 nM to 20 μM, from 1 μM to 10 μM, from 1 μM to 20 μM, from 10 μM to 20 μM, etc. . . . . .

Figure 8E:
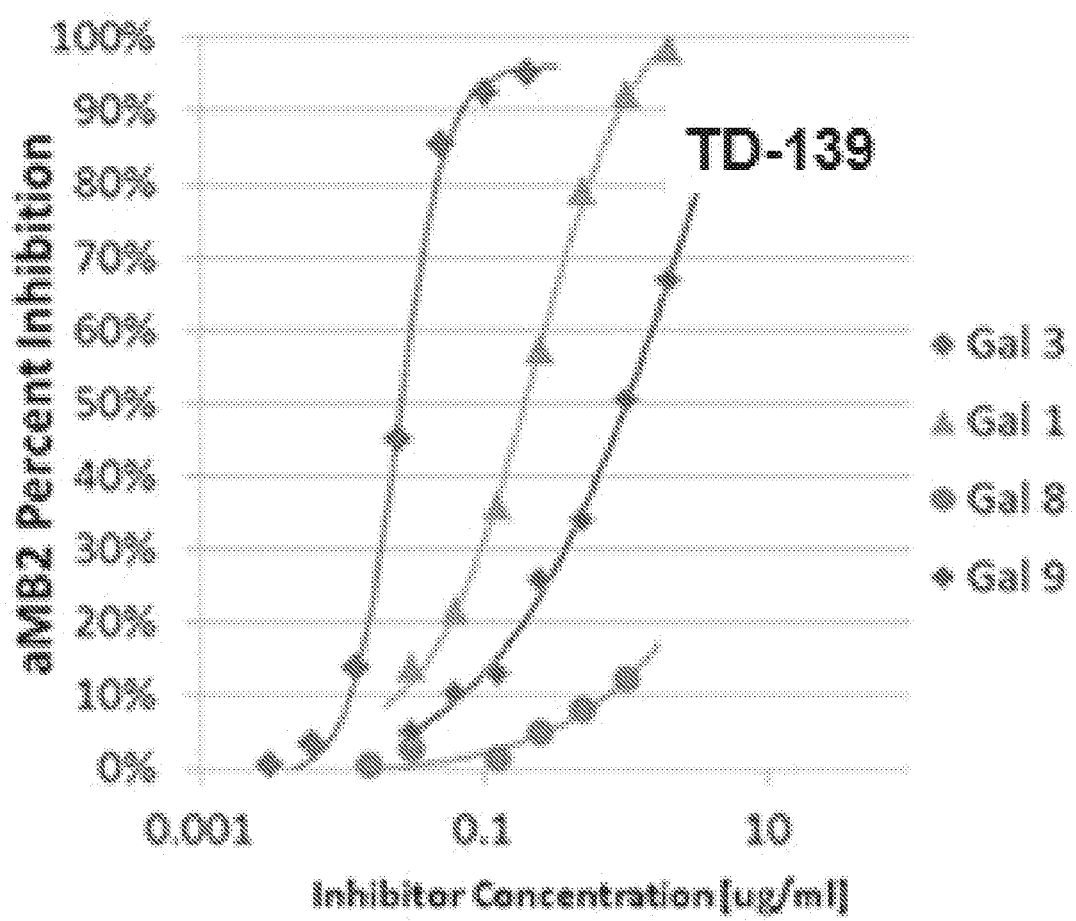

Functional Assays with Integrins: αMβ2 and αVβ6Integrin:

Activated ELISA plate is coated with αMβ2 integrin. Gal-3 binding is monitored with anti-Gal-3 antibody conjugated with FITC. Positive signal of FITC represent no inhibition while reduced signal indicate inhibition. FIG. 8A shows an example of a compound AGS-0028 that inhibits Gal-3 binding to various Integrins (αVβ6, αMβ2, α2β3) at about 1 μM. FIGS. 8D and 8E illustrate the specific Inhibition of Gal-3 by a compound described herein (AGS-0229) vs other galectins (FIG. 8D) versus the non-specific interaction of the digalactoside derivative TD-139 (FIGS. 8C and 8E).

Integrins with the of αv subunit as integrin αVβ6 were identified as playing important role in the molecular pathway that regulates fibrosis in several organs [Henderson et al. Nature Medicine, Vol. 19 (12) December 2013].

Integrin αVβ6 has been considered important in fibrosis and its important was validated when genetic deletion of the αV subunit had protected mice from carbon tetrachloride-induced hepatic fibrosis. Similar data was obtained with αVβ3 integrin that with Gal-3 have been reported to be involved in angiogenesis (https://www.rndsystems.com/resources/articles/role-Gal-3-angiogenesis).

The compounds described are highly specific to Gal-3 with $IC_{50}$ range of 5 ηM to 20 μM. This is shown by an ELISA inhibition assay (FIG. 8D) where AGS-0028 shown to hinder significantly only the Gal-3 interaction with Integrin αMβ2. While same integrin αMβ2 interaction with multiple galectins (1, 8, & 9) is inhibited with a CRD specific inhibitor, the galactose derivative TD-139 (FIG. 8E).

The allosteric compounds described herein could attenuate the CRD binding coefficient to either reduced its specificity to galactose ligands or may even increase its specificity to specific galactose ligand. These effects have been demonstrated for compounds AGS-0028 and AGS-0905.

Figure 11:
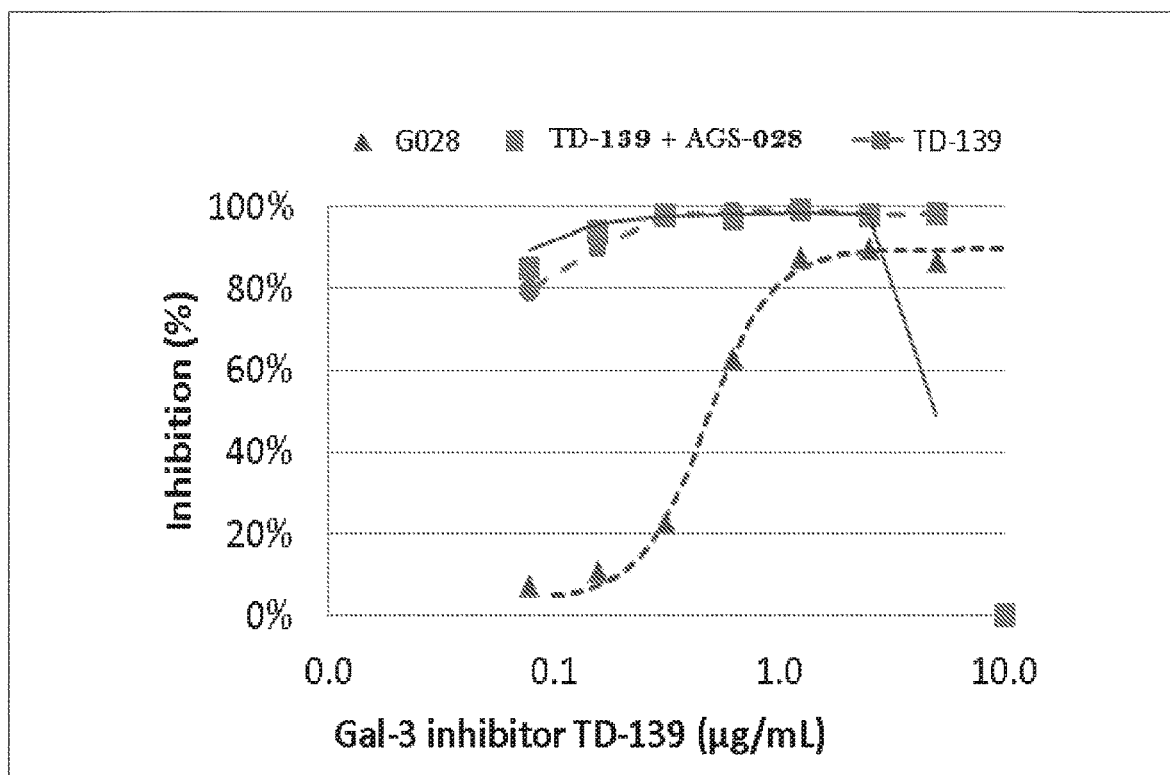
FIG. 11A shows a synergistic inhibition effect of compound AGS-0028 with the galactoside derivative TD-139. Thus AGS-0028 attenuates the CRD 3D structure in a way that inhibits the binding of Gal-3 with Gal-3 BP but does not affect the binding of TD-139 to the CRD. AGS-0028 attenuates negatively (inhibiting the binding of galectin-3 with Gal-3 BP) and it is synergistic with the TD-139 inhibition of this interaction of Galectin-3 and Galectin-3 BP.
FIG. 11B shows that compound AGS-0905 attenuates the CRD 3D structure which positively increase the CRD affinity and enhances the binding coefficient of Gal-3 with Gal-3 BP. Thus, AGS-0905 effect on the CRD was antagonistic to the TD-139 and effectively decrease its inhibition on the interaction between Gal-3 and its ligand Gal-3 PB according to embodiments of the invention.
Figure 11:
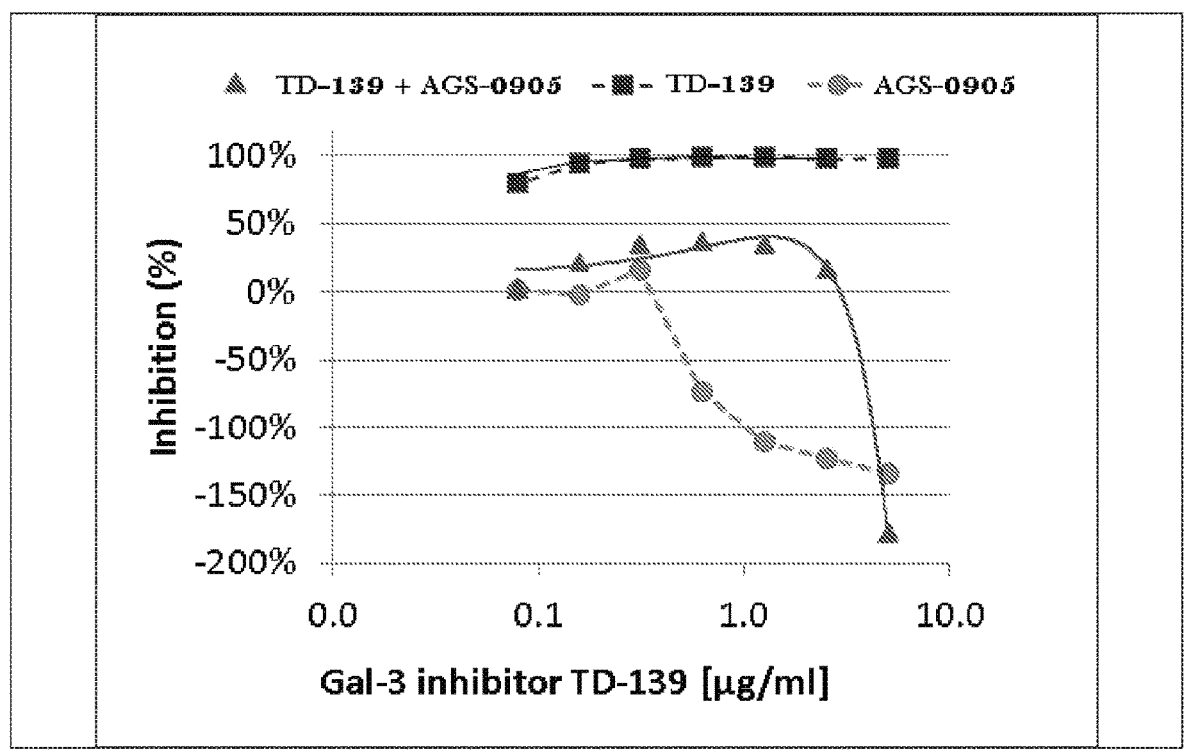

Compound AGS-0028 as depicted in FIG. 11A attenuates (inhibits) the binding of Gal-3 with Gal-3 BP and as such it is synergistic with the TD-139 binding and its inhibition of this interaction.

Compound AGS-0905 as depicted in FIG. 11B attenuates positively (enhancing) the binding coefficient of Gal-3 with Gal-3 BP and it thus decreased the TD-139 inhibition of this interaction.

Figure 12A:
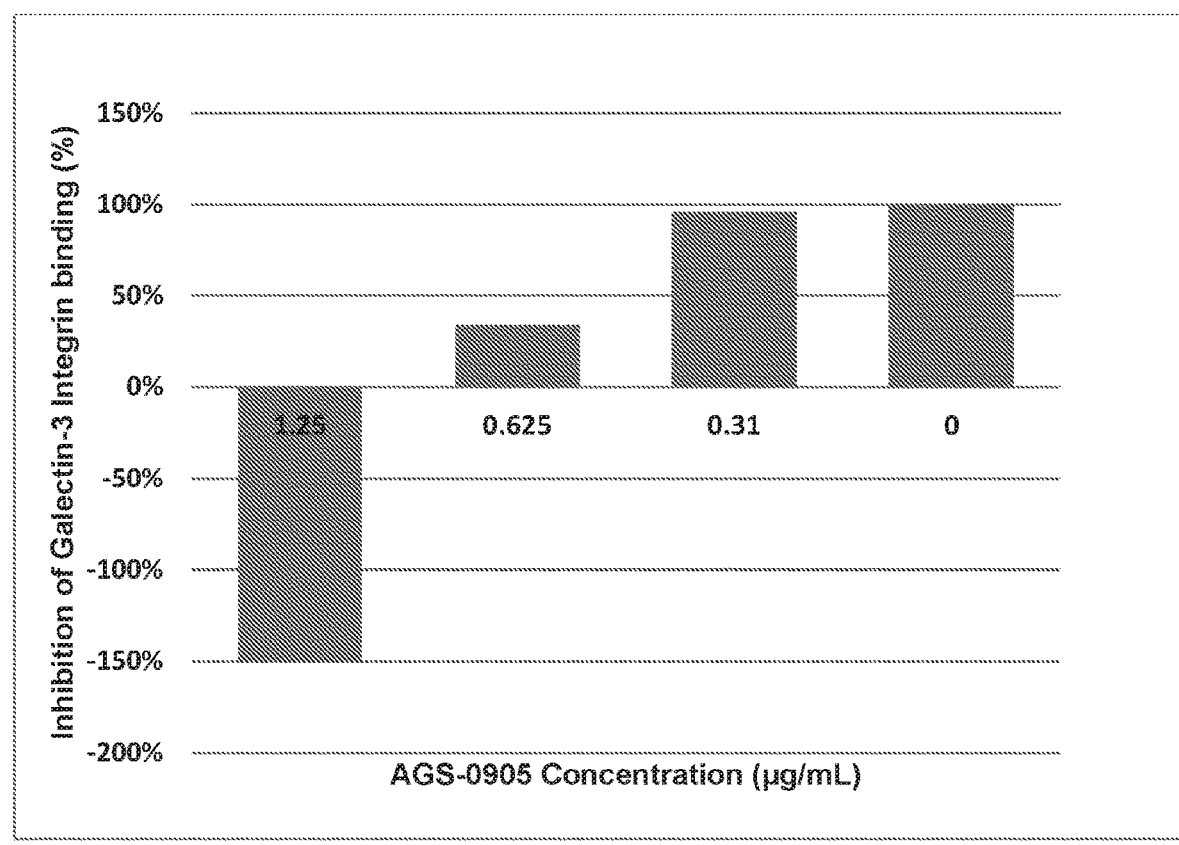
FIG. 12A shows that AGS-0905 enhanced the Gal-3 binding to Integrin αVβ6 and effectively decreases the inhibitory effect of TD-139 in dose response mode according to embodiments of the invention. AGS-0905 decreased the binding of TD-139 to Galectin-3 in dose response mode as denoted by reversal of its inhibition of the Galectin-3 binding to Integrin αVβ6.

Compound AGS-0905 as depicted in FIG. 12A decreased the binding of TD-139 to Gal-3 in dose response mode, as denoted by reversal of its inhibition of the Gal-3 binding to Integrin αVβ6.

Figures 1, 12B:
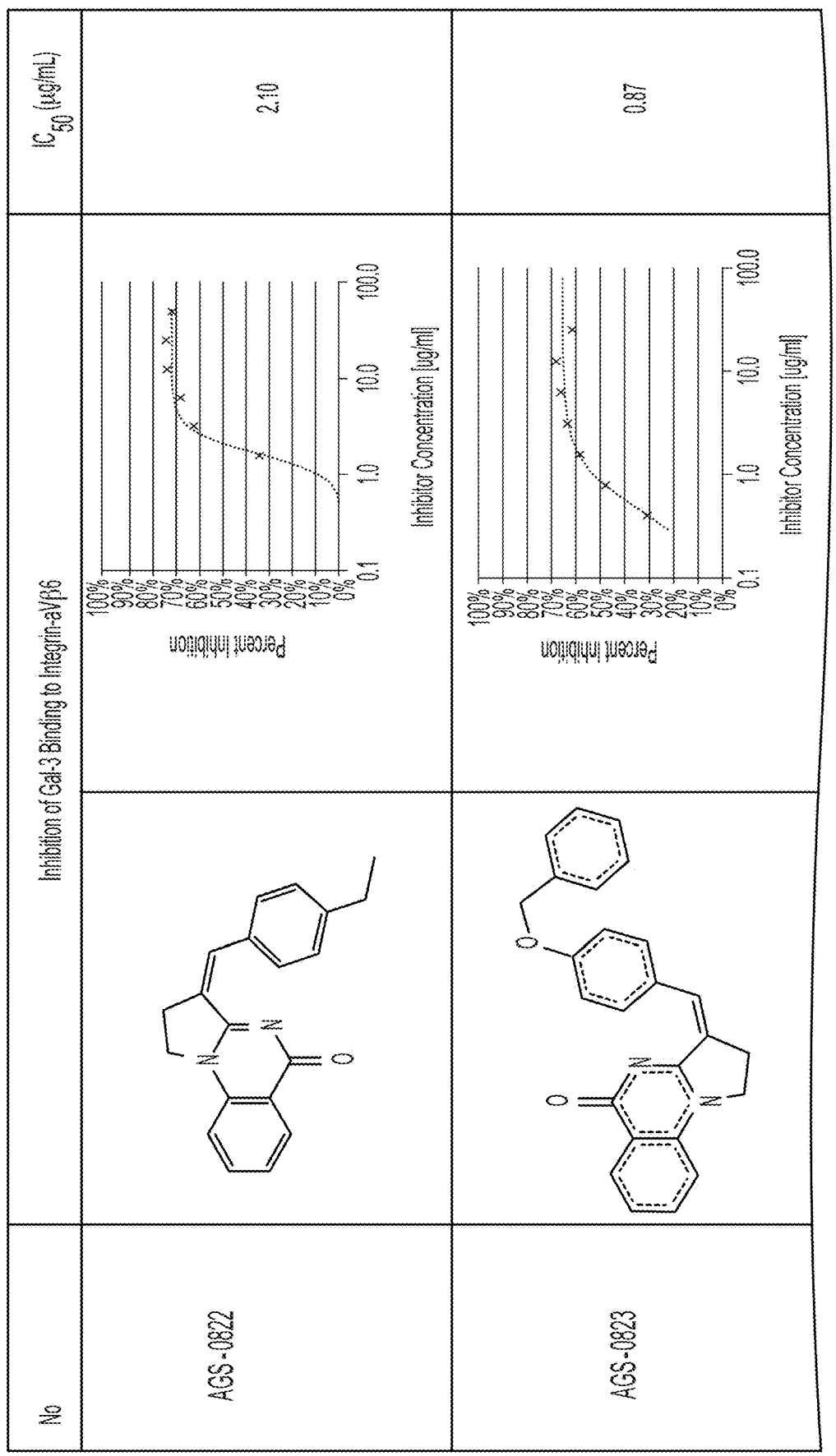
FIG. 12B depicts the inhibition of Gal-3 binding to integrin αVβ6 at low μM levels for several compounds with Formulas I and II according to embodiments of the invention.
Figures 2, 12B:
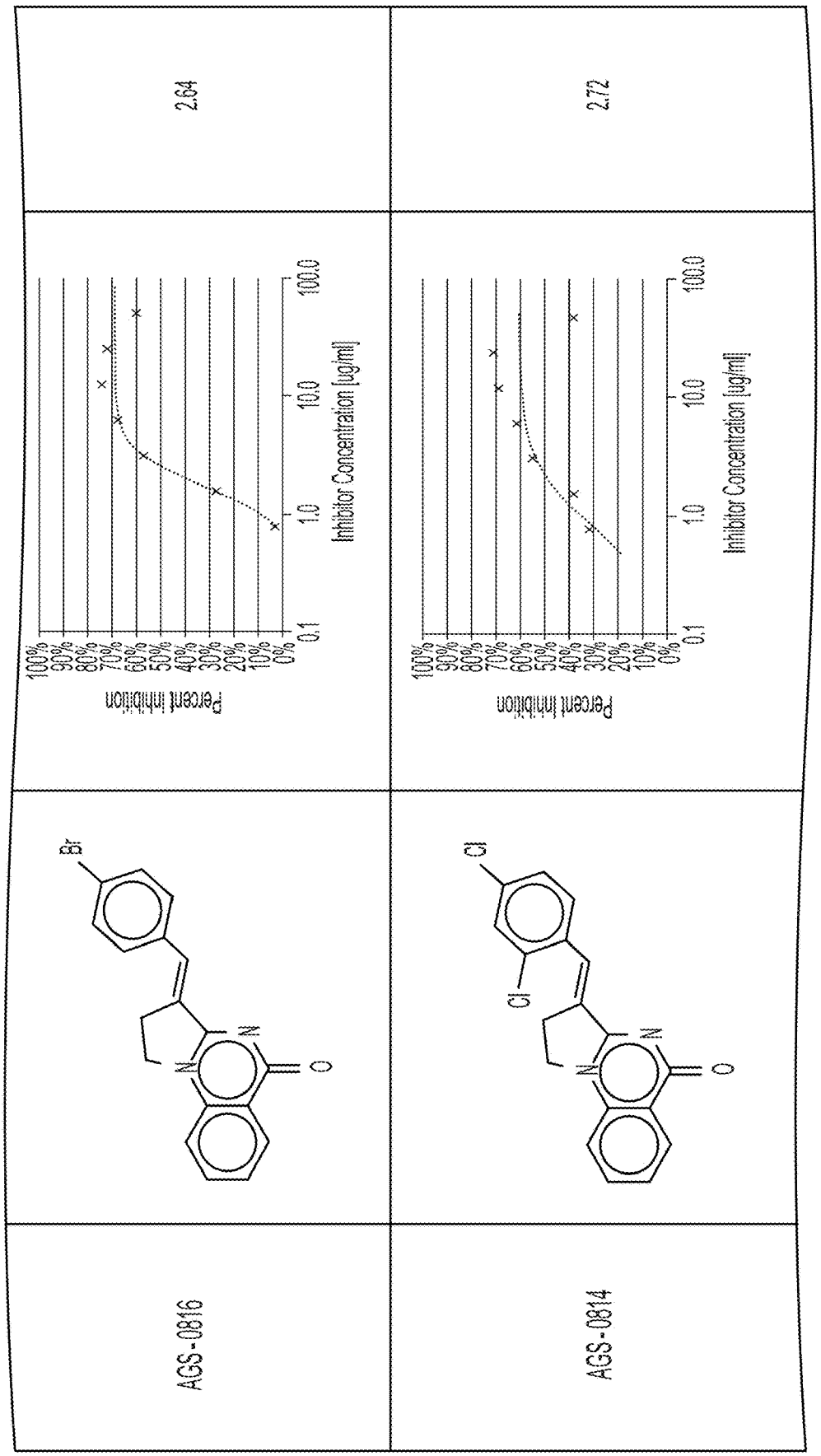
Figures 3, 12B:
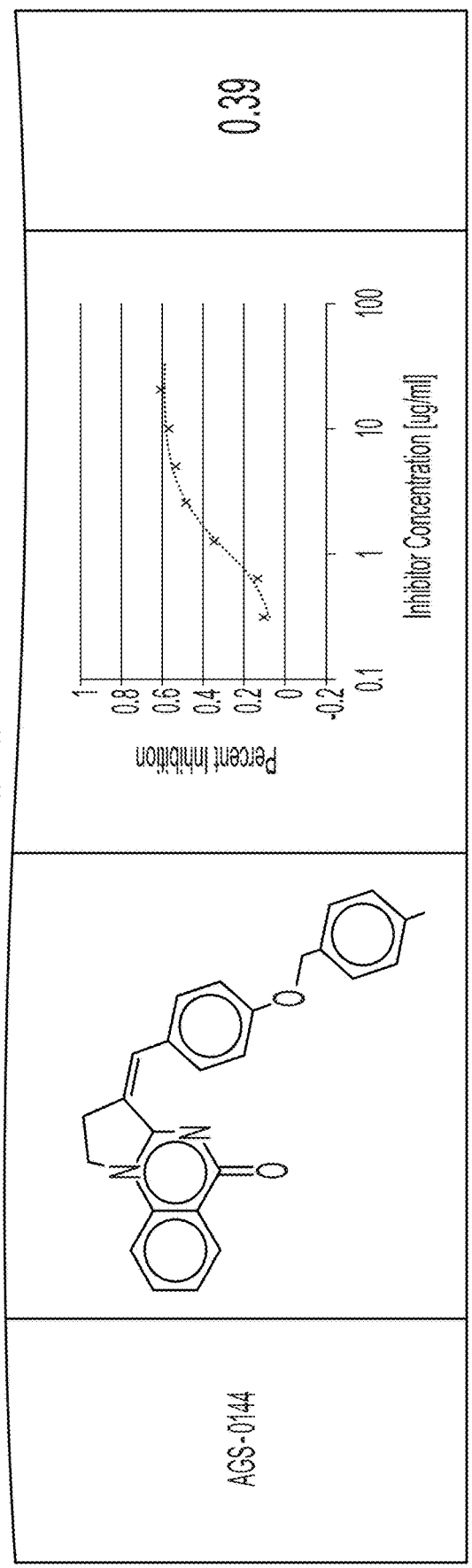
Figures 4, 12B:
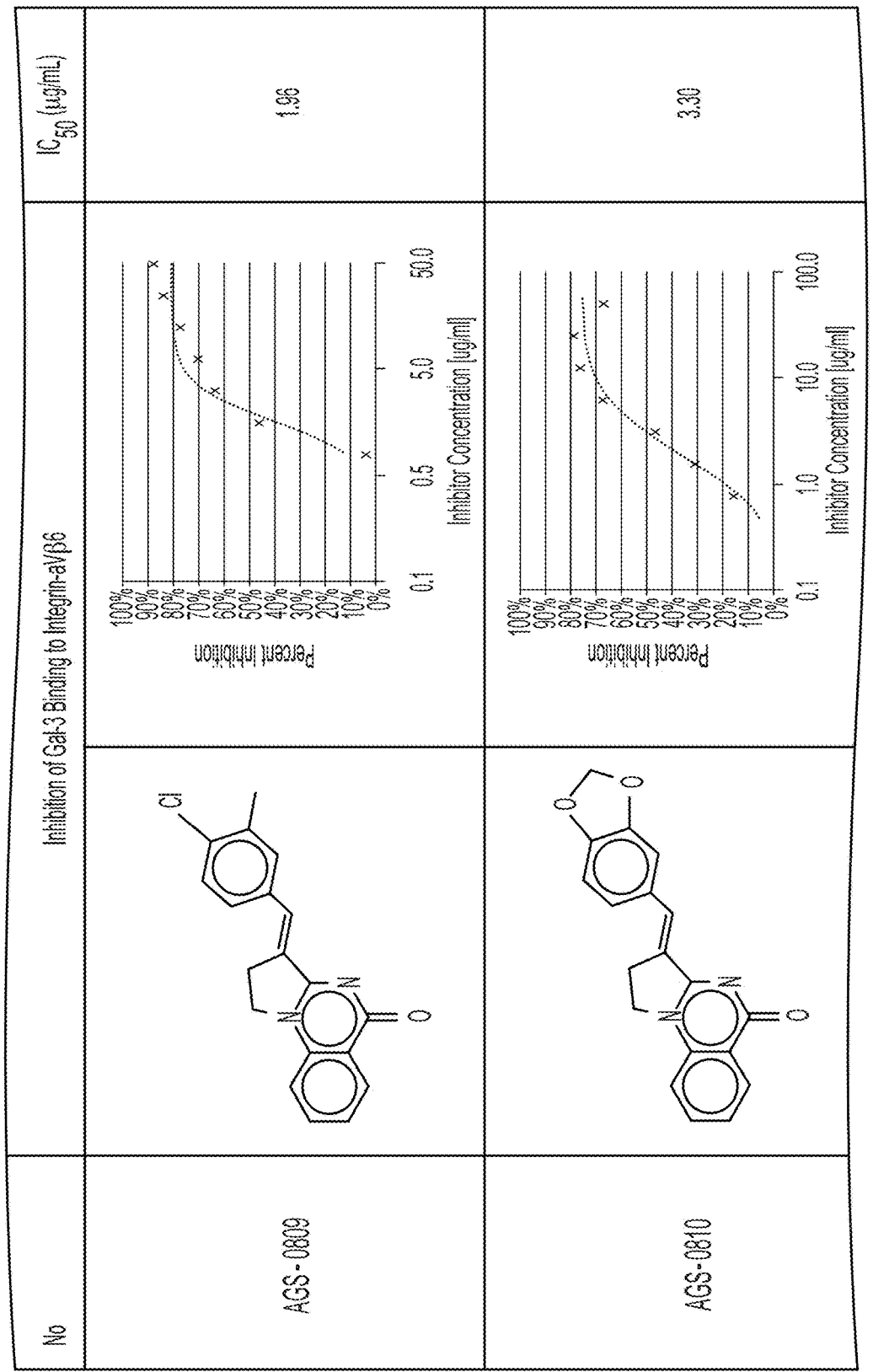
Figures 5, 12B:
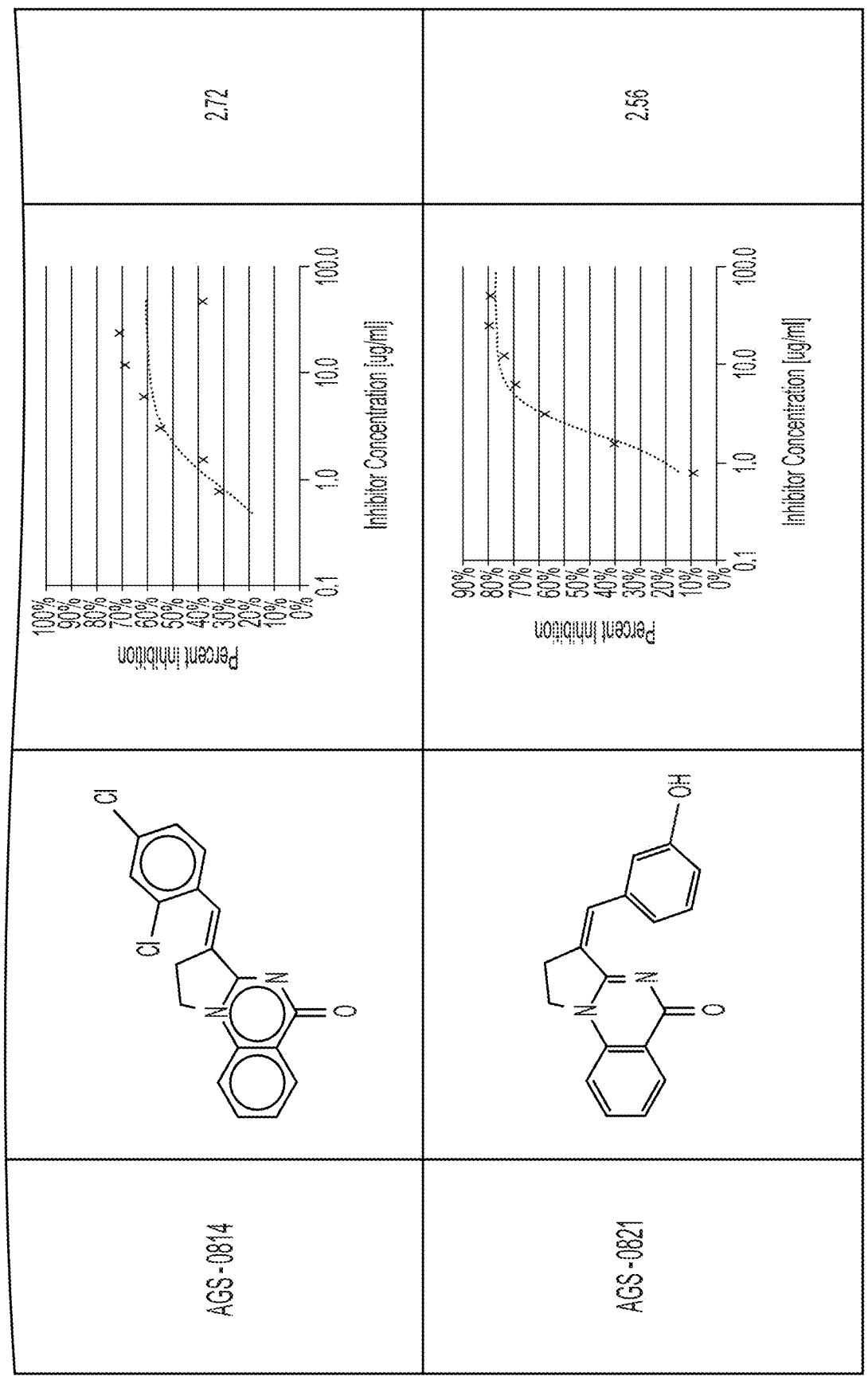

Further demonstration of the inhibition of Gal-3 binding to integrin αVβ6 is presented in FIG. 12B for several compounds with Formulas I and II.

Figure 12C:
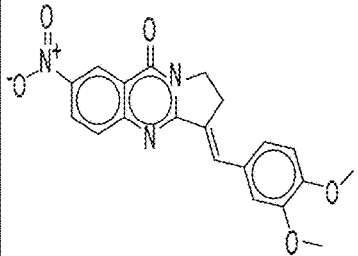
FIG. 12C depicts the inhibition of Gal-3 binding to integrin αMβ2 at low μM levels for several compounds with Formulas III and IV according to embodiments of the invention.
Figure 12C:
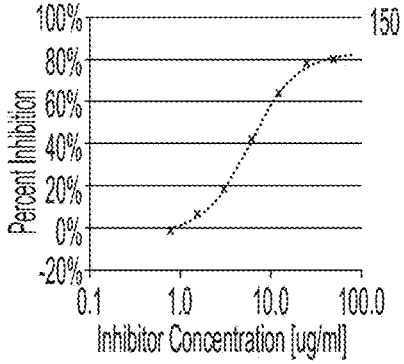
Figure 12C:
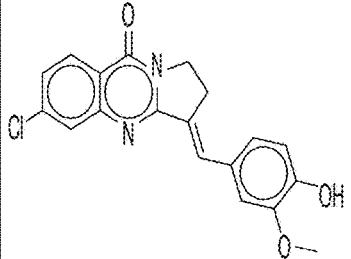
Figure 12C:
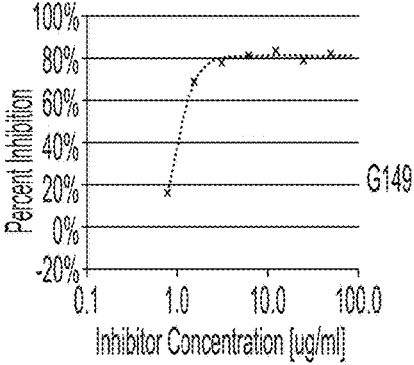
Figure 12C:
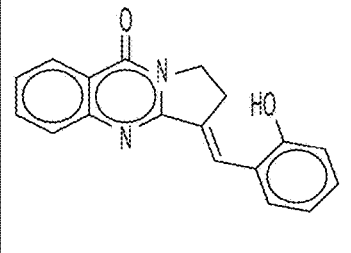
Figure 12C:
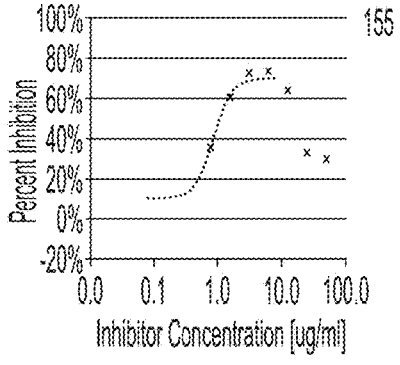
Figure 12C:
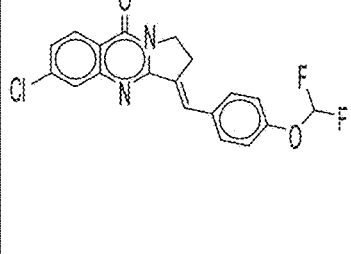
Figure 12C:
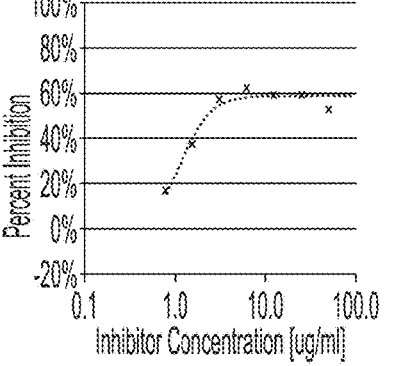

The inhibition of Gal-3 binding to integrin αMβ2 is demonstrated in FIG. 12C for several compounds with Formulas I, II and III.

Figure 12D:
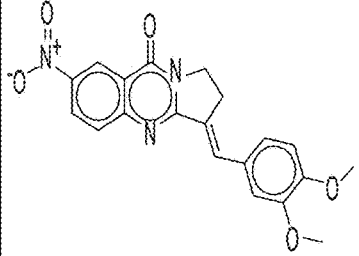
FIG. 12D depicts the inhibition of Gal-3 binding to Gal-3 Binding Protein at low μM levels for several compounds with Formulas III and IV according to embodiments of the invention.
Figure 12D:
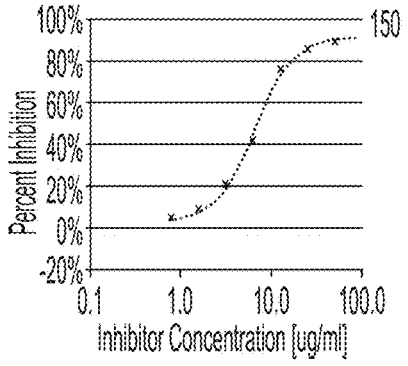
Figure 12D:
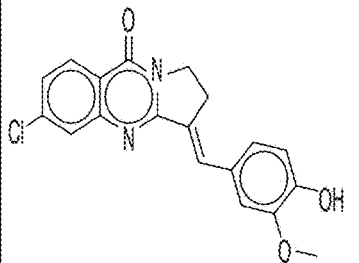
Figure 12D:
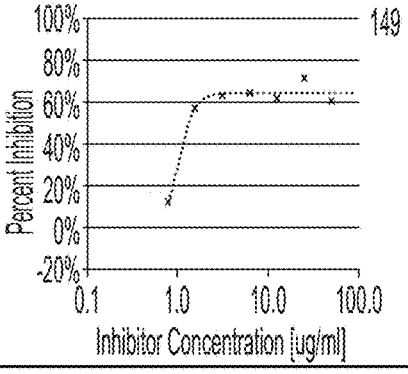
Figure 12D:
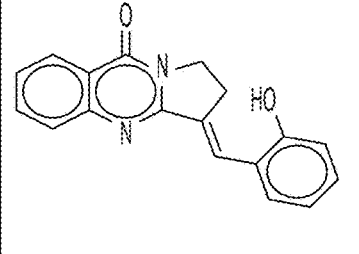
Figure 12D:
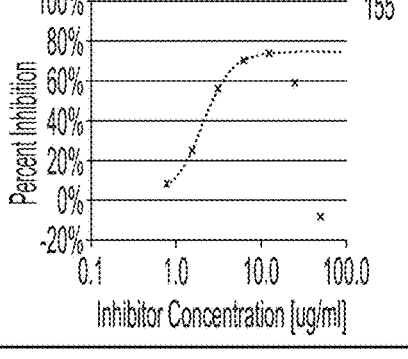
Figure 12D:
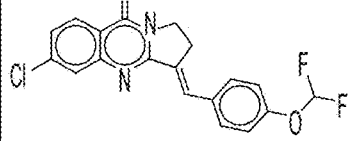
Figure 12D:
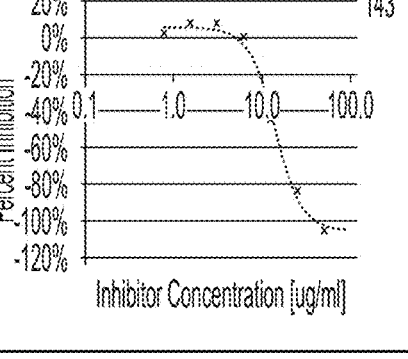

The inhibition of Gal-3 binding to the Gal-3 Binding protein is demonstrated in FIG. 12D for several compounds with Formulas I, II and III.

Figure 12E:
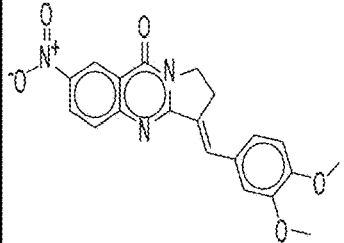
FIG. 12E shows inhibition of Gal-3 binding to TGF-beta Receptor type-1 (Gene: TGFBR1) at low μM levels for compounds of this invention with Formula III according to embodiments of the invention.
Figure 12E:
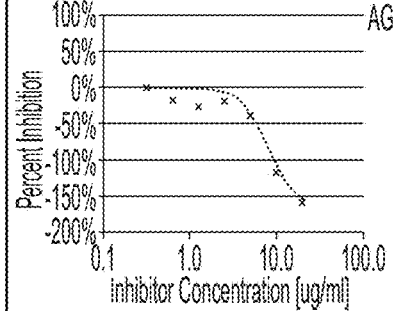
Figure 12E:
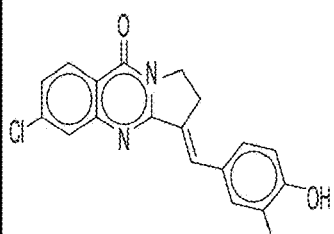
Figure 12E:
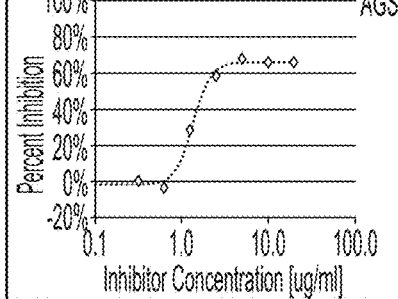
Figure 12E:
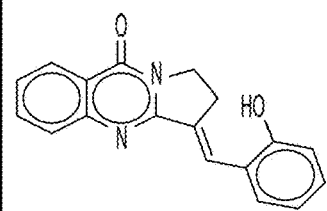
Figure 12E:
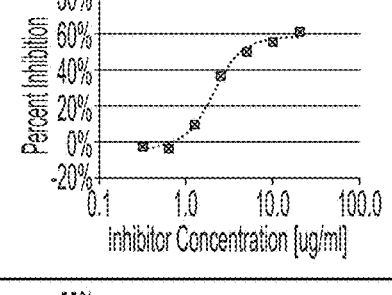
Figure 12E:
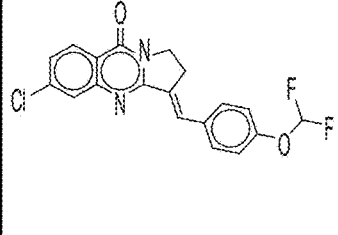
Figure 12E:
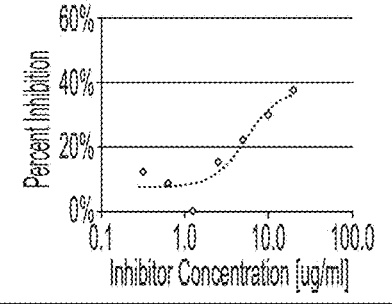
Figure 12E:
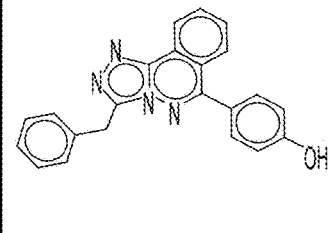
Figure 12E:
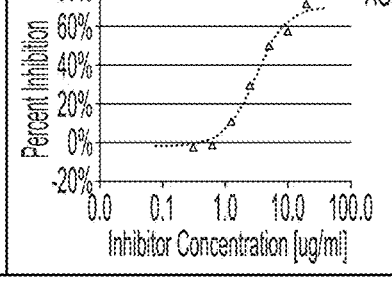
Figure 12E:
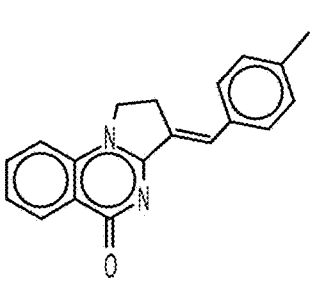
Figure 12E:
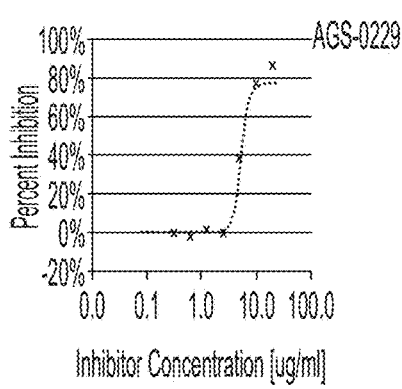
Figure 12E:
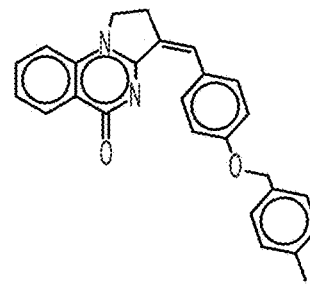
Figure 12E:
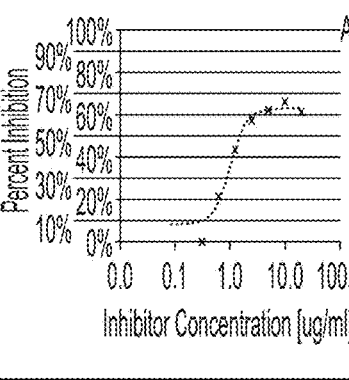

The inhibition of Gal-3 binding to TGFb1-Receptor is demonstrated in FIG. 12E for several compounds with Formulas I, II and III.

Figure 12F:
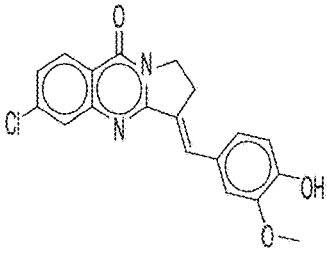
FIG. 12F depicts the inhibition of Gal-3 binding to Insulin Receptor (gene: INSR) at low μM levels for compounds with Formulas III and IV according to embodiments of the invention.
Figure 12F:
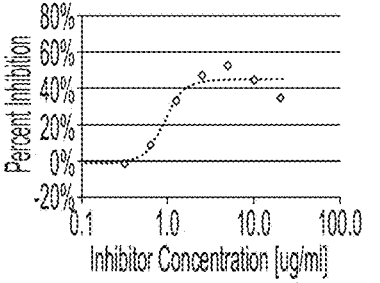
Figure 12F:
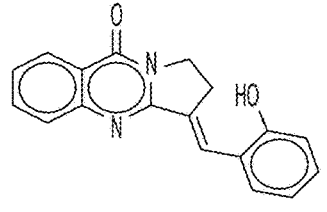
Figure 12F:
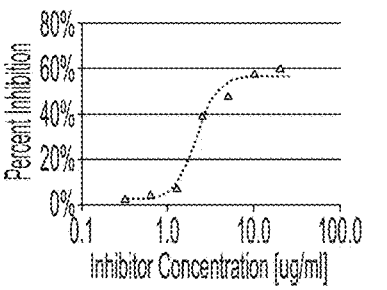
Figure 12F:
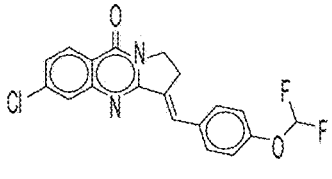
Figure 12F:
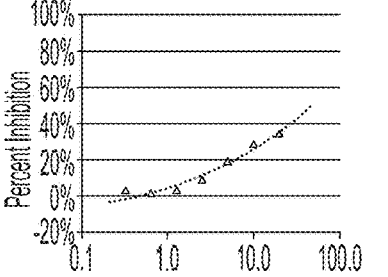
Figure 12F:
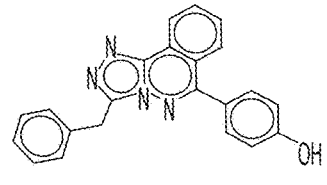
Figure 12F:
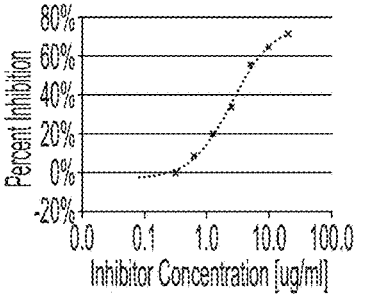
Figure 12F:
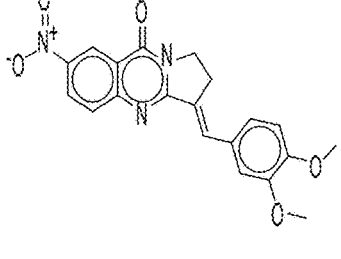
Figure 12F:
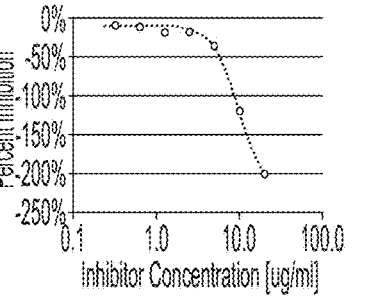

The inhibition of Gal-3 binding to Insulin Receptor (IR) is demonstrated in FIG. 12F for several compounds with Formulas I, II and III.

Example 4: Compound Binding to CRD and Other Epitopes as Analyzed by Amino Acid Residues Shifts by $^{15}$N NMR Heteronuclear $^{15}$N NMR spectroscopy was used to evaluate the interaction of compounds described herein with galectin molecules, including but not limited to Gal-3, to assess the interaction residues on the Gal-3 molecule.

Uniformly $^{15}$N-labeled Gal-3 was expressed in BL21 (DE3) competent cells (Novagen), grown in minimal media, purified over a lactose affinity column, and fractionated on a gel filtration column, as described previously for production of Galectin-1 [Nesmelova IV, et al. 2008, "1H, 13C, and 15N backbone and side-chain chemical shift assignments for the 29 kDa human galectin-1 protein dimer". Biomol NMR Assign 2008 December; 2 (2):203-205].

Uniformly $^{15}$N-labeled Gal-3 was dissolved at a concentration of 2 mg/ml in 20 mM potassium phosphate buffer at pH 7.0, made up using a 95% $H_2O$/5% $D_2O$ mixture. $^1H$-$^{15}N$ HSQC NMR experiments were used to investigate binding of a series of compounds described herein. $^1$H and $^{15}$N resonance assignments for recombinant human Gal-3 were previously reported [Ippel H, et al. 2015, "(1)H, (13)C, and (15)N backbone and side-chain chemical shift assignments for the 36 proline-containing, full length 29 kDa human chimera-type Gal-3". Biomol NMR Assign 2015; 9(1):59-63].

NMR experiments were carried out at 30° C. on Bruker 600 MHz, 700 MHz or 850 MHz spectrometers equipped with H/C/N triple-resonance probes and x/y/z triple-axis pulse field gradient units. A gradient sensitivity-enhanced version of two-dimensional $^1H$-$^{15}N$ HSQC was applied with 256 (t1)×2048 (t2) complex data points in nitrogen and proton dimensions, respectively. Raw data were converted and processed by using NMRPipe and were analyzed by using NMRview.

Figure 9A:
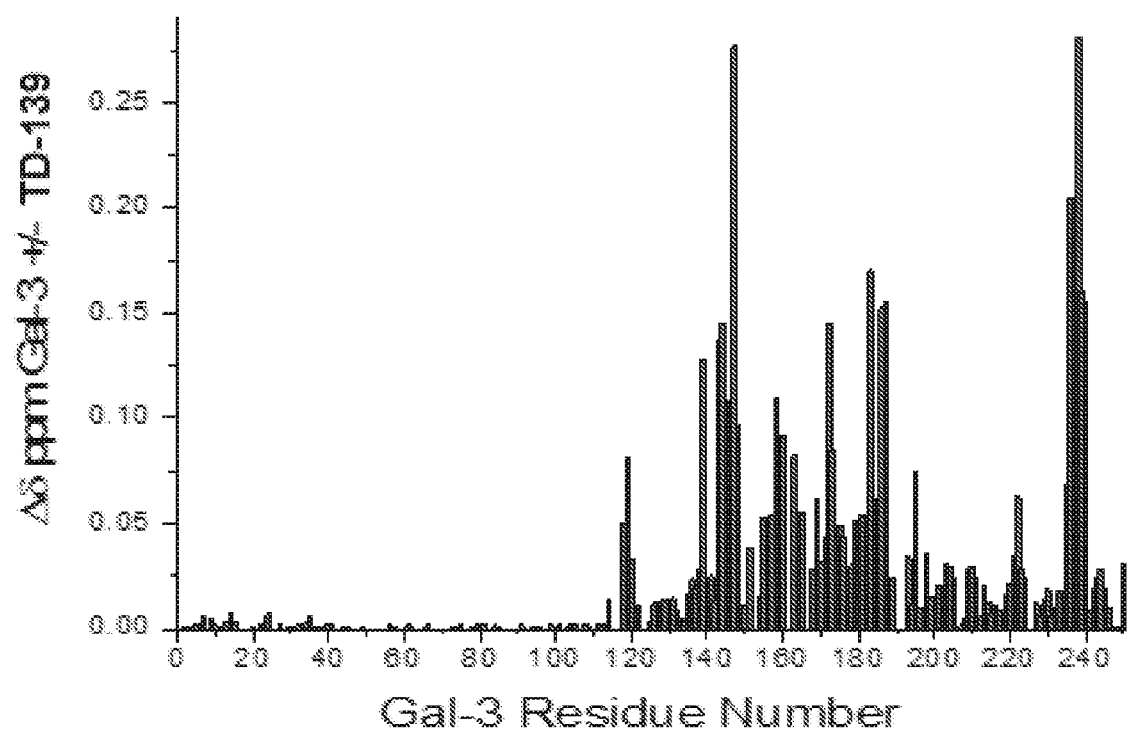
FIG. 9A shows $^{15}N$-NMR shifts of whole molecule of Gal-3 (Gal-3 FL) with the addition of the galactose derivatized compound TD-139 according to embodiments of the invention.
Figure 9B:
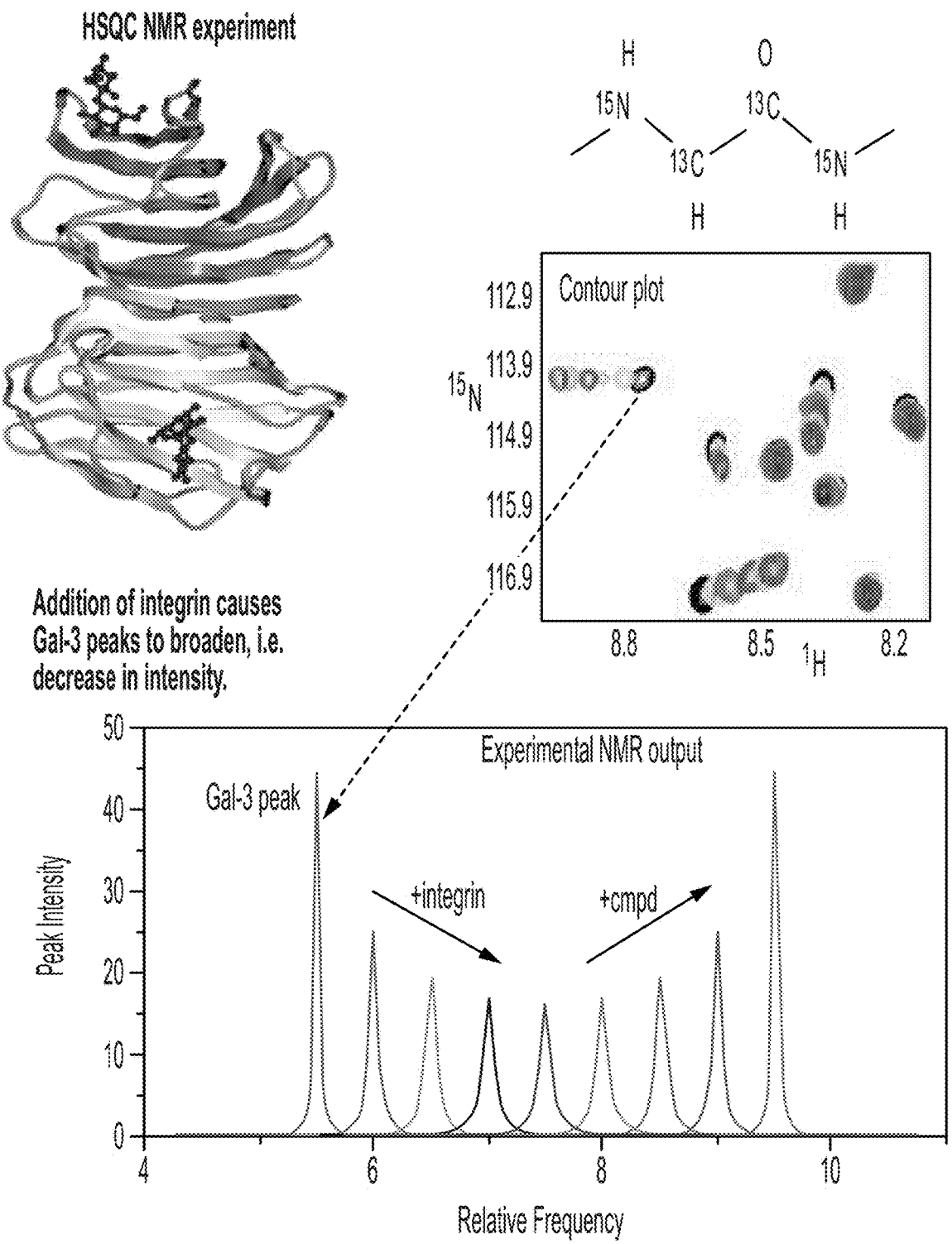
FIG. 9B shows the $^{15}N$-NMR shifts of Gal-3 amino-acids upon interaction with the functional glycoproteins like integrin showing shifts mostly of the CRD associated amino-acids similar to the shifts observed when Gal-3 interact with TD-139 according to embodiments of the invention. Galectin-3 interaction with the functional glycoproteins integrin effects the CRD associated amino-acids causing corresponding $^{15}N$-NMR shifts.
Figure 9C:
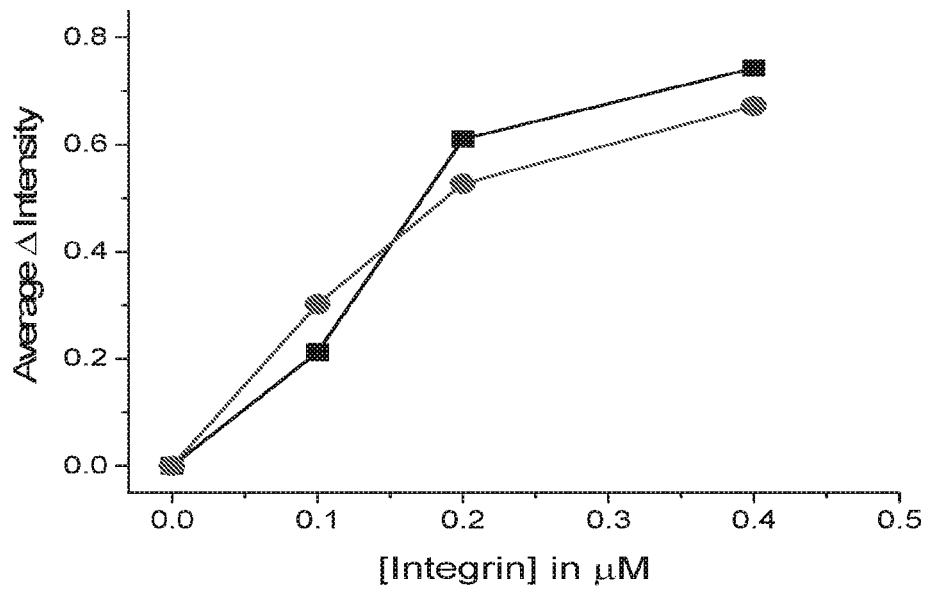
FIG. 9C shows a comparison of average Intensity changes that reflect Gal-3 binding avidity (affinity and stoichiometry) for integrin αMβ2 (red circles) and αVβ6 (black squares) according to embodiments of the invention.
Figure 9D:
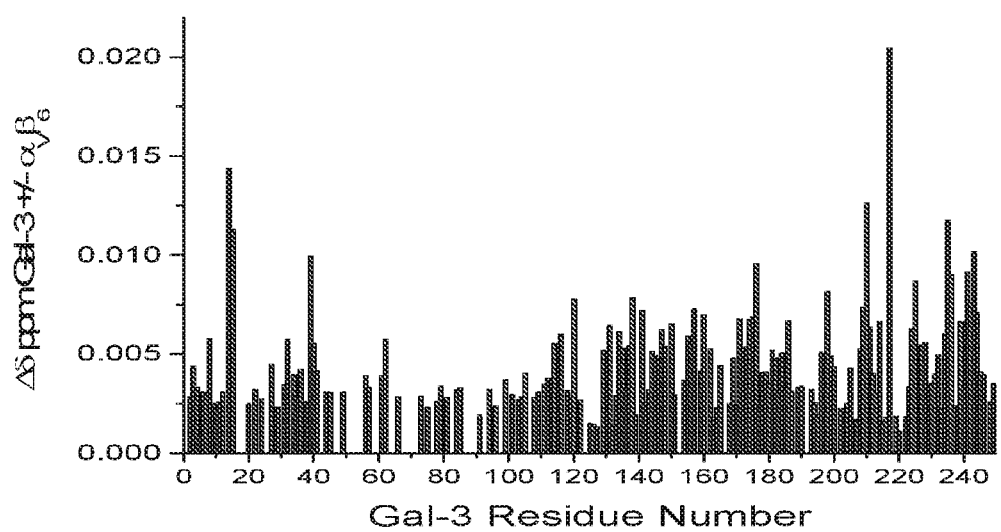
FIG. 9D shows $^{15}N$ NMR Intensity changes which reflect Gal-3 CRD binding avidity (affinity and stoichiometry) to integrin αVβ6 according to embodiments of the invention.

Using HSQC NMR experiment which investigate the shift of each individual amino-acids in the 3D structure of full Gal-3 the effect of the compounds described herein were clearly indicate an allosteric interaction. While galactose derivative like TD-139 clearly create disturbances of amino-acid located in the CRD site (FIG. 2B, FIG. 9A), the compounds described (AGS-0028, AGS-0144) have not directly interact with these amino-acids (FIGS. 2A, 3A, 3B, 3C, 9E, 9F). Investigation with functional glycoproteins like integrins the HSQC NMR has clearly indicated increases the intensity of amino-acids residues in Gal-3 associated with the CRD similar to lactose. However, other amino-acids also changed intensity (FIGS. 9C, 9D). Addition of the compounds described herein modified the intensity/signal which is translated to change in binding affinity (FIG. 9F).

From the NMR results (FIGS. 9B, 9C, 9D, 9E, 9F) it is obvious that integrins bind at the S-Face-CRD of Gal-3. However, the compound described herein obviously binds in a Non CRD location, either location close to the CRD on the S-face, or the F-Face or N-term (FIGS. 3A, 3B, 3C, 9B). However, as a result of their binding conformational changes in the 3D structure of Gal-3 affect the CRD pocket and as result they modified the Gal-3 protein interaction (FIGS. 9C and 9D).

Figure 9E:
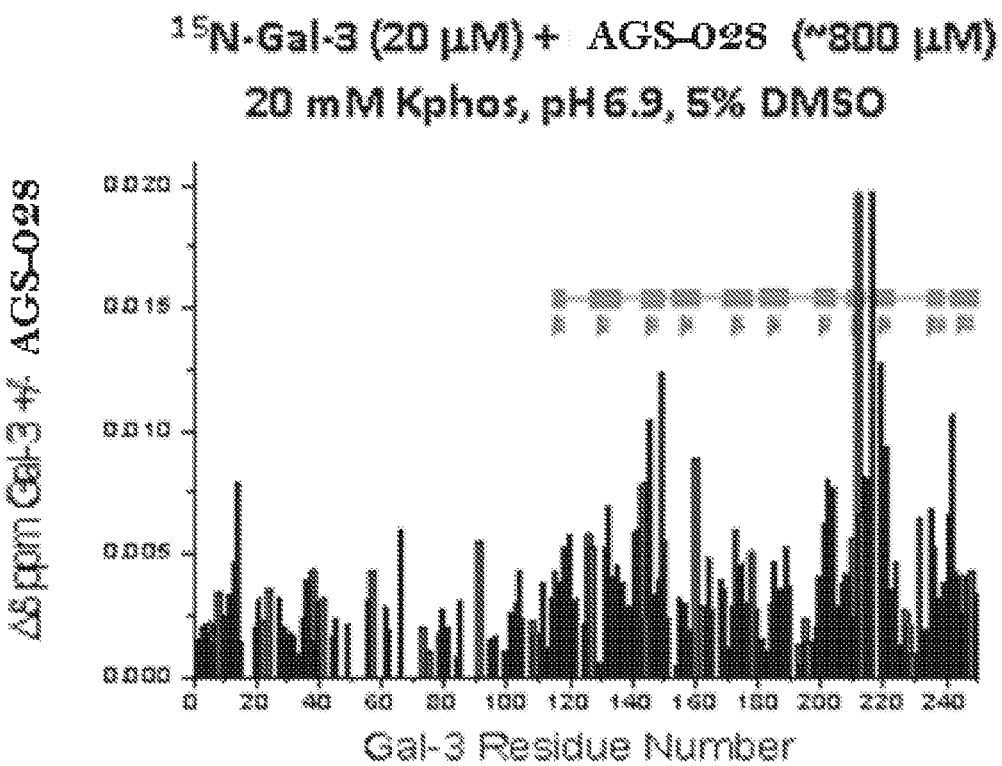
FIG. 9E depicts the effect of AGS-0028 on Gal-3 FL $^{15}N$ NMR Intensity upon interaction with integrin αVβ6 according to embodiments of the invention.
Figure 9E:
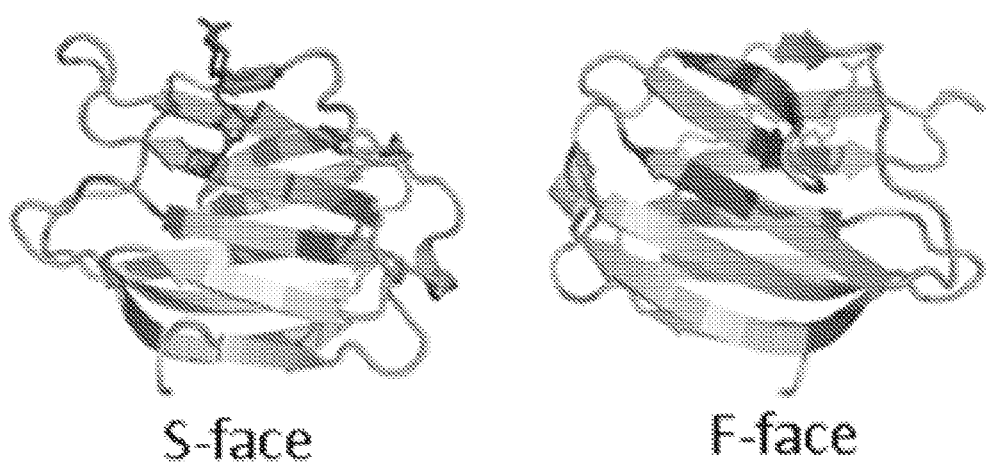
Figure 9F:
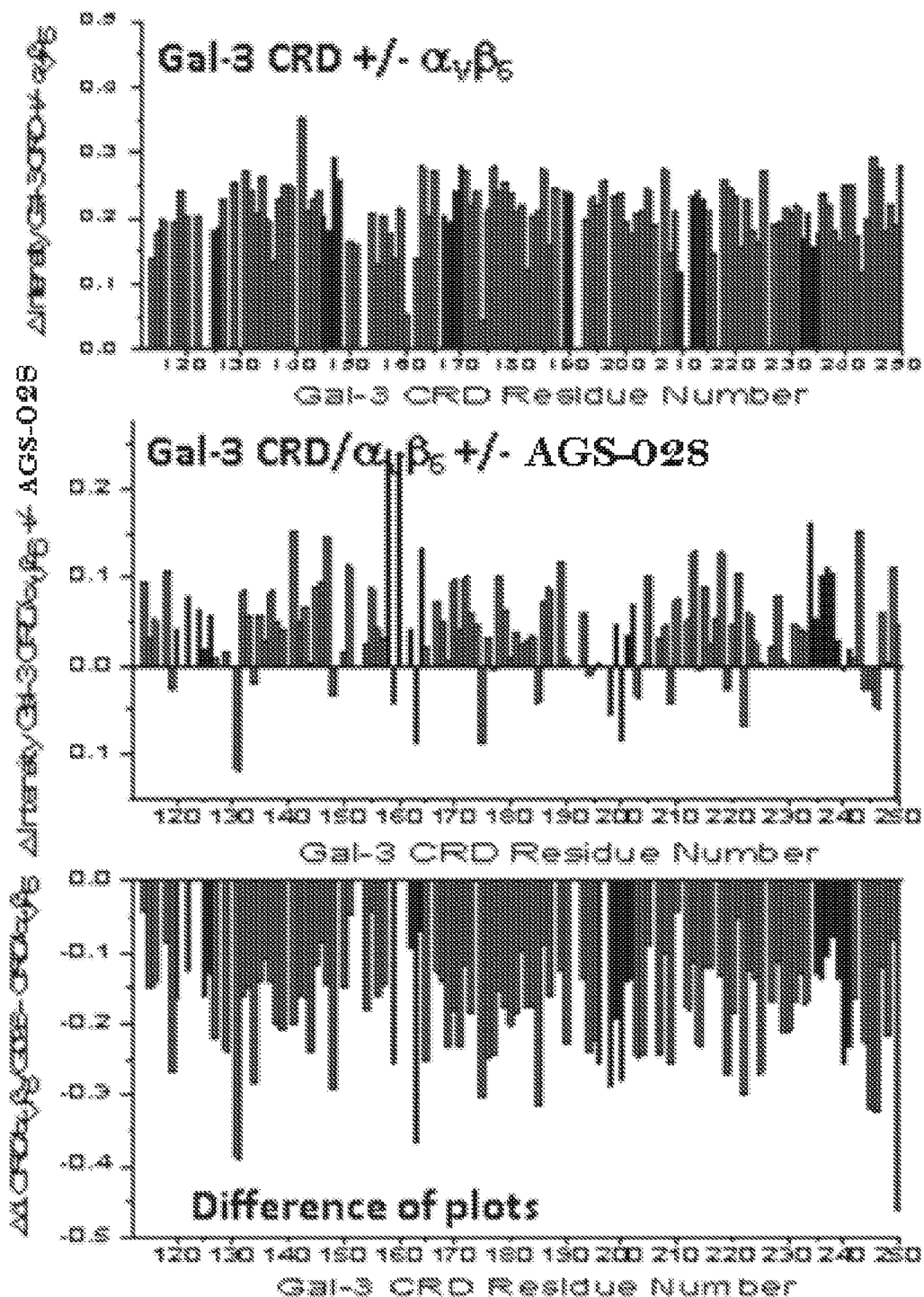
FIG. 9F depicts the Gal-3 CRD $^{15}N$ NMR shifts (AA 114-250) upon addition of AGS-0028 to the Gal-3 bound to integrin αVβ6. AGS-0028 attenuates binding of Gal-3 CRD to αVβ6

The NMR study of the interaction of the AGS-0028 with the Gal-3-integrin (aVb6) complex clearly demonstrate that the compounds attenuates multiple amino-acids of the Gal-3 including amino-acids at the Gal-3 CRD site (FIGS. 9E and 9F).

The compounds described herein may in some embodiments also enhance the affinity of a complex interaction of the Gal-3 with functional glycoproteins and made the interaction more specific as illustrated by compound AGS-0905 (FIG. 11B).

These HSQC NMR experiments clearly showed differences between compounds described herein and galactose derivatives described in prior art to bind exclusively to amino-acids residues in the carbohydrate binding domain of Gal-3.

Example 5: Cellular Activity of Cytokine Activity Related to Galectin Binding Inhibition Example 1 describes the ability of compounds described herein to inhibit the binding of physiologic ligands to galectin molecules. In the experiments of this example, the functional implications of those binding interactions were evaluated.

One of the interactions with Gal-3 that was inhibited by the compounds described herein was TGF-β receptor. Therefore, experiments were done to evaluate the effect of compounds on TGR-β receptor activity in cell lines. Various TGF-β responsive cell lines, including but not limited to LX-2 and THP-1 cells, was treated with TGF-β and response of the cells measured by looking at activation of second messenger systems, including but not limited to phosphorylation of various intracellular SMAD proteins. After establishing that TGF-β activated second messenger systems in the various cell lines, the cells were treated with compounds described herein. The findings showed that these compounds inhibited TGF-β signaling pathways, confirming that the binding interaction inhibition described in Example 1 has a physiological role in cellular models.

Cellular assays were also performed to evaluate the physiological significance of inhibiting the interaction of Gal-3 with various integrin molecules. Cell-cell interaction studies were performed using monocytes binding to vascular endothelial cells, as well as other cell lines. Treatment of cells with compounds described herein was found to inhibit these integrin-dependent interactions, confirming that the binding interaction inhibition described in Example 1 has a physiological role in cellular models.

Cellular motility assays were performed to evaluate the physiological significance of inhibiting the interaction of Gal-3 with various integrin and other cell surface molecules defined in Example 1. Cellular studies were performed using multiple cell lines in a semi-permeable membrane separated well apparatus. Treatment of cells with compounds described herein were found to inhibited cellular motility, confirming that the binding interaction inhibition described in Example 1 has a physiological role in cellular models.

Example 6: In-Vitro Inflammatory Model (a Monocyte Based Assay)

Figure 10:
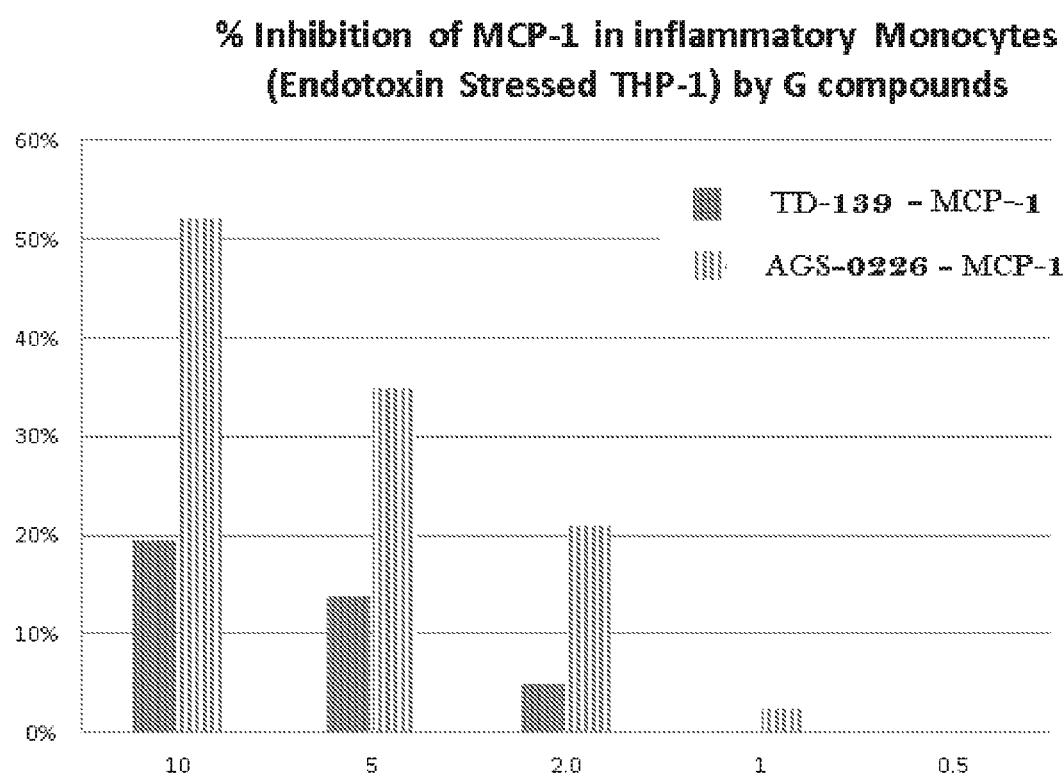
FIG. 10 depicts the effect of Gal-3 inhibitors on the secretion of h-MCP-1 by inflammatory stressed macrophages (endotoxin stressed THP-1 monocyte cells—inflammatory model) according to embodiments of the invention.

A model of macrophage polarization was set up, starting from THP-1 monocytes culture which was differentiated into inflammatory macrophages using PMA (Phorbol 12-myristate 13-acetate) for 2-4 days. Once differentiated (M0 macrophages), they were induced with LPS or LPS and IFN-gamma for macrophage activation (M1) to inflammatory stage for 1-3 days. Array of cytokines and chemokines were analyzed to confirm the polarization of THP-1-derived macrophages to inflammatory stage. The impact of the anti-galectin 3 compounds on macrophage polarization was assessed first by monitoring cell viability using a colorimetric method (using a tetrazolium reagent) to determine the number of viable cells in proliferation or cytotoxicity assays (Promega, The CellTiter 96® AQueous One Solution Cell Proliferation Assay which contains a novel tetrazolium compound [3-(4,5-dimethyl-2-yl)-5-(3-carboxymethoxyphenyl)-2-(4-sulfophenyl)-2H-tetrazolium, inner salt; MTS] and an electron coupling reagent (phenazine ethosulfate; PES)) and inflammatory stage evaluated by a quantitatively measure the chemokine Monocyte Chemoattractant Protein-1 (MCP-1/CCL2), a key protein that regulate migration and infiltration of monocytes/macrophages in cellular process of inflammation. Follow-up testing for the expression and secretion of other cytokines and chemokines were done for leading active compounds. Results were expressed in percentage reduction of MCP-1 (FIG. 10).

Compound's ability to reduce MCP1 expression in activated THP1 cells will reduce inflammatory macrophages activity [see <https://www.bio-rad-antibodies.com/macrophage-polarization-minireview.html]. Mass spec of HUVEC lysates isolated with a Gal-3 affinity column identified αVβ3 as a binding partner. αVβ3 has been reported to be involved in growth factor-mediated angiogenesis. Treating HUVECs with Gal-3 promoted αVβ3 clustering and focal adhesion kinase (FAK) activation. Antibodies against αVβ3 inhibited Gal-3-induced HUVEC migration and capillary tubule formation. [Markowska, A. I. et al. (2010) J. Exp. Med. 207:1981].

Example of Method Steps:
1) THP-1 cells where cultured in media containing Gentamicin
2) THP-1 cells were transfer to wells in a 96 well plate 2,000 cells/well for 2 days incubation in assay media containing 10 ng/ml PMA
3) Serial dilution of test compounds was made in LPS (10 ng/ml) containing media
4) To each well 100 ml of compounds/LPS solution was added to a final assay volume of each well of 200 ml contain also Gentamicin and 5 ng/ml PMA
5) Cells were incubated up to 8 days.
6) Every other day samples of 60 ul were removed for bio-assay
7) At termination 15 ml of Promega Substrate CellTiter 96 Aqueous One Solution was added to each well to monitor cytotoxicity (at 490 nm)
8) For cellular biomarkers evaluation the cells were washed 1×PBS and extracted with 200 ul of Lysis buffer for 1 hour. Extract was spinned down 10 minutes and 120 ul sample was removed from top. All samples were kept at −70 C until testing.

THP-1 cells were stimulated by microbial endotoxin which transforms the cells to inflammatory macrophages (M1) which secret inflammatory cytokines like Monocyte Chemoattractant Protein-1 (MCP-1). Anti-inflammatory agents reduce the expression of MCP-1 as was demonstrate for AGS-0229 (FIG. 10).

Example 7: Cell Culture Fibrogenesis Model

Experiments are performed with fibrogenic stellate cell cultures, including but not limited to LX-2 cells, to evaluate the cellular effect of compounds described herein. LX-2 cells are activated in culture using serum deprived media and media spiked with different percentages of THP-1 cell conditioned media. Activation of LX-2 cells is monitored by various well-defined markers, including but not limited to TIMP-1. Demonstrable LX-2 cell activation is evident by 24 hours after treatment and treatment of cells with compounds described herein are found to inhibit activation, confirming a physiological role in cellular models.

Example 8: In Vivo Animal NASH/Obesity Model of Liver Fibrosis

Nonalcoholic Steatohepatitis (NASH) Mouse Fibrosis Model

The NASH model uses male newborn mice [C57BL/6J mice]. The disease is induced by a single subcutaneous injection of streptozotocin (Sigma, St. Louis, Mo.) solution 2 days after birth which induced diabetes. After four weeks of age a high fat diet (HFD, 57% of kcal from fat) is introduced for 12 and up to 16 weeks. Vehicle and test substances at the various doses are administered orally or SQ or intravenously weekly and calculated as mg/kg body weight. Animal care follows protocols accordance with accepted Guidelines for Animal Use. Animals are fasted for 3 hours before sacrifice which is performed by exsanguination through direct cardiac puncture under ether anesthesia.

Randomization of mice into treatment groups is done prior to treatment based on the plasma ALT levels and body weight. At minimum 3 treatment groups are in a study.
Group 1: Twelve normal mice will be fed with a normal diet ad libitum without any treatment,
Group 2: Twelve NASH mice will be intravenously administered vehicle (0.9% sodium chloride) once weekly from 6 to 12 weeks of age
Group 3: Twelve NASH mice will be intravenously administered test article in vehicle (0.9% sodium chloride) once weekly from 6 to 12 weeks of age
Mice will be sacrificed for the following 4 weeks of treatment
Leading compounds will reduce live fibrosis as measure by collagen 10 to 80% versus the vehicle control or to almost normal collagen levels as established in group 1.
General Biochemical Tests:

Diabetic fast glucose is measured in whole blood samples using for example G Checker (Sanko Junyaku Co. Ltd., Japan).

Liver functions are evaluated in Plasma for levels of AST, ALT, total bilirubin, creatinine, and TG are measured by example FUJI DRY CHEM 7000 (Fuji Film, Japan).

Liver biochemistry: To quantify liver hydroxyproline content, a quantitative assessment of collagen content, frozen liver samples (40-70 mg) are processed by a standard alkaline-acid hydrolysis method and hydroxyproline content is normalized to total liver proteins.

Total liver lipid-extracts are obtained from caudate lobes by Folch's method and liver TG levels are measured using the Triglyceride E-test (Wako, Japan).

Histopathological and immunohistochemical analyses liver sections are cut from paraffin blocks of liver tissue prefixed in Bouin's solution and stained with Lillie-Mayer's Hematoxylin (Muto Pure Chemicals, Japan) and eosin solution (Wako, Japan).

To visualize collagen deposition, Bouin's fixed liver sections are stained using picro-Sirius red solution (Waldeck GmbH & Co. KG, Germany). NAFLD Activity score (NAS) is also calculated according to established criteria.

Immunohistochemistry for SMA, F4/80, Gal-3, CD36 and iNOS can be estimated from each positive area as indication of the extent of inflammation and fibrosis.

Example 9: In-Vivo Animal Chemical Toxicity Leading to Fibrosis/Cirrhosis Model

Rat Thioacetamide (TAA) Treated Liver Fibrosis Model:
These experiments use male Sprague-Dawley rats between 160 and 280 g obtained from animal research facility (Jackson Laboratory) and maintained according to the Guide for the Care and Use of Laboratory Animals (Institute of Laboratory Animal Resources, 1996, Nat. Acad. Press) and Institutional Animal Care and Use committee (IACUC). At the end of experiments, animals are euthanized under phenobarbital anesthesia.

After an acclimation period of two weeks, an eight-week induction period is initiated, in which all rats are subjected to intraperitoneal (IP) injections Thioacetamide (TAA, Sigma Chemical Co., St. Louis, Mo., USA) of sterile solutions of dissolved in 0.9% saline, administered by IP injection twice or trice weekly with initial week dosage of 450 mg/kg/wk, followed by seven weeks regimen of 400 mg/kg/wk body weight. To assess for the progression of fibrosis two rats are euthanized at weeks 4 and 8, and the liver examined histologically. To develop cirrhosis animals are administered TAA IP up to 11-12 weeks, for fibrosis 8 weeks are enough.

Treatment was for 4 weeks beginning in week 8, vehicle control group ia administered 0.9% NaCl intraperitoneally (IP) twice weekly for four weeks. Experimental test articles are given IP twice or once a week beginning in week 8 or 11 for fibrosis or cirrhosis respectively. At the end of the treatment period, rats are placed under anesthesia using isofluorane between 1-5% through inhalation and a laparotomy is performed. At the time of sacrifice, portal pressure is measured using a 16 G angiocatheter introduced into the portal vein to measure the height of a water column. The liver is removed, weighed, and pieces from the largest lobes are used for further analysis. The spleen is also removed and weighed before being discarded.

Representative histology of Sirius red stained liver sections from experiment described is taken for comparison between treated animals and control. A 20% reduction in mean collagen (stained red) is statistical acceptable for anti-fibrosis effect. Strands of bridging fibrosis indicate advance fibrosis stage (these are strands of collagen fibers).
Biochemical Tests:
As in the NASH model various diagnostic tests are done to evaluate the extent of liver damage due to the fibrosis:

Liver functions are evaluated in Plasma for levels of AST, ALT, total bilirubin, creatinine, and TG are measured by example FUJI DRY CHEM 7000 (Fuji Film, Japan).

Liver biochemistry: To quantify liver hydroxyproline content, a quantitative assessment of collagen content, frozen liver samples (40-70 mg) were processed by a standard alkaline-acid hydrolysis method and hydroxyproline content was normalized to total liver proteins.

Total liver lipid-extracts are obtained from caudate lobes by Folch's method and liver TG levels are measured using the Triglyceride E-test (Wako, Japan).

Histopathological and immunohistochemical analyses liver sections are cut from paraffin blocks of liver tissue prefixed in Bouin's solution and stained with Lillie-Mayer's Hematoxylin (Muto Pure Chemicals, Japan) and eosin solution (Wako, Japan).

To visualize collagen deposition, Bouin's fixed liver sections are stained using picro-Sirius red solution (Waldeck GmbH & Co. KG, Germany). NAFLD Activity score (NAS) is also calculated according to established criteria.

Immunohistochemistry for SMA, F4/80, Gal-3, CD36 and iNOS can estimated from each positive area as indication of the extent of inflammation and fibrosis.
Bile Duct Models of Liver Fibrosis These experiments are done to evaluate the efficacy of the compounds described herein on the fibrosis of the liver following bile duct ligation or treatment with drugs that cause biliary fibrosis. Animals treated with various compounds described herein show that liver fibrosis is reduced in comparison to vehicle controls.

Example 10: In Vivo Animal Models of Lung Fibrosis

These experiments are done to evaluate the efficacy of the compounds described herein on the prevention of bleomycin-induced pulmonary fibrosis. An untreated control group with intratracheal saline infusion consisted of 10 mice. Bleomycin is administered by slow intratracheal infusion into the lungs of other groups on Day 0. On Days–1, 2, 6, 9, 13, 16 and 20, mice are dosed (iv, ip, subcut, or oral) once daily with vehicle or various doses of compounds described herein (iv, ip, subcut, or oral) CT-01 (Group 3). Animals are weighed and evaluated for respiratory distress daily. On Day 21, all animals are euthanized and the wet weight of lungs is measured. Upon sacrifice, blood is collected via retro-orbital bleed for preparation of serum. The right lobe of the lung is snap frozen for subsequent hydroxyproline analysis while the left is insufflated and fixed in 10% formalin for histological analysis. The formalin-fixed lung is processed for routine histological evaluation.

Example 11: In Vivo Animal Models of Kidney Fibrosis

These experiments are done to evaluate the efficacy of the compounds described herein on the fibrosis of the kidney using models of unilateral ureteral ligation and diabetic nephropathy. Animals treated with various compounds described herein show that kidney fibrosis is reduced in comparison to vehicle controls.

Example 12: In Vivo Animal Models of Cardiovascular Fibrosis

These experiments are done to evaluate the efficacy of the compounds described herein on the fibrosis of the heart and vessels using models of heart failure, atrial fibrillation, pulmonary hypertension, and atherosclerosis. Animals treated with various compounds described herein show that cardiovascular fibrosis is reduced in comparison to vehicle controls.

Example 13: VEGF-A-Induced Angiogenesis

Vascular endothelial growth factors (VEGFs) signaling though VEGF receptor-2 (VEGFR-2) is the primary angiogenic pathway. Galectin proteins are important for the signaling pathway. Compounds described herein are able to inhibit neovascularization of mouse cornea in response to injury.

Example 14: Gal-3 Causes Systemic Insulin Resistance In-Vivo and Impairs Insulin Action in Adipocytes, and Hepatocytes In obesity, macrophages and other immune cells accumulate in insulin target tissues, promoting a chronic inflammatory state and insulin resistance.

Gal-3 has been reported to be elevated in both obese subjects and mice [Li et al, Cell (2016), 167 (4), p 973-984]. Administration of Gal-3 to mice causes glucose intolerance by blocking insulin receptor (IR) activation of glucose uptake when insulin binds to its receptor, whereas inhibition of Gal-3 improved insulin sensitivity in obese mice. The compounds described herein bind to Gal-3 allosterically and inhibit its binding to the insulin receptor (IR) and thus causing the reversal of the downstream inhibition of IR signaling and glucose uptake caused by elevated Gal-3. FIG. 12F demonstrate inhibition of Gal-3 binding to IR at 50 ηM to 20 μM range.

This in-vivo model linked Gal-3 causing inflammation and decreased insulin sensitivity. Thus, compounds that inhibit Gal-3 binding to IR could be therapeutically used to treat insulin resistance.

Example 15: Evaluation of Compound Absorption, Distribution, Metabolism, and Elimination Compounds described herein are evaluated for physico-chemical properties, including but not limited to solubility (Thermodynamic and Kinetic method), various pH changes, solubility in biorelevant medium (FaSSIF, FaSSGF, FeSSIF), Log D (Octanol/water and Cyclohexane/water), chemical stability in plasma, and blood partitioning.

Compounds described herein are evaluated for in vitro permeability properties, including but not limited to PAMPA (parallel artificial membrane permeability assay), Caco-2, and MDCK (wild type)

Compounds described herein are evaluated for animal pharmacokinetic properties, including but not limited to pharmacokinetics by various routes viz., oral, intravenous, intraperitoneal, subcutaneous in mice (Swiss Albino, C57, Balb/C), rats (Wistar, Sprague Dawley), rabbits (New Zealand white), dogs (Beagle), Cynomolgus monkeys, etc., tissue distribution, brain to plasma ratio, biliary excretion, and mass balance.

Compounds described herein are evaluated for protein binding, including but not limited to plasma protein binding (ultra-filtration and Equilibrium Dialysis) and microsomal protein binding.

Compounds described herein are evaluated for in vitro metabolism, including but not limited to cytochrome P450 inhibition, cytochrome P450 time dependent inhibition, metabolic stability, liver microsome metabolism, S-9 fraction metabolism, effect on cryopreserved hepatocyte, plasma stability, and AGSH trapping.

Compounds described herein are evaluated for metabolite identification, including but not limited to identification in vitro (microsomes, S-9 and hepatocytes) and in vivo samples.

Example 16: Therapeutic Potential of Targeting IGF Signaling

IGF system signaling has critical importance on growth and development, however, it is also critical in other key physiologic functions including energy systems integration, glucose/insulin regulation, mammary development and lactation, bone health, neuronal maintenance. Targeting the IGF signaling pathway has been reported as a promising strategy in the development of novel anti-cancer therapeutics. The expression of IGF-1R, the major signal transducing receptor of the pathway, appears to be necessary for malignant transformation as when it was overexpressed the timing and frequency of tumor development in animal models increased. Also, IGF-1 deficient mice have greatly reduced capacity to support tumor growth and metastasis. Through its antiproliferative activity, inhibitors of the IGF-1R system may provide a number of clinically important benefits. For instance, maintenance therapy, aimed at suppressing growth of residual, subclinical disease, IGF-1R blockade has the potential for numerous clinically useful effects, including increasing the proportion, extent and duration of clinical responses from cytotoxic therapies when used in combination with chemotherapy.

Figures 1, 12G:
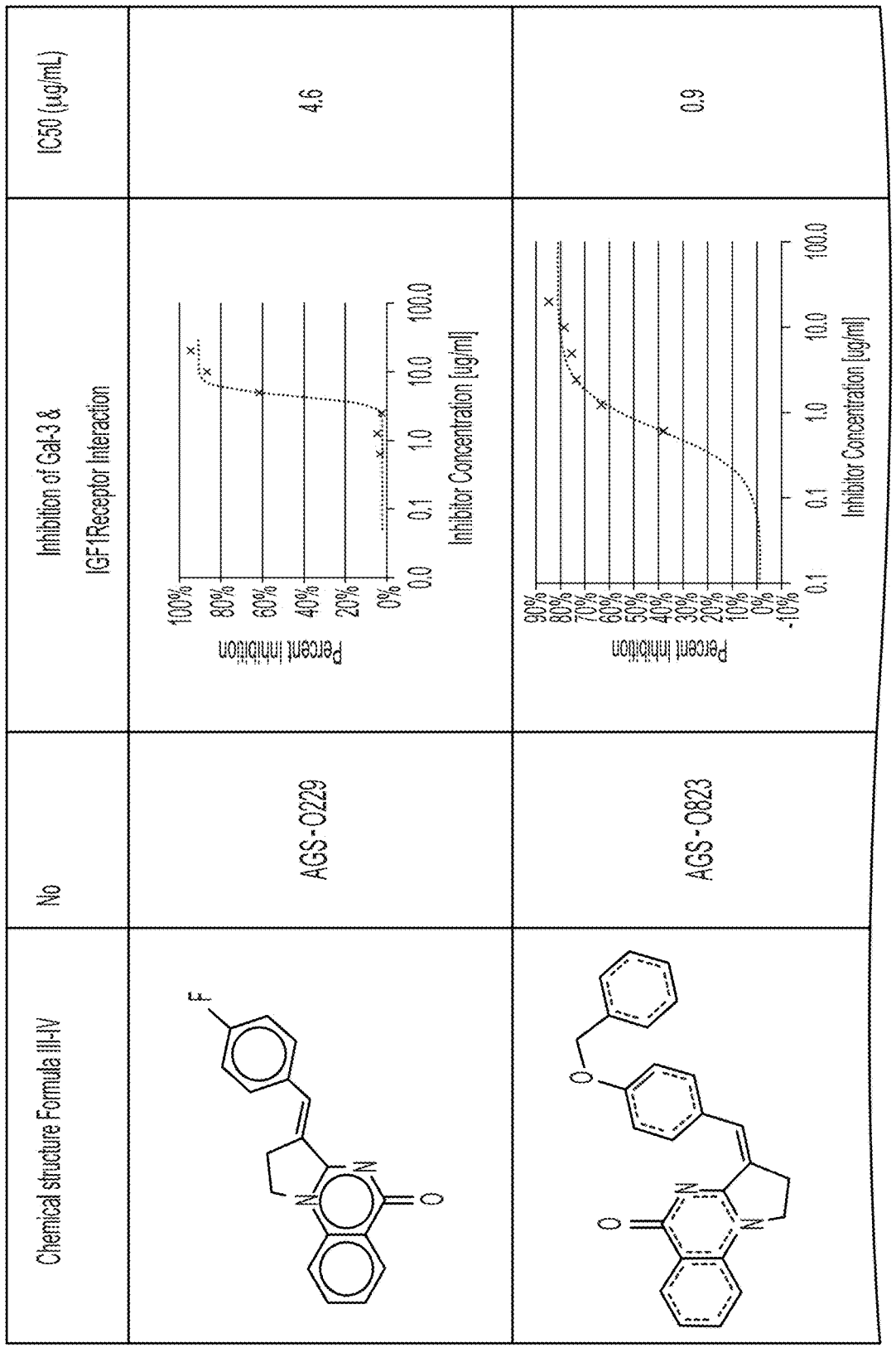
FIG. 12G depicts that the compounds according to embodiments of the invention modulate Gal-3 binding to Insulin Like Growth Factor 1 Receptor (IGFR1, gene IGF1R) at low μM levels similar to galactoside derivatives.
Figures 2, 12G:
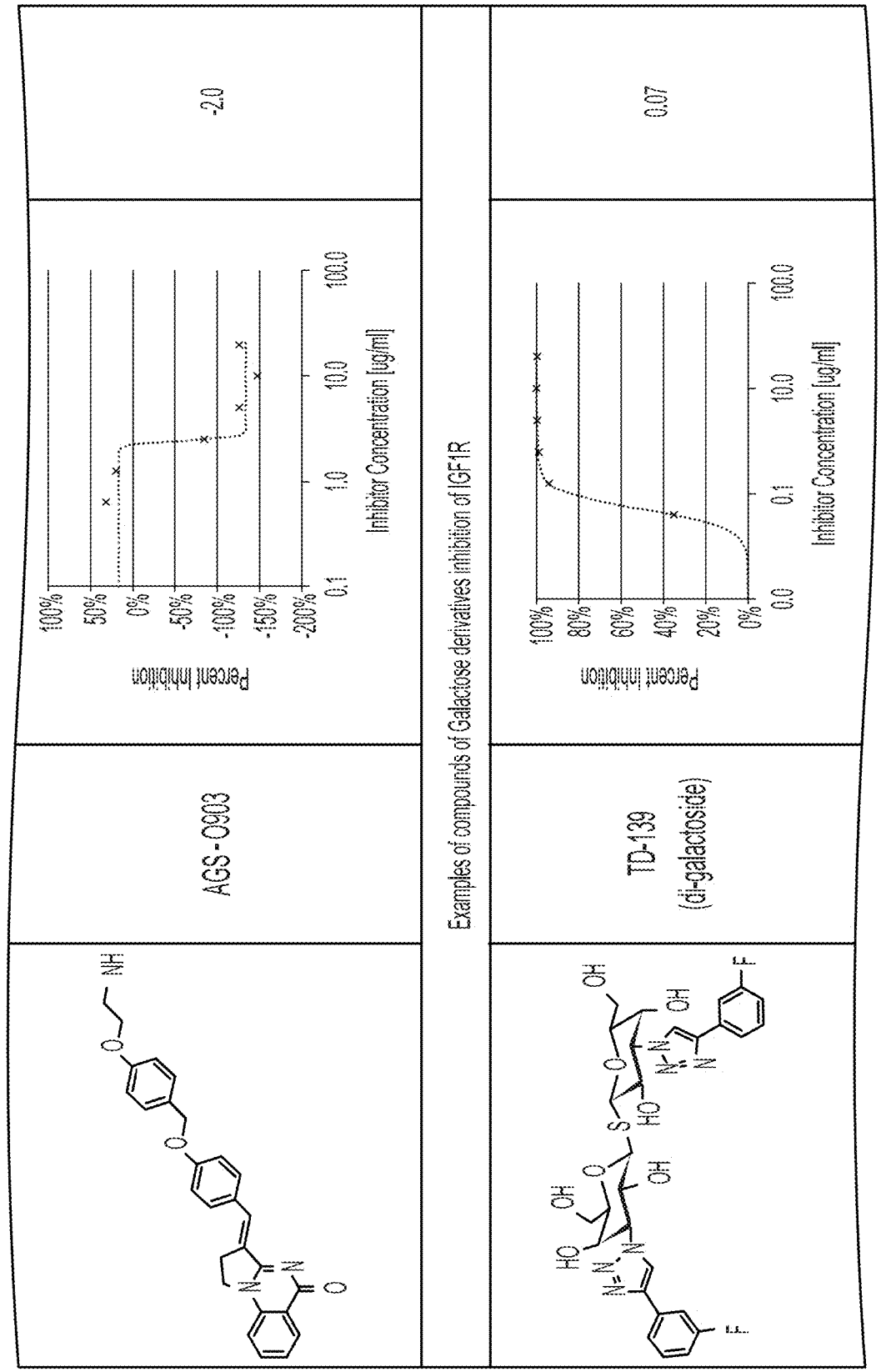
Figures 3, 12G:
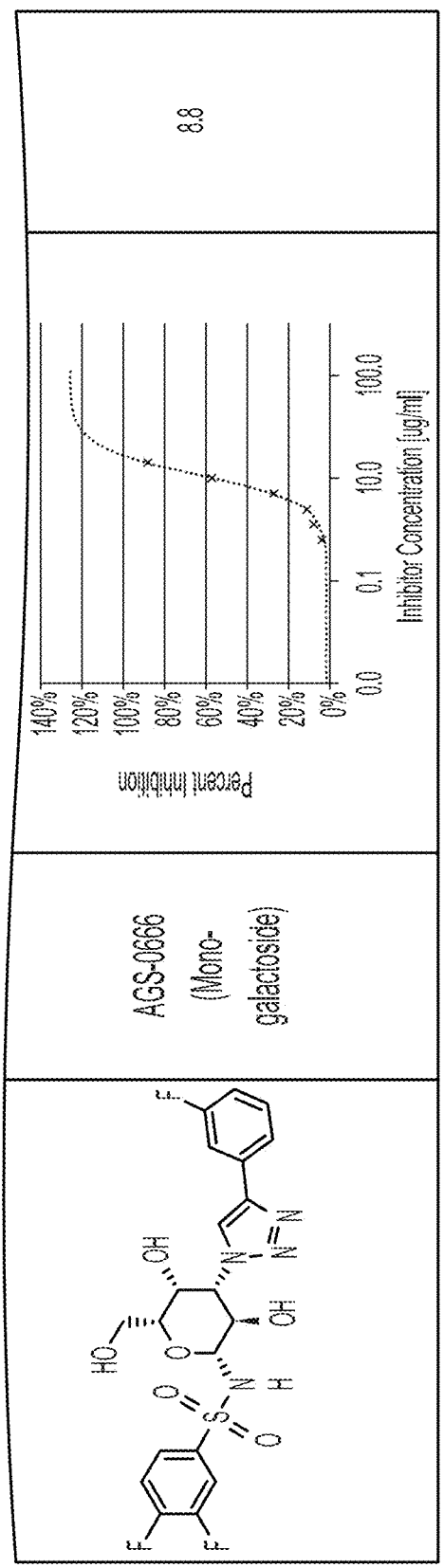

Using the ELISA composition assay described herein, in which the compounds were incubated with Gal-3 and the binding of Gal-3 with IGF-Receptor was tested. FIG. 12G shows that that Galectin-3 strongly binds to IGF-R1 and the compounds describe herein can modulate the binding of Gal-3 to IGF-R1. As shown in FIG. 12G the compounds can inhibit (positive IC50) or enhance (negative IC50) the binding of Galectin-3 to IGF-R1 and thus effecting the IGF signaling pathway.

FIG. 12G shows comparison of the compounds described herein with galactose derivative compounds. Contrary to the galactose derivatives compounds (for example, TD-139 and AGS-0666) that directly bind to the Gal-3 carbohydrate

The invention claimed is:

1. A compound of Formula I or a pharmaceutically acceptable salt or solvate thereof:

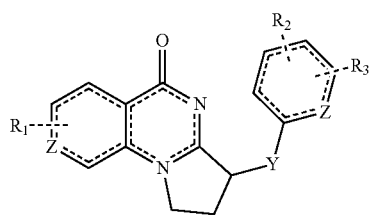

Formula I wherein Y linkage is (—CH=) or (—CH2-) or —CH2-X— wherein X is nitrogen, oxygen, sulfur or selenium;

wherein Z is a carbon;

wherein R1 is hydrogen, oxygen, amine, carboxyl, C1-C6 alkyl, C1-C4 alkoxy, aryl, halogen, trifluoromethyl, dinitromethyl or a combination of the foregoing; and wherein R2, R3 or R2 and R3 are aryl group with one or more substitutions, wherein the one or more substitution is hydroxyl, amine, C1-C6 alkyl, C1-C4 alkoxy, halogen, benzene or combinations thereof.

2. A compound of Formula I or a pharmaceutically acceptable salt or solvate thereof:

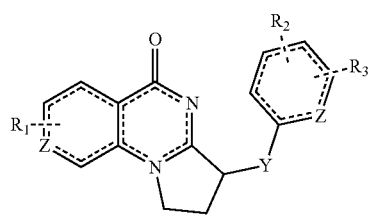

Formula I wherein Y linkage is (—CH=) or (—CH2-) or —CH2-X— wherein X is nitrogen, oxygen, sulfur or selenium;

wherein Z is a carbon;

wherein R1 is hydrogen, oxygen, amine, carboxyl, C1-C6 alkyl, C1-C4 alkoxy, aryl, halogen, trifluoromethyl, dinitromethyl or a combination of the foregoing; and wherein R2, R3 or R2 and R3 are fluoromethyl.

3. A compound selected from the compounds having the formula of Table 1

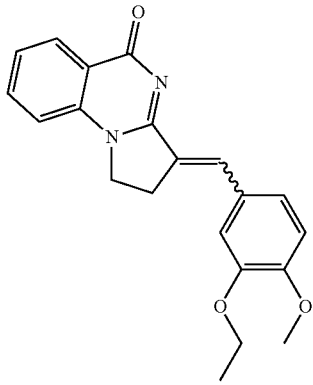

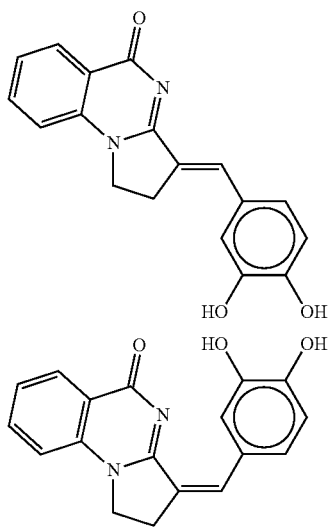

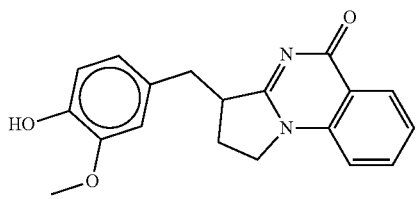

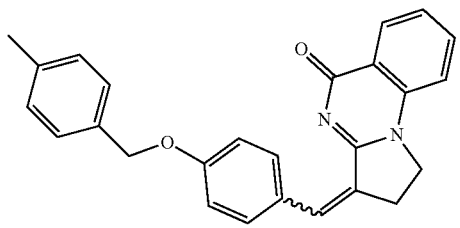

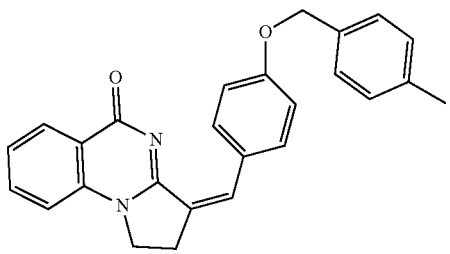

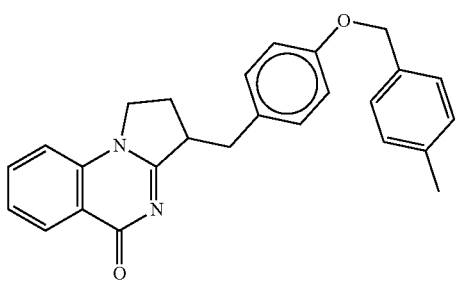
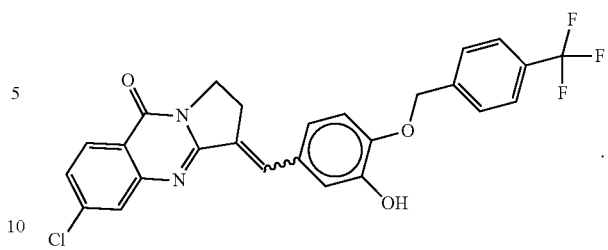
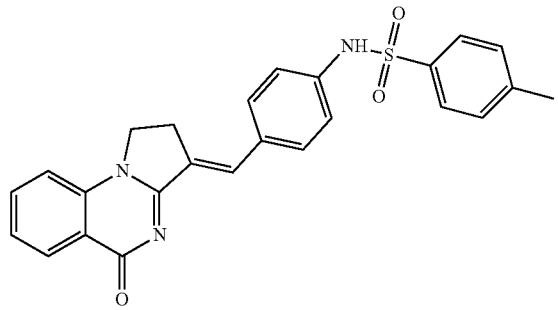
4. A compound having one of the formula of Table 6
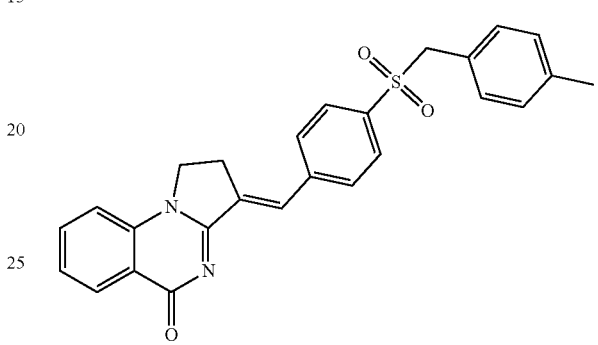
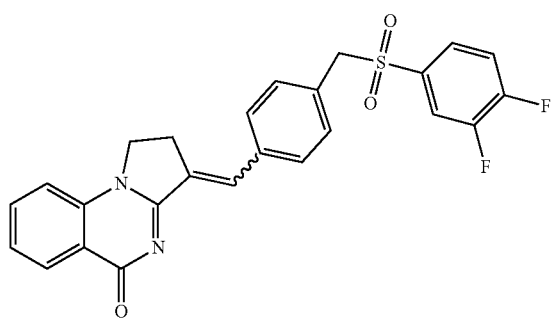
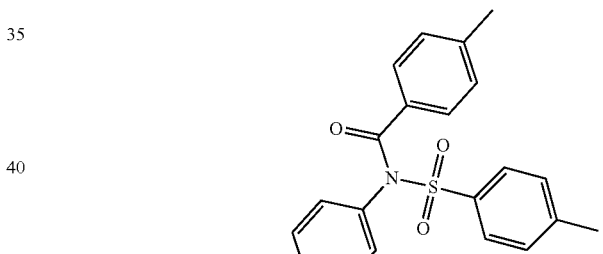
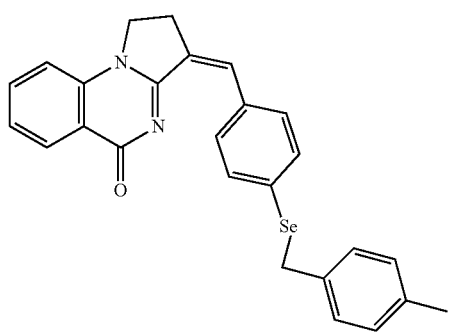
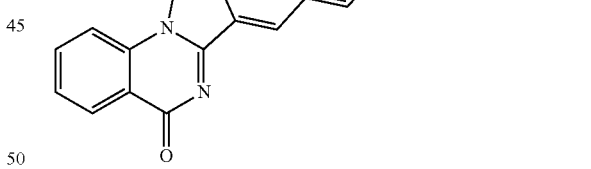
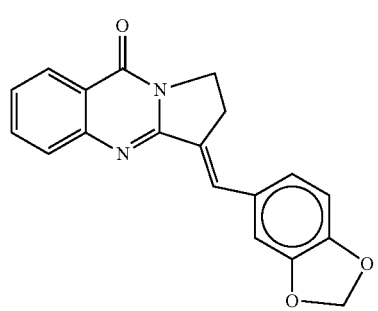

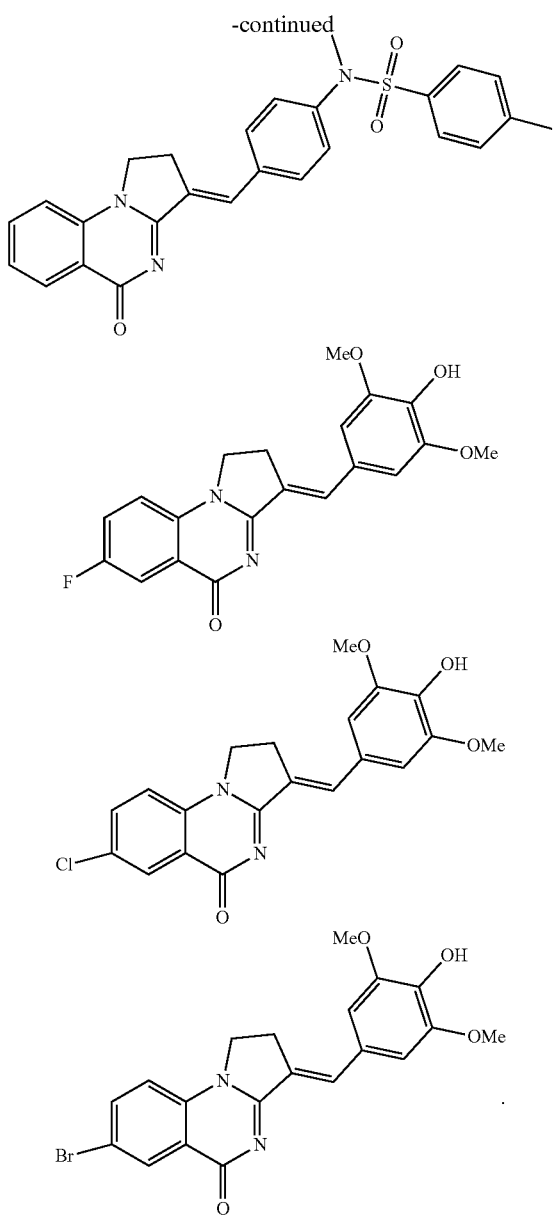

5. A composition comprising a therapeutically effective amount of the compound of of claim 1, and a pharmaceutically acceptable adjuvant, excipient, formulation carrier or combinations thereof.

6. A composition comprising a therapeutically effective amount of the compound of claim 1, and a therapeutically effective amount of an anti-inflammatory drug, anti-fibrosis drug, pharmaceutical drug, nutraceutical drug, supplement, or combinations thereof.

7. A method of treatment of a disease in a subject in need thereof, comprising administering a therapeutically effective amount of a pharmaceutical composition comprising at least one compound according to claim 1, wherein the disease is a disorder related to pathological disease due to elevated galectin-3.

8. A method of treatment of a disease in a subject in need thereof, comprising administering a therapeutically effective amount of a pharmaceutical composition comprising at least one compound according to claim 1, wherein the disease is alcoholic or viral steatohepatitis a nonalcoholic steatohepatitis, fibrosis, cirrhosis, inflammatory disorder, metabolic disorder, insulin resistance, autoimmune disorder, neoplastic condition, metabolic disorder or cancer.

9. A method of treatment of a disease in a subject in need thereof, comprising administering a therapeutically effective amount of a pharmaceutical composition comprising at least one compound according to claim 1, wherein the disease is heart failure, arrhythmias, uremic cardiomyopathy, chronic kidney, idiopathic lung diseases, skin autoimmune, proliferative and fibrotic skin disorder, optionally psoriasis or atopic dermatitis.

10. A method of treatment of a disease in a subject in need thereof, comprising administering a therapeutically effective amount of a pharmaceutical composition comprising at least one compound according to claim 1, wherein the at least one compound modulates Gal-3 binding to Insulin receptor and Insulin Like Growth Factor 1 Receptor.

11. A method of treatment of a disease in a subject in need thereof, comprising administering a therapeutically effective amount of a pharmaceutical composition comprising at least one compound according to claim 1, wherein the disease is an inflammatory disorder and wherein the inflammatory disorder is inflammatory bowel disease, Crohn's disease, multiple sclerosis, Systemic Lupus Erythematosus, arthritis, rheumatoid arthritis, asthma or ulcerative colitis.

12. A composition comprising a therapeutically effective amount of the compound of claim 2, and a pharmaceutically acceptable adjuvant, excipient, formulation carrier or combinations thereof.

13. A method of treatment of a disease in a subject in need thereof, comprising administering a therapeutically effective amount of a pharmaceutical composition comprising at least one compound according to claim 2, wherein the disease is a disorder related to pathological disease due to elevated galectin-3.

14. A method of treatment of a disease in a subject in need thereof, comprising administering a therapeutically effective amount of a pharmaceutical composition comprising at least one compound according to claim 2, wherein the disease is alcoholic or viral steatohepatitis a nonalcoholic steatohepatitis, fibrosis, cirrhosis, inflammatory disorder, metabolic disorder, insulin resistance, autoimmune disorder, neoplastic condition, metabolic disorder or cancer.

15. A method of treatment of a disease in a subject in need thereof, comprising administering a therapeutically effective amount of a pharmaceutical composition comprising at least one compound according to claim 2, wherein the disease is heart failure, arrhythmias, uremic cardiomyopathy, chronic kidney, idiopathic lung diseases, skin autoimmune, proliferative and fibrotic skin disorder, optionally psoriasis or atopic dermatitis.

16. A method of treatment of a disease in a subject in need thereof, comprising administering a therapeutically effective amount of a pharmaceutical composition comprising at least one compound according to claim 2, wherein the at least one compound modulates Gal-3 binding to Insulin receptor and Insulin Like Growth Factor 1 Receptor.

17. A method of treatment of a disease in a subject in need thereof, comprising administering a therapeutically effective amount of a pharmaceutical composition comprising at least one compound according to claim 2, wherein the disease is an inflammatory disorder and wherein the inflammatory disorder is inflammatory bowel disease, Crohn's disease, multiple sclerosis, Systemic Lupus Erythematosus, arthritis, rheumatoid arthritis, asthma or ulcerative colitis.

18. A composition comprising a therapeutically effective amount of the compound of claim 3, and a pharmaceutically acceptable adjuvant, excipient, formulation carrier or combinations thereof.

19. A method of treatment of a disease in a subject in need thereof, comprising administering a therapeutically effective amount of a pharmaceutical composition comprising at least one compound according to claim 3, wherein the disease is a disorder related to pathological disease due to elevated galectin-3.

20. A method of treatment of a disease in a subject in need thereof, comprising administering a therapeutically effective amount of a pharmaceutical composition comprising at least one compound according to claim 3, wherein the disease is alcoholic or viral steatohepatitis a nonalcoholic steatohepatitis, fibrosis, cirrhosis, inflammatory disorder, metabolic disorder, insulin resistance, autoimmune disorder, neoplastic condition, metabolic disorder or cancer.

21. A method of treatment of a disease in a subject in need thereof, comprising administering a therapeutically effective amount of a pharmaceutical composition comprising at least one compound according to claim 3, wherein the disease is heart failure, arrhythmias, uremic cardiomyopathy, chronic kidney, idiopathic lung diseases, skin autoimmune, proliferative and fibrotic skin disorder, optionally psoriasis or atopic dermatitis.

22. A method of treatment of a disease in a subject in need thereof, comprising administering a therapeutically effective amount of a pharmaceutical composition comprising at least one compound according to claim 3, wherein the at least one compound modulates Gal-3 binding to Insulin receptor and Insulin Like Growth Factor 1 Receptor.

23. A method of treatment of a disease in a subject in need thereof, comprising administering a therapeutically effective amount of a pharmaceutical composition comprising at least one compound according to claim 3, wherein the disease is an inflammatory disorder and wherein the inflammatory disorder is inflammatory bowel disease, Crohn's disease, multiple sclerosis, Systemic Lupus Erythematosus, arthritis, rheumatoid arthritis, asthma or ulcerative colitis.

24. A composition comprising a therapeutically effective amount of the compound of claim 4, and a pharmaceutically acceptable adjuvant, excipient, formulation carrier or combinations thereof.

25. A method of treatment of a disease in a subject in need thereof, comprising administering a therapeutically effective amount of a pharmaceutical composition comprising at least one compound according to claim 4, wherein the disease is a disorder related to pathological disease due to elevated galectin-3.

26. A method of treatment of a disease in a subject in need thereof, comprising administering a therapeutically effective amount of a pharmaceutical composition comprising at least one compound according to claim 4, wherein the disease is alcoholic or viral steatohepatitis a nonalcoholic steatohepatitis, fibrosis, cirrhosis, inflammatory disorder, metabolic disorder, insulin resistance, autoimmune disorder, neoplastic condition, metabolic disorder or cancer.

27. A method of treatment of a disease in a subject in need thereof, comprising administering a therapeutically effective amount of a pharmaceutical composition comprising at least one compound according to claim 4, wherein the disease is heart failure, arrhythmias, uremic cardiomyopathy, chronic kidney, idiopathic lung diseases, skin autoimmune, proliferative and fibrotic skin disorder, optionally psoriasis or atopic dermatitis.

28. A method of treatment of a disease in a subject in need thereof, comprising administering a therapeutically effective amount of a pharmaceutical composition comprising at least one compound according to claim 4, wherein the at least one compound modulates Gal-3 binding to Insulin receptor and Insulin Like Growth Factor 1 Receptor.

29. A method of treatment of a disease in a subject in need thereof, comprising administering a therapeutically effective amount of a pharmaceutical composition comprising at least one compound according to claim 4, wherein the disease is an inflammatory disorder and wherein the inflammatory disorder is inflammatory bowel disease, Crohn's disease, multiple sclerosis, Systemic Lupus Erythematosus, arthritis, rheumatoid arthritis, asthma or ulcerative colitis.

\* \* \* \* \*